United States Patent [19]
Reed et al.

[11] Patent Number: 6,159,960
[45] Date of Patent: *Dec. 12, 2000

[54] STEROID SULPHATASE INHIBITORS

[75] Inventors: Michael John Reed, London; Barry Victor Lloyd Potter, Bathford, both of United Kingdom

[73] Assignee: Sterix Limited, Oxford, United Kingdom

[*] Notice: This patent is subject to a terminal disclaimer.

[21] Appl. No.: 09/193,969

[22] Filed: Nov. 18, 1998

Related U.S. Application Data

[62] Continuation-in-part of application No. 09/111,927, Jul. 8, 1998, Pat. No. 6,011,024, which is a continuation-in-part of application No. 08/458,352, Jun. 2, 1995, Pat. No. 5,830,886, which is a division of application No. 08/196,192, filed as application No. PCT/GB92/01587, Aug. 28, 1992, Pat. No. 5,616,574, and a continuation-in-part of application No. 09/142,194, filed as application No. PCT/GB97/00600, Mar. 4, 1997, and a continuation-in-part of application No. 09/125,255, filed as application No. PCT/GB97/00444, Feb. 17, 1997, and a continuation-in-part of application No. PCT/GB97/03352, Dec. 4, 1997.

[30] Foreign Application Priority Data

Aug. 28, 1991 [GB] United Kingdom .................. 9118478

[51] Int. Cl.[7] ................................................. A61K 31/56
[52] U.S. Cl. .................... 514/178; 514/456; 514/457; 514/459; 514/660; 514/601; 514/603; 514/604
[58] Field of Search .................... 514/178, 456, 514/457, 459, 460, 601, 603, 604

[56] References Cited

U.S. PATENT DOCUMENTS

| | | |
|---|---|---|
| 4,937,237 | 6/1990 | Holt et al. . |
| 5,281,587 | 1/1994 | Reed . |
| 5,344,827 | 9/1994 | Reed . |
| 5,604,215 | 2/1997 | Reed et al. . |
| 5,616,574 | 4/1997 | Reed et al. . |
| 5,677,292 | 10/1997 | Li et al. . |
| 5,830,886 | 11/1998 | Reed et al. . |
| 5,880,115 | 3/1999 | Li et al. . |

FOREIGN PATENT DOCUMENTS

| | | |
|---|---|---|
| 645975 | 2/1994 | Australia . |
| 0 403 185 | 12/1990 | European Pat. Off. . |
| 2113484 | 12/1972 | France . |
| 114806 | 8/1975 | Germany . |
| 1398026 | 6/1975 | United Kingdom . |
| WO 97/30041 | 8/1997 | WIPO . |
| WO 97/32872 | 9/1997 | WIPO . |
| WO 98/24802 | 6/1998 | WIPO . |

OTHER PUBLICATIONS

Li et al, J Steroid Biochem. 59 (1) 41–48, 1996.
Stolzer, "Animal Experimental Contribution to the Development of Estrogenic Substances", Dissertation for award of Doctor of Science degree at the Mathematic–Naturwissenschaftlichh–Technischen faculty of Friedrich–Schiller–University Jena, Jul. 1989.
Clausen, Erythrocytes as a drug carrier—Investigations with selected estrogens for loading following oral administration, Natural Science Faculty, Science Council, Martin–Luther Unversitat Halle–Wittenberg, Germany, Aug. 1989.
Schwarz et al., Pharmazie, vol. 30 (1975), pp. 17–21.
Zeitschrift Fur Chemie, vol. 14, No. 1, 1974, pp. 15–16.
Townsley et al., Research Steroids, vol. 5 (1973), pp. 73–78.

*Primary Examiner*—Rebecca Cook
*Attorney, Agent, or Firm*—Frommer Lawrence & Haug LLP; Thomas J. Kowalski

[57] ABSTRACT

A method of inhibiting steroid sulphatase activity in a subject in need of same is described.

The method comprises administering to said subject a steroid sulphatase inhibiting amount of a ring system compound; which ring system compound comprises a ring to which is attached a sulphamate group of the formula

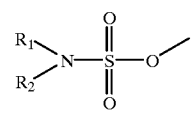

wherein each of $R_1$ and $R_2$ is independently selected from H, alkyl, alkenyl, cycloalkyl and aryl, or together represent alkylene optionally containing one or more hetero atoms or groups in the alkylene chain; and wherein said compound is an inhibitor of an enzyme having steroid sulphatase activity (E.C.3.1.6.2); and if the sulphamate group of said compound is replaced with a sulphate group to form a sulphate compound and incubated with a steroid sulphatase enzyme (E.C.3.1.6.2) at a pH 7.4 and 37° C. it would provide a $K_m$ value of less than 50 μM.

9 Claims, 26 Drawing Sheets

KEY ENZYMES IN STEROIDOGENESIS:- 1. SULPHATASE 2. AROMATASE 3. DEHYDROGENASE 4. 5α REDUCTASE

| X | |
|---|---|
| (1) | -OH |
| (2) | $-OSO_3^-$ |
| (3) | $-OSO_2NH_2$ |
| (4) | $-NHSO_2NH_2$ |
| (5) | $-SSO_2NH_2$ |

| | X | $R_1$ | $R_2$ | $R_3$ |
|---|---|---|---|---|
| (11) | -OH | H | H | H |
| (12) | $-OSO_3-$ | H | $CH_3$ | H |
| (13) | $-OSO_2NH_2$ | H | H | H |
| (14) | $-OSO_2NH_2$ | H | $CH_3$ | H |
| (15) | $-OSO_2NH_2$ | $CH_3$ | $CH_3$ | $CH_3$ |
| (16) | $-OSO_2NH_2$ | H | $CF_3$ | H |

FIG. 13
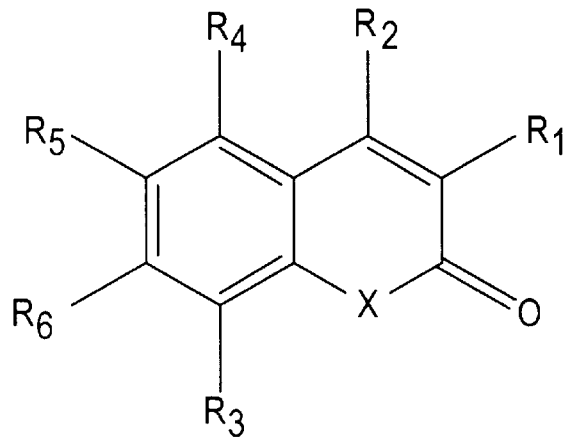
(A)
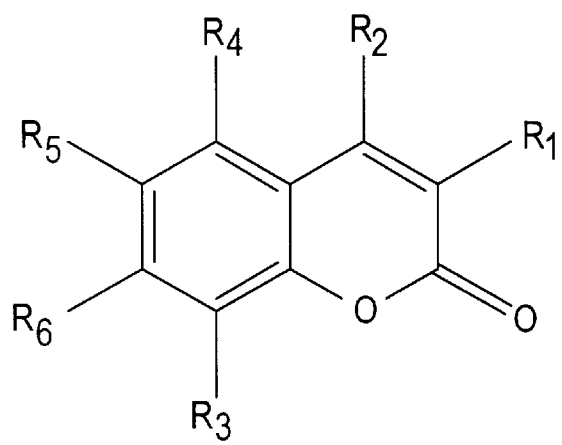
(B)
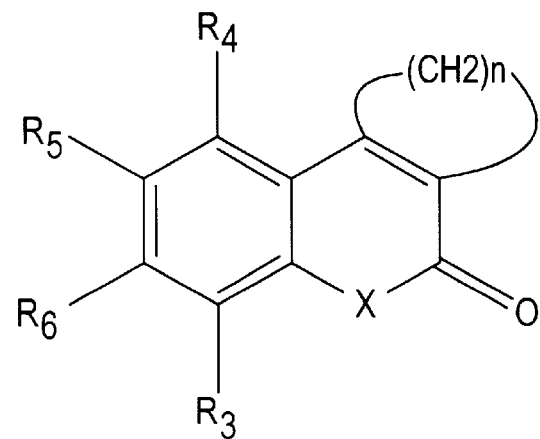
(C)

ORIGIN OF OESTROGENIC STEROIDS IN POSTMENOPAUSAL WOMEN

ER=OESTROGEN RECEPTOR, DHA/ -S=DEHYDROEPIANDROSTERONE / -SULPHATE, ADIOL=ANDROSTENEDIOL, E1-STS=OESTRONE SULPHATASE, DHA-STS= DHA-SULPHATASE, ADIOL-STS=ADIOL SULPHATASE, 17B-HSD=OESTRADIOL 17B-HYDROXYSTEROID DEHYDROGENASE

I

II

III

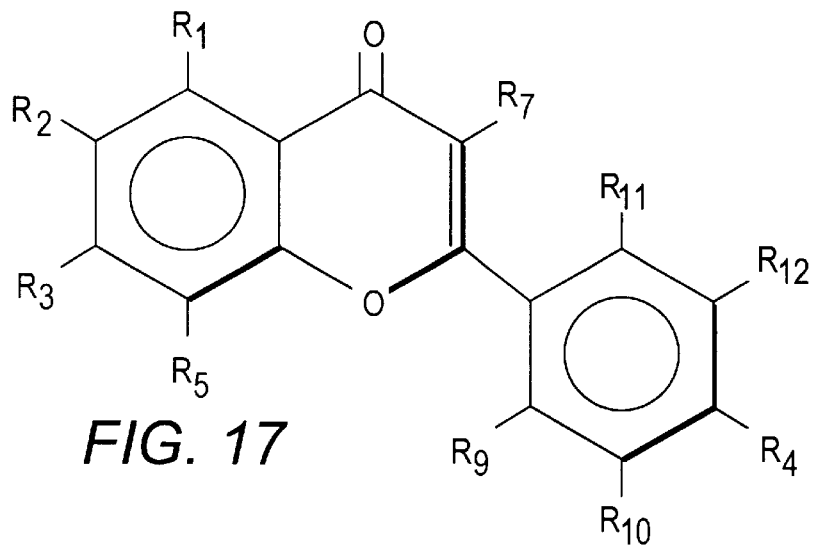
FIG. 17  IV
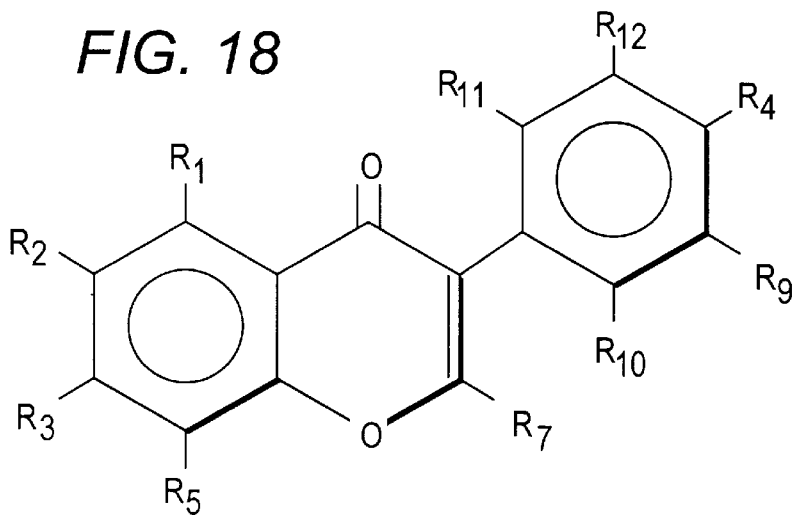
FIG. 18  V
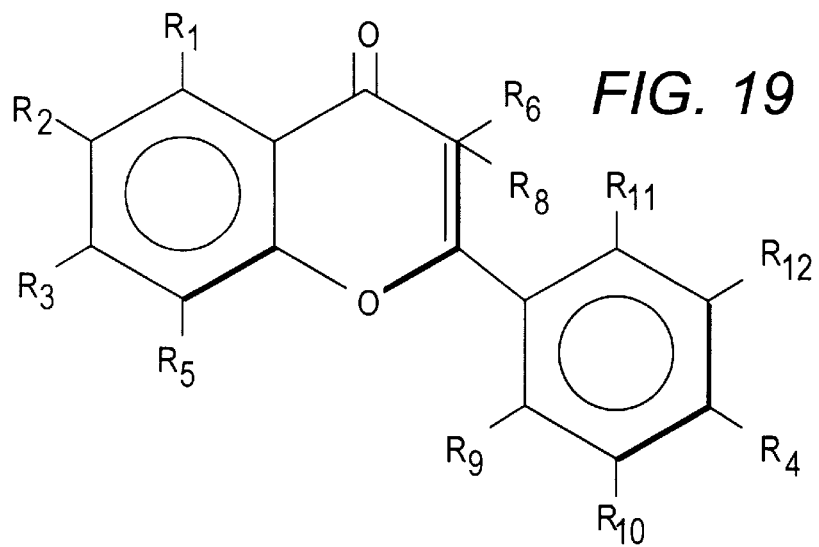
FIG. 19  VI

X

X - B - A     I
FIG.25
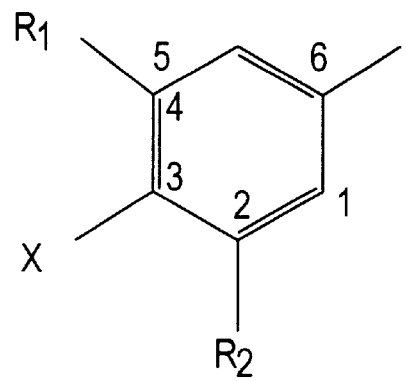
II
FIG.26
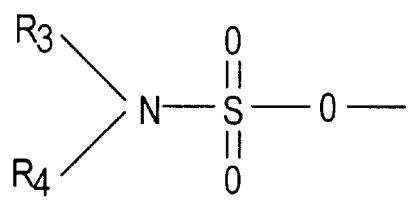
III
FIG.27
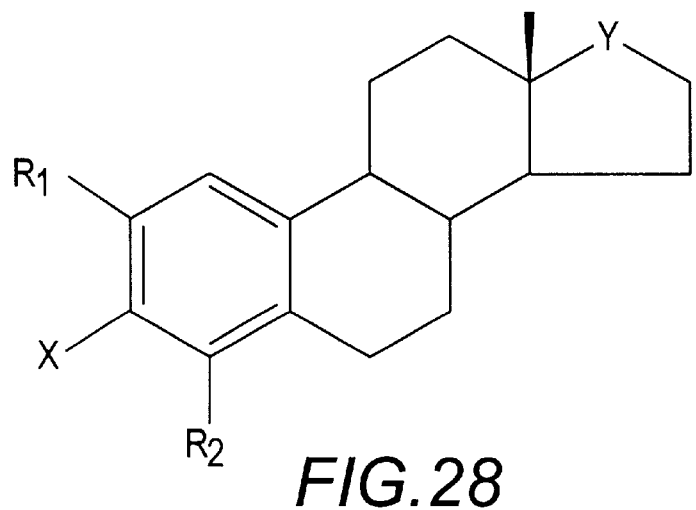
IV
FIG.28

STEROID SULPHATASE INHIBITORS

This application is a continuation-in-part of U.S. application Ser. No. 09/111,927, filed Jul. 8, 1998, now U.S. Pat. No. 6,011,024, and incorporated herein by reference, which in turn was a continuation-in-part of U.S. application Ser. No. 08/458,352, filed Jun. 2, 1995, now U.S. Pat. No. 5,830,886, and incorporated herein by reference, which was a division of U.S. application Ser. No. 08/196,192, filed (§102(e) date of) Dec. 27, 1994, now U.S. Pat. No. 5,616,574 and incorporated herein by reference. U.S. application Ser. No. 08/196,192 was the U.S. National Phase of PCT/GB92/01587, filed Aug. 28, 1992 and designating the U.S. and incorporated herein by reference. U.S. application Ser. No. 08/196,192 has a 0371 date of Dec. 27, 1994 and a §102(e) date of Dec. 27, 1994. PCT/GB92/01587 was published as WO93/05064 (incorporated herein by reference), has a publication date of Mar. 18, 1993, and claims priority from United Kingdom patent application Ser. No. 9,118,478, filed Aug. 29, 1991. This application is also a continuation-in-part of allowed U.S. application Ser. No. 09/142,194, filed Sep. 2, 1998 allowed, no number yet and of PCT patent application No. PCT/GB97/00600, filed Mar. 4, 1997, designating the U.S., and claiming priority from United Kingdom patent applications 9604709.7 and 9605725.2, filed Mar. 5 and 19, 1996, respectively. PCT/GB97/00600 was published as WO 97/32872 on Sep. 12, 1997. This application is also a continuation-in-part of allowed U.S. application Ser. No. 09/125,255, filed Aug. 14, 1998 allowed, no number yet and of PCT patent application No. PCT/GB97/00444, filed Feb. 17, 1997, designating the U.S., and claiming priority from United Kingdom patent application 96033253, filed Feb. 16, 1996. PCT/GB97/00444 was published as WO 97/30041 on Aug. 21, 1997. This application is also a continuation-in-part of PCT patent application number PCT/GB97/03352, filed Dec. 4, 1997, designating the U.S., and claiming priority from United Kingdom patent application 9625334.9, filed Dec. 5, 1996. PCT/GB97/03352 was published as WO 98/24802 on Jun. 11, 1998. Each of U.S. Ser. Nos. 09/142,194 and 09/125,255 and each of PCT/GB97/00600 (WO 97/32872), PCT/GB97/00444 (WO 97/30041), and PCT/GB97/03352 (WO 98/24802) is hereby incorporated herein by reference.

FIELD OF INVENTION

This invention relates to novel compounds for use as steroid sulphatase inhibitors, and pharmaceutical compositions containing them.

BACKGROUND AND PRIOR ART

Steroid precursors, or pro-hormones, having a sulphate group in the 3-position of the steroid nucleus, referred to hereinafter simply as steroid sulphates, are known to play an important part as intermediates in steroid metabolism in the human body. Oestrone sulphate and dehydroepiandrosterone (DHA) sulphate, for example, are known to play an important role as intermediates in the production, in the body, of oestrogens such as oestrone and oestradiol. Oestrone sulphate, in particular, is known, for example, to represent one of the major circulating oestrogen precursors particularly in post-menopausal women and oestrone sulphatase activity in breast tumours is 100–1000 fold greater than that of other enzymes involved in oestrogen formation (James et al., *Steroids*, 50, 269–279 (1987)).

Not only that, but oestrogens such as oestrone and oestradiol, particularly the over-production thereof, are strongly implicated in malignant conditions, such as breast cancer, see *Breast Cancer, Treatment and Prognosis*: Ed. R. A. Stoll, pp. 156–172, Blackwell Scientific Publications (1986), and the control of oestrogen production is the specific target of many anti-cancer therapies, both chemotherapy and surgical, e.g. oöphorectomy and adrenalectomy. So far as endocrine therapy is concerned, efforts have so far tended to concentrate on aromatase inhibitors, i.e. compounds which inhibit aromatase activity, which activity is involved, as the accompanying oestrogen metabolic flow diagram (FIG. 1) shows, in the conversion of androgens such as androstenedione and testosterone to oestrone and oestradiol respectively.

In recently published International Application WO91/13083 a proposal has been made to target a different point in the oestrogen metabolic pathway, or rather two different points, that is to say the conversion of DHA sulphate and oestrone sulphate to DHA and oestrone, respectively, by steroid sulphatase activity, and using 3-monoalkylthiophosphonate steroid esters as a steroid sulphatase inhibitor, more especially oestrone-3-monomethylthiophosphonate.

OBJECTS OF THE INVENTION

A first object of the present invention is to provide new compounds capable of inhibiting steroid sulphatase activity in vitro and in vivo.

A second object of the present invention is to provide new compounds having improved activity as steroid sulphatase inhibitors both in vitro and in vivo.

A third object of the invention is to provide pharmaceutical compositions effective in the treatment of oestrogen dependent tumours.

A fourth object of the invention is to provide pharmaceutical compositions effective in the treatment of breast cancer.

A fifth object of the invention is to provide a method for the treatment of oestrogen dependent tumours in mammals, especially humans.

A sixth object of the invention is to provide a method for the treatment of breast cancer in mammals and especially in women.

SUMMARY OF INVENTION

The invention is based on the discovery of novel compounds having steroid sulphatase inhibitory activity, in some cases, with extremely high activity levels.

In one aspect, the present invention provides a method of inhibiting steroid sulphatase activity in a subject in need of same.

In another aspect, the present invention provides compounds and compositions useful in that method of inhibiting steroid sulphatase activity.

The method of the present invention comprises administering to said subject a steroid sulphatase inhibiting amount of a ring system compound; which ring system compound comprises a ring to which is attached a sulphamate group of the formula

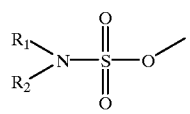

wherein each of $R_1$ and $R_2$ is independently selected from H, alkyl, alkenyl, cycloalkyl and aryl, or together represent alkylene optionally containing one or more hetero atoms or groups in the alkylene chain; and wherein said compound is an inhibitor of an enzyme having steroid sulphatase activity (E.C.3.1.6.2); and if the sulphamate group of said compound is replaced with a sulphate group to form a sulphate compound and incubated with a steroid sulphatase enzyme (E.C.3.1.6.2) at a pH 7.4 and 37° C. it would provide a $K_m$ value of less than 50 μM.

The compounds that are useful in the method of the present invention are sulphamic acid ester ring system compounds, the sulphate of which is a substrate for enzymes having steroid sulphatase (EC 3.1.6.2) activity, the N-alkyl and N-aryl derivatives of those sulphamic acid esters, and their pharmaceutically acceptable salts.

In one aspect of the present invention, compounds for use in the method of the present invention are the sulphamic acid esters of polycyclic alcohols, being polycyclic alcohols the sulphate of which is a substrate for enzymes having steroid sulphatase (EC 3.1.6.2) activity, the N-alkyl and N-aryl derivatives of those sulphamic acid esters, and their pharmaceutically acceptable salts.

For one aspect of the present invention, broadly speaking, the novel compounds of this invention are compounds of the Formula (I)

FORMULA (I)

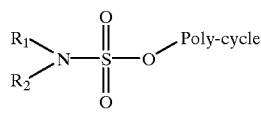

where:
$R_1$ and $R_2$ are each independently selected from H, alkyl, cycloalkyl, alkenyl and aryl, or together represent alkylene optionally containing one or more hetero atoms or groups in the alkylene chain; and the group —O-Polycycle represents the residue of a polycyclic alcohol, the sulphate of which is a substrate for enzymes having steroid sulphatase activity (EC 3.1.6.2).

As used herein the reference to polycyclic alcohols, the sulphate of which is a substrate for enzymes having steroid sulphatase activity refers to polycyclic alcohols, the sulphate of which, viz: the derivatives of the Formula:

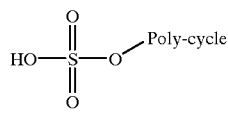

when incubated with steroid sulphatase EC 3.1.6.2 at pH 7.4 and 37° C. provides a $K_m$ value of less than 50 μmoles.

BRIEF DESCRIPTION OF DRAWINGS

The activity of the present compounds as steroid sulphatase inhibitors is illustrated in the accompanying drawings, in which:

FIGS. 13 and 14 present Formulae (A) to (H) with Formulae (A), (B) and (C) presented in FIG. 13 and Formulae (D), (E), (F), (G) and (H) presented in FIG. 14 (See Example 13. Preferably, in Formula (A), $R_1$–$R_6$ are independently selected from H, halo, hydroxy, sulphamate, alkyl and substituted variants or salts thereof; but wherein at least one of $R_1$–$R_6$ is a sulphamate group; and wherein X is any one of O, S, NH, a substituted N, $CH_2$, or a substituted C. Preferably X is O. Preferably, if the sulphamate group of the compound were to be replaced with a sulphate group to form a sulphate compound then that sulphate compound would be hydrolysable by an enzyme having steroid sulphatase (E.C. 3.1.6.2) activity. In a highly preferred embodiment, the compound is not hydrolysable by an enzyme having steroid sulphatase (E.C. 3.1.6.2) activity. In Formula (B) $R_1$–$R_6$ are independently selected from H, halo, hydroxy, sulphamate, alkyl and substituted variants or salts thereof; but wherein at least one of R1–R6 is a sulphamate group. The alkyl group(s) in Formula (A) or Formula (B) can be any suitable linear or branched alkyl group which may be saturated or unsaturated and/or substituted or non-substituted. The alkyl group may even be a cyclic alkyl group. For example, at least two of $R_1$–$R_6$ are linked to form a further cyclic component. Preferably $R_1$–$R_5$ are independently selected from H, alkyl and haloalkyl; preferably wherein $R_1$–$R_5$ are independently selected from H, $C_{1-6}$ alkyl and $C_{1-6}$ haloalkyl. Preferably $R_1$–$R_5$ are independently selected from H, $C_{1-3}$ alkyl and C1–3 haloalkyl. Preferably $R_1$–$R_5$ are independently selected from H, methyl and halomethyl. Preferably $R_6$ is $OSO_2NH_2$. In Formula (A) or Formula (B), two or more of $R_1$–$R_6$ may be linked together to form an additional cyclic structure. A typical example of such a compound has the general Formula (C), wherein any one of $R_3$–$R_6$ is a sulphamate group, and wherein n is an integer. Typically, R6 is a sulphamate group. A typical sulphamate group is —OS(O)(O)—$NH_2$. Preferably n is an integer of from 3 to 10, preferably from 3 to 7. Optionally, the group $(CH_2)n$ of Formula (C) can be a substituted alkyl chain. Typical compounds falling within the general Formula (C) are shown in FIG. 14 as compound (D) (where n=3), compound (E) (where n=4), compound (F) (where n=5), compound (G) (where n=6), compound (H) (where n=7). For these compounds, $R_6$ is a sulphamate group of the formula —OS(O)(O)—$NH_2$ and each of $R_3$–$R_5$ is H. The term "sulphamate" includes an ester of sulphamic acid, or an ester of an N-substituted derivative of sulphamic acid, or a salt thereof. Thus, the term includes functional groups of the formula: —O—S(O)(O)—N($R_7$)($R_8$) where $R_7$ and $R_8$ are independently selected from H, halo, linear or branched alkyl which may be saturated or unsaturated and/or substituted or non-substituted, aryl, or any other suitable group. Preferably, at least one or $R_7$ and $R_8$ is H. In a preferred embodiment, each of $R_7$ and $R_8$ is H. See also WO 97/30041).

FIG. 15 shows the origin of oestrogenic steroids in postmenopausal women; "ER" denotes Oestrogen Receptor; "DHA/-S" denotes Dehydroepiandrosterone/-Sulfate; "DHA-STS" denotes DHA-sulphatase; "Adiol-STS" denotes Adiol Sulphatase; and "17B-HSD" denotes Oestradiol 17B-hyroxysteroid dehydrogenases).

FIGS. 16a, 16b, 16c, and FIGS. 17 to 23 depict chemical formulae (See Example 14 and WO 97/32872. In a preferred embodiment, the compounds comprise a first ring structure and a sulphamoyl group, which first ring structure may be substituted and/or unsaturated. The first ring structure is preferably a phenolic ring structure, which may be substituted. The compounds may further comprise a second ring structure, which may be substituted and/or unsaturated. The compounds may preferably be a sulphamate of a flavone, an isoflavone or a flavanone, or a sulphamate of a benzoflavone, e.g., FIG. 23 wherein R is H or OH; and, the invention also encompasses substituted variants of the sulphamate of the benzoflavone of FIG. 23. With regard to FIGS. 16a, 16b, 16c and 17 to 22, it is generally preferred that in formula I, A represents the first ring structure, B represents the third ring structure, D represents the second ring structure, C is an optional double bond, E is a link joining the second ring structure to the third ring structure, X represents a suitable first group, and Y represent a suitable second group, wherein any one of ring structures A, B, and D is a phenolic ring, and any one of ring structures A, B and D has bound thereto a sulphamate group. Each of the ring structures can independently comprise from 3 to 20 atoms in the ring, preferably 4 to 8 atoms in the ring; and, preferably ring A and ring D comprise 6 atoms in the ring. A further cyclic group may be linked to ring A or D. This cyclic group may be linked to two spaced-apart atoms in ring A or ring D, such as the structure shown in FIG. 23. Preferably the first ring structure and the second ring structure are substituted. Preferably any one of ring structures A and D has bound thereto a sulphamate group. Preferably, each of the first ring and the second ring is a homogeneous ring structure, i.e., the ring is made up of the same atoms. Preferably, each of the first ring and the second ring comprises only carbon atoms in the ring. Preferably X is C=O. Preferably the compound has the general formula II wherein F represents a phenolic ring structure (the first ring structure), J represents the third ring structure, I represents a phenolic ring structure (the second ring structure), G is an optional double bond, H is a link joining the second ring structure to the third ring structure, and Y represents a suitable second group, and any one of ring structures F, J and I has bound thereto a sulphamate group. Preferably the third ring structure is a heterogeneous ring structure, i.e., different atoms are in the ring. Preferably, Y is O. Preferably, any one of the ring structures F and I has bound thereto a sulphamate group. Preferably link E or link H is a bond. Preferably, the compound is a sulphamate of any one of a flavone, an isoflavone or a flavanone. Preferably, the compound is a compound of formula IV, V or VI, wherein $R_1$–$R_{12}$ are independently selected from H, OH, a halogen, an amine, an amide, a sulphonamine, a sulphonamide, any other sulphur containing group, a saturated or unsaturated $C_{1-10}$ alkyl, an aryl group, a saturated or unsaturated $C_{1-10}$ ether, a saturated or unsaturated $C_{1-10}$ ester, a phosphorus containing group, and wherein at least one of $R_1$–$R_{12}$ is a sulphamate group. Preferably the sulphamate group has the general formula $OSO_2NR_{13}R_{14}$ wherein $R_{13}$ and $R_{14}$ are independently selected from H, OH, a halogen, a saturated or unsaturated $C_{1-10}$ alkyl, an aryl group, a saturated or unsaturated $C_{1-10}$ ether, a saturated or unsaturated $C_{1-10}$ ester; and, each of $R_{13}$ and $R_{14}$ may be other suitable groups. Preferably the compound is a compound of formula IV, V or VI, wherein $R_1$–$R_{12}$ are independently selected from H, OH, $OSO_2NR_{13}R_{14}$, O—$CH_3$; wherein at least one of $R_1$–$R_{12}$ is $OSO_2NR_{13}R_{14}$ and $R_{13}$ and $R_{14}$ are as defined above. Preferably, at least one of $R_{13}$ and $R_{14}$ is H; and preferably each is H. Preferably, the compound is a sulphamate of any one of the flavone of formula VII, the isoflavone of formula VIII, or the flavanone of formula IX. Preferably the compound is a sulphamate of any of formulae VII, VIII or IX. Preferably the compound is a sulphamate of a flavone, isoflavone or flavanone wherein the sulphamoyl group is on the C4' atom of the flavone, isoflavone or flavanone. The C4' position is shown in formula III. Preferably, the compound is a flavonoid or flavanoid sulphamate. Preferably, if the sulphamate group of the compound were to be replaced with a sulphate group so as to form a sulphate compound then that sulphate compound would be hydrolysable by an enzyme having steroid sulphatase (E.C.3.1.6.2) activity. The compound may have one or more sulphamate groups. For example, the compound may be mono-sulphamate or a bis-sulphamate. For instance, in FIGS. 20–22, $R_3$ and $R_4$ may be each a sulphamate).

FIGS. 24 to 34 show compounds of the Formulae I to X, respectively (See Example 15 and WO 98/24802. With reference to FIGS. 25 to 34: In Formula I; A is a first group; B is an aryl ring structure having at least 4 carbon atoms in the ring and wherein the ring B is substituted in at least the 2 position and/or the 4 position with an atom or group other than H; X is a sulphamate group; wherein group A and ring B together are capable of mimicking the A and B rings of oestrone; and wherein group A is attached to at least one carbon atom in ring B. The term "mimic" as used herein means having a similar or different structure but having a similar functional effect. In other words, group A and ring B together of the compounds of the present invention are bio-isosteres of the A and B rings of oestrone. Preferably, the sulphamate group is at position 3 of the ring B. Preferably, the ring B has six carbon atoms in the ring. Preferably, the compound has the Formula II; wherein X is the sulphamate group; A is the first group; $R_1$ and/or $R_2$ is a substituent other than H; wherein $R_1$ and $R_2$ may be the same or different but not both being H; and wherein optionally group A is attached to at least one other carbon atom in ring B. Preferably, group A is additionally attached to the carbon atom at position 1 of the ring B. Preferably, group A and ring B are a steroid ring structure or a substituted derivative thereof. Preferably, the compound has the Formula IV; wherein X is the sulphamate group; $R_1$ and/or $R_2$ is a substituent other than H; wherein $R_1$ and $R_2$ may be the same or different but not both being H; and wherein Y is a suitable linking group. Suitable linking groups for Y include groups made up of at least any one or more of C, O, N, and S. The linking groups can also comprise H. The linking group may also increase the size of the ring (i.e. the D ring). Preferably, however, the D ring comprising Y is a five-membered ring. Preferably, Y is —$CH_2$— or —C(O)—, Preferably, Y is —C(O)—. Preferably, the compound has the Formula V; wherein X is the sulphamate group; $R_1$ and/or $R_2$ is a substituent other than H; and wherein $R_1$ and $R_2$ may be the same or different but not both being H. The term "sulphamate" as used herein includes an ester of sulphamic acid, or an ester of an N-substituted derivative of sulphamic acid, or a salt thereof. Preferably, the sulphamate group has the Formula III. In Formula III, each of $R_3$ and $R_4$ is independently selected from H or a hydrocarbyl group. The term "hydrocarbyl group" as used herein means a group comprising at least C and H and may optionally comprise one or more other suitable substituents. Examples of such substituents may include halo-, alkoxy-, nitro-, and alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group. In one preferred embodiment of the present invention, the hydrocarbyl group for the sulphamate group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch. Preferably, $R_3$ and $R_4$ are independently selected from H or alkyl, cycloalkyl, alkenyl and aryl, or together represent alkylene, wherein the or each alkyl or cycloalkyl or alkenyl or optionally contain one or more hetero atoms or groups. When substituted, the N-substituted compounds of this invention may contain one or two N-alkyl, N-alkenyl, N-cycloalkyl or N-aryl substituents, preferably containing or each containing a maximum of 10 carbon atoms. When $R_3$ and/or $R_4$ alkyl, the preferred values are those where $R_3$ and $R_4$ are each independently selected from lower alkyl groups containing from 1 to 5 carbon atoms, that is to say methyl, ethyl, propyl etc. Preferably $R_3$ and $R_4$ are both methyl. When $R_3$ and/or $R_4$ is aryl, typical values are phenyl and tolyl (–$PhCH_3$; o-, m- or p-). Where $R_3$ and $R_4$ represent cycloalkyl, typical values are cyclopropyl, cyclopentyl, cyclohexyl etc. When joined together $R_3$ and $R_4$ typically represent an alkylene group providing a chain of 4 to 6 carbon atoms, optionally interrupted by one or more hetero atoms or groups, e.g. —O— or —NH— to provide a 5-, 6- or 7-membered heterocycle, e.g. morpholino, pyrrolidino or piperidino. Within the values alkyl, cycloalkyl, alkenyl and aryl Applicants include substituted groups containing as substituents therein one or more groups which do not interfere with the sulphatase inhibitory activity of the compound in question. Exemplary non-interfering substituents include hydroxy, amino, halo, alkoxy, alkyl and aryl. In some preferred embodiments, at least one of $R_3$ and $R_4$ is H. In some further preferred embodiments, each of $R_3$ and $R_4$ is H. Preferably, each of $R_1$ and $R_2$ is independently selected from H, alkyl, cycloalkyl, alkenyl, aryl, substituted alkyl, substituted cycloalkyl, substituted alkenyl, substituted aryl, any other suitable hydrocarbyl group, a nitrogen containing group, a S containing group, a carboxy containing group. Likewise, here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group. Preferably, each of $R_1$ and $R_2$ is independently selected from H, $C_{1-6}$ alkyl, $C_{1-6}$ cycloalkyl, $C_{1-6}$ alkenyl, substituted $C_{1-6}$ alkyl, substituted $C_{1-6}$ cycloalkyl, substituted $C_{1-6}$ alkenyl, substituted aryl, a nitrogen containing group, a S containing group, or a carboxy group having from 1–6 carbon atoms. Likewise, here within the values alkyl, cycloalkyl, alkenyl and aryl Applicants include substituted groups containing as substituents therein one or more groups which do not interfere with the sulphatase inhibitory activity of the compound in question. Exemplary non-interfering substituents include hydroxy, amino, halo, alkoxy, alkyl and aryl. Preferably, each of $R_1$ and $R_2$ is independently selected from H, $C_{1-6}$ alkyl, $C_{1-6}$ alkenyl, a nitrogen containing group, or a carboxy group having from 1–6 carbon atoms. Preferably, each of $R_1$ and $R_2$ is independently selected from H, $C_{1-6}$ alkyl, $C_{1-6}$ alkenyl, $NO_2$, or a carboxy group having from 1–6 carbon atoms. Preferably, each of $R_1$ and $R_2$ is independently selected from H, $C_3$ alkyl, $C_3$ alkenyl, $NO_2$, or $H_3CHO$. Preferably, the compound is any one of the Formulae V–IX. Preferably, for some applications, the compound is further characterised by the feature that if the sulphamate group were to be substituted by a sulphate group to form a sulphate derivative, then the sulphate derivative would be hydrolysable by an enzyme having steroid sulphatase (E.C.3.1.6.2) activity—i.e. when incubated with steroid sulphatase EC 3.1.6.2 at pH 7.4 and 37° C. In one preferred embodiment, if the sulphamate group of the compound were to be replaced with a sulphate group to form a sulphate compound then that sulphate compound would be hydrolysable by an enzyme having steroid sulphatase (E.C.3.1.6.2) activity and would yield a $K_m$ value of less than 50 mmoles when incubated with steroid sulphatase EC3.1.6.2 at pH 7.4 and 37° C. In another preferred embodiment, if the sulphamate group of the compound were to be replaced with a sulphate group to form a sulphate compound then that sulphate compound would be hydrolysable by an enzyme having steroid sulphatase (E.C.3.1.6.2) activity and would yield a $K_m$ value of less than 50 $\mu$moles when incubated with steroid sulphatase EC3.1.6.2 at pH 7.4 and 37° C. In a highly preferred embodiment, the compound of the present invention is not hydrolysable by an enzyme having steroid sulphatase (E.C.3.1.6.2) activity. Preferably the group A and the ring B together—hereinafter referred to as "group A/ring B combination"—will contain, inclusive of all substituents, a maximum of about 50 carbon atoms, more usually no more than about 30 to 40 carbon atoms. A preferred group A/ring B combination has a steroidal ring structure, that is to say a cyclopentanophenanthrene skeleton in the 3-position. Thus, according to a preferred embodiment, the group A/ring B combination is a substituted or unsubstituted, saturated or unsaturated steroid nucleus. A suitable steroid nucleus is a substituted (i.e. substituted in at least the 2 and/or 4 position and optionally elsewhere in the steroid nucleus) derivative of any one of: oestrone, 2-OH-oestrone, 2-methoxy-oestrone, 4-OH-oestrone, 6a-OH-oestrone, 7a-OH-oestrone, 16a-OH-oestrone, 16b-OH-oestrone, oestradiol, 2-OH-17b-oestradiol, 2-methoxy-17b-oestradiol, 4-OH-17b-oestradiol, 6a-OH-17b-oestradiol, 7a-OH-17b-oestradiol, 16a-OH-17a-oestradiol, 16b-OH-17a-oestradiol, 16b-OH-17b-oestradiol, 17a-oestradiol, 17b-oestradiol, 17a-ethinyl-17b-oestradiol, oestriol, 2-OH-oestriol, 2-methoxy-oestriol, 4-OH-oestriol, 6a-OH-oestriol, 7a-OH-oestriol, dehydroepiandrosterone, 6a-O-dehydroepiandrosterone, 7a-OH-dehydroepiandrosterone, 16a-OH-dehydroepiandrosterone, 16b-OH-dehydroepiandrosterone. In general terms the group A/ring B combination may contain a variety of non-interfering substituents. In particular, the group A/ring B combination may contain one or more hydroxy, alkyl especially lower ($C_1$–$C_6$)alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc. alkenyl, e.g. ethenyl, or halogen, e.g. fluoro substituents. The group A/ring B combination may even be a non-steroidal ring system. A suitable non-steroidal ring system is a substituted (i.e. substituted in at least the 2 and/or 4 position and optionally elsewhere in the ring system) derivative of any one of: diethylstilboestrol, stilboestrol. When substituted, the N-substituted compounds of this invention may contain one or two N-alkyl, N-alkenyl, N-cycloalkyl or N-aryl substituents, preferably containing or each containing a maximum of 10 carbon atoms. When $R_1$ and/or $R_2$ and/or $R_3$ and/or $R_4$ is alkyl, the preferred values are those where each of $R_1$ and $R_2$ and $R_3$ and $R_4$ is independently selected from lower alkyl groups containing from 1 to 6 carbon atoms, that is to say methyl, ethyl, propyl etc. When $R_1$ and/or $R_2$ and/or $R_3$ and/or $R_4$ is aryl, typical groups are phenyl and tolyl (–PhCH$_3$; o-, m- or p-). Where $R_1$ and/or $R_2$ and/or $R_3$ and/or $R_4$ represent cycloalkyl, typical values are cyclopropyl, cyclopentyl, cyclohexyl etc. When joined together $R_3$ and $R_4$ typically represent an alkylene group providing a chain of 4 to 6 carbon atoms, optionally interrupted by one or more hetero atoms or groups, e.g. —O— or —NH— to provide a 5-, 6- or 7-membered heterocycle, e.g. morpholino, pyrrolidino or piperidino. Within the values alkyl, cycloalkyl, alkenyl and aryl we include substituted groups containing as substituents therein one or more groups which do not interfere with the sulphatase inhibitory activity of the compound in question. Examples of non-interfering substituents include hydroxy, amino, halo, alkoxy, alkyl and aryl. Applicants have also surprisingly found that when the compound has the Formula IV where Y=—CH$_2$— it is not necessary for the compound to be substituted in the 2 and 4 ring positions, i.e., $R_1$ and $R_2$ may both be hydrogen. In one embodiment of this aspect, any of the ring positions (including $R_1$ and $R_2$, but excluding Y) may be substituted. Thus, according to another aspect of the present invention there is provided a sulphamate compound of the Formula X and wherein X is a sulphamate group, and Y is CH$_2$ and optionally any other H attached directly to the ring system is substituted by another group. X may be as described above. Any replacement for H on the ring system may be any one of the substituents described above in relation to $R_1$ and $R_2$. In an especially preferred embodiment there is no substitution on the ring system, i.e., a compound of Formula IV where Y is —CH$_2$— and $R_1$ and $R_2$ are both H).

DETAILED DESCRIPTION

Figure 1:
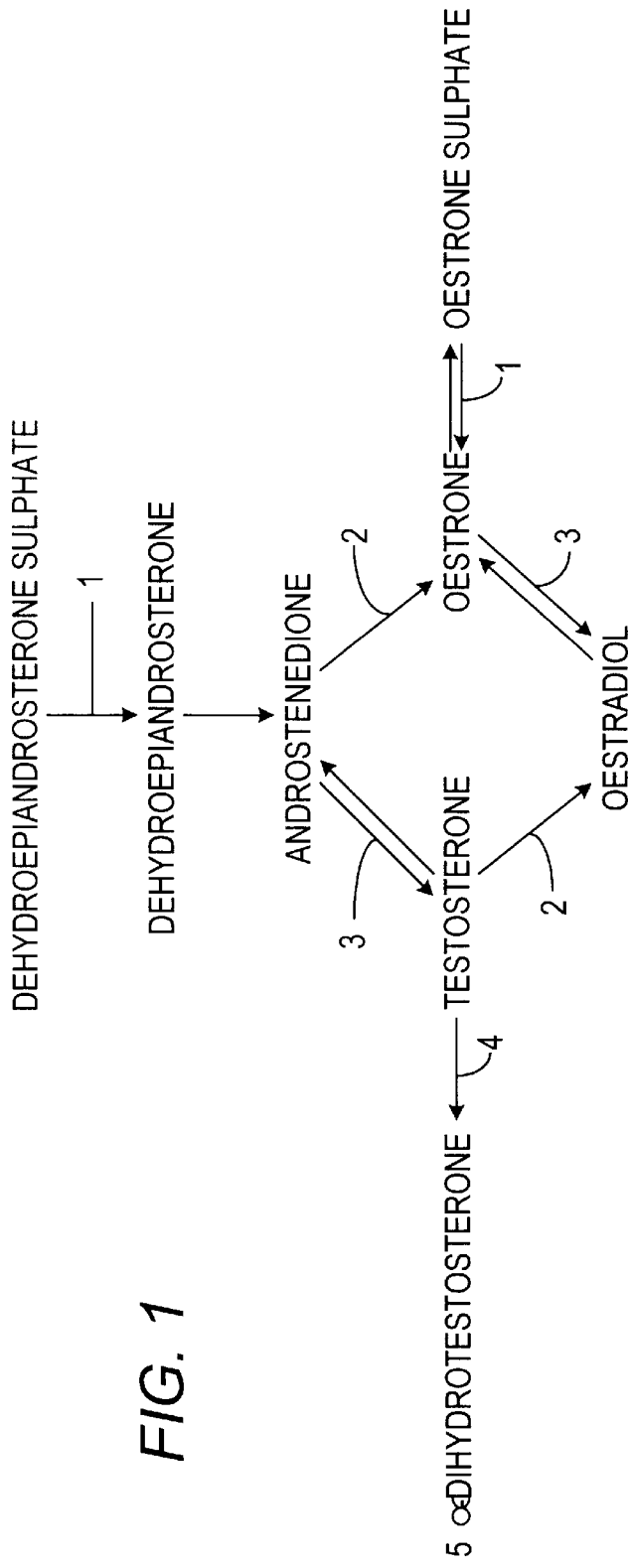
FIG. 1 is a schematic chart showing the metabolic pathways, enzymes and steroid intermediates associated with the production of oestradiol in vivo.

Thus, in one aspect, the present invention provides a method of inhibiting steroid sulphatase activity in a subject in need of same, the method comprising administering to said subject a steroid sulphatase inhibiting amount of a ring system compound; which ring system compound comprises a ring to which is attached a sulphamate group of the formula

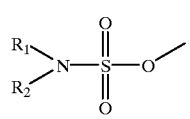

wherein each of $R_1$ and $R_2$ is independently selected from H, alkyl, alkenyl, cycloalkyl and aryl, or together represent alkylene optionally containing one or more hetero atoms or groups in the alkylene chain; and wherein said compound is an inhibitor of an enzyme having steroid sulphatase activity (E.C.3.1.6.2); and if the sulphamate group of said compound is replaced with a sulphate group to form a sulphate compound and incubated with a steroid sulphatase enzyme (E.C.3.1.6.2) at a pH 7.4 and 37° C. it would provide a $K_m$ value of less than 50 µM.

In one aspect the present invention provides, a novel compounds, the sulphamic acid esters of polycyclic alcohols, being polycyclic alcohols the sulphate of which is a substrate for enzymes having steroid sulphatase activity in accordance with the definition already provided, and their N-alkyl, N-cycloalkyl, N-alkenyl and N-aryl derivatives. These compounds are of Formula I hereinbefore given.

Preferably the polycyclic group will contain, inclusive of all substituents, a maximum of about 40 carbon atoms, more usually no more than about 30.

Preferred polycycles are those containing a steroidal ring structure, that is to say a cyclopentanophenanthrene skeleton. Preferably, the sulphamyl or substituted sulphamyl group is attached to that skeleton in the 3-position, that is to say are compounds of the Formula II:

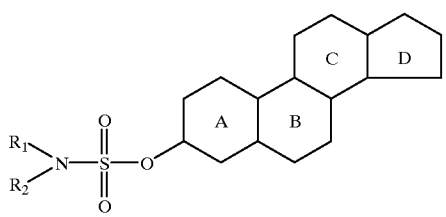

FORMULA (II)

where $R_1$ and $R_2$ are as above defined and the ring system ABCD represents a substituted or unsubstituted, saturated or unsaturated steroid nucleus, preferably oestrone or dehydroepiandrosterone.

Other suitable steroid ring systems are:
substituted oestrones, viz:

| | | | |
|---|---|---|---|
| 2-OH-oestrone | 2-methoxy-oestrone | 4-OH-oestrone | 6α-OH-strone |
| 7α-OH-oestrone | 16α-OH-oestrone | 16β-OH-oestrone | | oestradiols and substituted oestradiols, viz:

| | | |
|---|---|---|
| 2-OH-17β-oestradiol | 2-methoxy-17β-oestradiol | 4-OH-17β-oestradiol |
| 6α-OH-17β-oestradiol | 7α-OH-17β-oestradiol | 16α-OH-17α-oestradiol |
| 16β-OH-17α-oestradiol | 16β-OH-17β-oestradiol | 17α-oestradiol |
| 17β-oestradiol | 17α-ethinyl-17β-oestradiol | | oestriols and substituted oestriols, viz:

| | | |
|---|---|---|
| oestriol | 2-OH-oestriol | 2-methoxy-oestriol |
| 4-OH-oestriol | 6α-OH-oestriol | 7α-OH-oestriol | substituted dehydroepiandrosterones, viz:

| | |
|---|---|
| 6α-OH-dehydroepiandrosterone | 7α-OH-dehydroepiandrosterone |
| 16α-OH-dehydroepiandrosterone | 16β-OH-dehydroepiandrosterone |

In general terms the steroid ring system ABCD may contain a variety of non-interfering substituents. In particular, the ring system ABCD may contain one or more hydroxy, alkyl especially lower ($C_1$–$C_6$)alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., alkinyl, e.g. ethinyl, or halogen, e.g. fluoro substituents.

Suitable non-steroidal ring systems (i.e. ring system compounds) include:

diethylstilboestrol, stilboestrol and other ring systems providing sulfates having $K_m$ values of less than 50 µmoles with steroid sulphatase EC3.1.6.2.

Examples of some non-steroidal ring systems are presented in the Examples section.

When substituted, the N-substituted compounds of this invention may contain one or two N-alkyl, N-alkenyl, N-cycloalkyl or N-aryl substituents, preferably containing or each containing a maximum of 10 carbon atoms. When $R_1$ and/or $R_2$ is alkyl, the preferred values are those where $R_1$ and $R_2$ are each independently selected from lower alkyl groups containing from 1 to 5 carbon atoms, that is to say methyl, ethyl, propyl etc. Preferably $R_1$ and $R_2$ are both methyl. When $R_1$ and/or $R_2$ is aryl, typical values are phenyl and tolyl (—PhCH$_3$; o-, m- or p-). Where $R_1$ and $R_2$ represent cycloalkyl, typical values are cyclopropyl, cyclopentyl, cyclohexyl etc. When joined together $R_1$ and $R_2$ typically represent an alkylene group providing a chain of 4 to 6 carbon atoms, optionally interrupted by one or more hetero atoms or groups, e.g. —O— or —NH— to provide a 5-,6- or 7)-membered heterocycle, e.g. morpholine pyrrolidino or piperidino.

Within the values alkyl, cycloalkyl, alkenyl and aryl we include substituted groups containing as substituents therein one or more groups which do not interfere with the sulphatase inhibitory activity of the compound in question. Exemplary non-interfering substituents include hydroxy, amino, halo, alkoxy, alkyl and aryl.

Most preferred are compound of the Formula III and IV:

FORMULA (III)

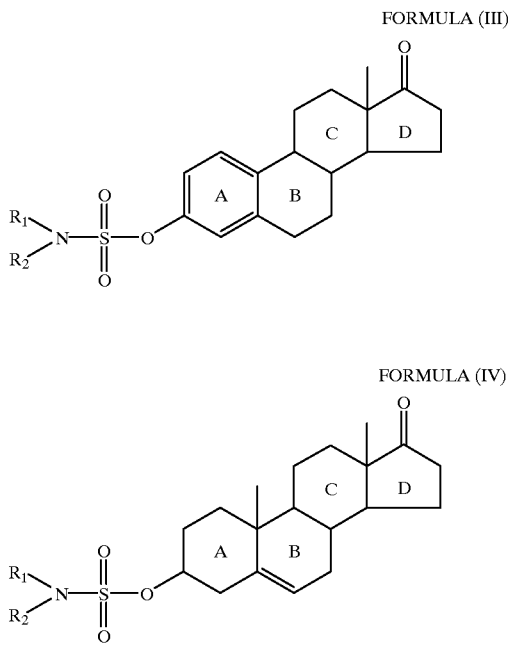

FORMULA (IV)

where $R_1$ and $R_2$ are H or $C_1$–$C_5$ alkyl, i.e. oestrone-3-sulphamate and dehydroepiandrosterone-3-sulphamate and their N—($C_1$–$C_5$) alkyl derivatives, especially the dimethyl derivatives, $R_1=R_2=CH_3$.

The sulphamic acid esters of this invention are prepared by reacting the polycyclic alcohol, e.g. oestrone or dehydroepiandrosterone, with a sulfamoyl chloride $R_1R_2NSO_2Cl$, i.e. the Reaction Scheme I

REACTION SCHEME I

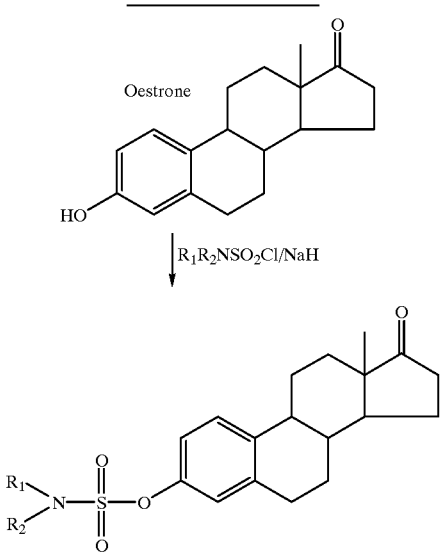

Conditions for carrying out Reaction Scheme I are as follows:

Sodium hydride and a sulphamoyl chloride are added to a stirred solution of oestrone in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporation with toluene affords a crude residue which is further purified by flash chromatography.

Where necessary, functional groups in the polycyclic alcohol (sterol) may be protected in known manner and the protecting group or groups removed at the end of the reaction.

For pharmaceutical administration, the steroid sulphatase inhibitors of this invention can be formulated in any suitable manner utilising conventional pharmaceutical formulating techniques and pharmaceutical carriers, exipients, diluents etc. and usually for parenteral administration. Approximate effective dose rates are in the range 100 to 800 mg/day depending on the individual activities of the compounds in question and for a patient of average (70 kg) bodyweight. More usual dosage rate for the preferred and more active compound will be in the range 200 to 800 mg/day, more preferably, 200 to 500 mg/day, most preferably from 200 to 250 mg/day. They may be given in single dose regimes, split does regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration is a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

For particular applications, it is envisaged that the steroid sulphatase inhibitors of this invention may be used in combination therapies, either with another sulphatase inhibitor, or, for example, in combination with an aromatase inhibitor, such as for example, 4-hydroxyandrostenedione (4-OHA).

The invention is illustrated by the following preparative Examples and test data:

Example 1

Preparation of oestrone-3-sulphamate

Sodium hydride (60% dispersion; 2 eq) and sulphamoyl chloride (2 eq) were added to a stirred solution of oestrone (1 eq) in anhydrous dimethyl formamide at 0° C. Subsequently, the reaction was allowed to warm to room temperature whereupon stirring was continued for a further 24 hours.

The reaction mixture was poured onto a cold saturated solution of sodium bicarbonate and the resulting aqueous phase was extracted with dichloromethane. The combined organic extracts were dried over anhydrous $MgSO_4$. Filtration followed solvent evaporation in vacuo and co-evaporation with toluene afforded a crude residue which is further purified by flash chromatography.

Analysis showed the following data:

$\delta^1H$(270 MHz; $CD_3OD$): 0.91 (s, 3H, $C_{18}$—Me), 1.40–2.55 (series of m, 13H), 2.90–2.92 (m, 2H), 7.04 (br d, 2H, J=10.44 Hz), 7.33 (br d, 1H, J=8.42 Hz). $\delta^{13}C$(67.8 MHz; $CD_3OD$): 14.53 (q, $C_{18}$—Me), 22.80 (t), 27.24 (t), 27.73 (t), 30.68 (t), 33.05 (t), 37.01 (t), 39.76 (d), 45.73 (s, $C_{18}$), 51.86 (d), 120.76 (d), 123.54 (d), 127.89 (d), 139.83

(s), 150.27 (s), 223.87 (s, C=O). m/z (%): 349 (9) (m$^+$), 270 (100), 213 (26), 185 (43), 172 (31), 159 (21), 146 (36), 91 (33), 69 (37), 57 (73), 43 (56), 29 (24).

Microanalysis:

|  | C | H | N |
|---|---|---|---|
| Expected: | 61.87% | 6.63% | 4.01% |
| Found: | 61.90% | 6.58% | 3.95% |

Example 2

Preparation of oestrone-3-N-methylsulphamate

The procedure of Example 1 was repeated save that sulphamoyl chloride was replaced by the same quantity of N-methylsulphamoyl chloride.

Analysis showed the following data:

$\delta^1$(270 MHz; CDCl$_3$): 0.91 (s, 3H, C$_{18}$—Me), 1.28–1.68 (m, 6H), 1.93–2.60 (series of m, 7H), 2.90–2.95 (m, 2H), 2.94 (d, 3H, J=5.13 Hz, MeN—), 4.68–4.71 (br m, exchangeable, 1H, —NH), 7.02–7.07 (m, 2H), 7.26–7.32 (m, 1H). m/z (%): 364 [M+H]$^+$

Example 3

Preparation of oestrone-3-N,N-dimethylsulphamate

The procedure of Example 1 was repeated save that sulphamoyl chloride was replaced by the same quantity of N,N-dimethylsulphamoyl chloride.

Analysis showed the following data:

$\delta^1$H(270 MHz; CDCl$_3$): 0.92 (s, 3H, C$_{18}$—Me), 1.39–1.75 (m, 5H), 1.95–2.60 (series of m, 6H), 2.82 (s, 3H, MeN—), 2.96–3.00 (m, 4H), 2.98 (s, 3H, MeN—), 7.04 (br d, 2H, J=7.69 Hz), 7.29 (br d, 1H, J=7.88 Hz). m/z (%): 377 [M]$^+$ Microanalysis:

|  | C | H | N |
|---|---|---|---|
| Expected: | 63.63% | 7.21% | 3.71% |
| Found: | 63.59% | 7.23% | 3.60% |

Example 4

Inhibition of Steroid Sulphatase Activity in MCF-7 Cells by oestrone-3-sulphamate Steroid sulphatase is defined as: Steryl Sulphatase EC 3.1.6.2.

Steroid sulphatase activity was measured in vitro using intact MCF-7 human breast cancer cells. This hormone dependent cell line is widely used to study the control of human breast cancer cell growth. It possesses significant steroid sulphatase activity (MacIndoe et al. *Endocrinology*, 123, 1281–1287 (1988); Purohit & Reed, *Int. J. Cancer*, 50, 901–905 (1992)) and is available in the U.S.A. from the American Type Culture Collection (ATCC) and in the U.K. (e.g. from The Imperial Cancer Research Fund). Cells were maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm$^2$ tissue culture flasks were seeded with approximately 1×10$^5$ cells/flask using the above medium. Cells were grown to 80% confluency and medium was changed every third day.

Intact monolayers of MCF-7 cells in triplicate 25 cm$^2$ tissue culture flasks were washed with Earle's Balanced Salt Solution (EBSS from ICN Flow, High Wycombe, U.K.) and incubated for 3–4 hours at 37° C. with 5 pmol (7×10$^5$ dpm) [6,7-$^3$H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 μm: 0.1 μM; 1 μM). After incubation each flask was cooled and the medium (1 ml) was pipetted into separate tubes containing [$^{14}$C] oestrone (7×10$^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$C] oestrone and <0.1% [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C]oestrone added) and the specific activity of the substrate. Each batch of experiments included incubations of microsomes prepared from a sulphase-positive human placenta (positive control) and flasks without cells (to assess apparent non-enzymatic hydrolysis of the substrate). The number of cell nuclei per flask was determined using a Coulter Counter after treating the cell monolayers with Zaponin. One flask in each batch was used to asses cell membrane status and viability using the Trypan Blue exclusion method (Phillips, H. J. (1973) In: *Tissue culture and applications*, [eds: Kruse, D. F. & Patterson, M. K.]; pp. 406–408; Academic Press, New York).

Figure 2:
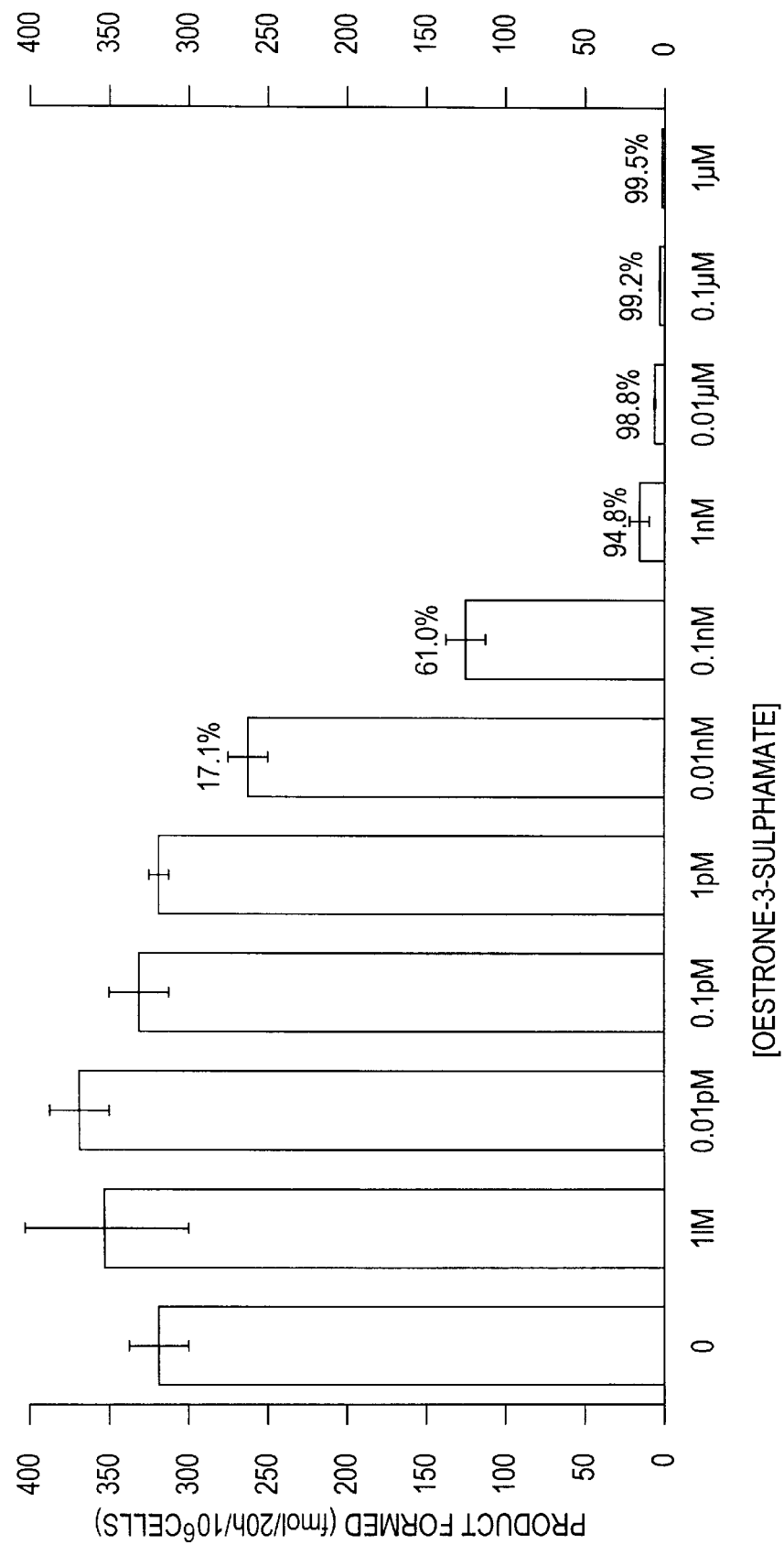
FIG. 2 is a histogram showing the dose-dependent inhibitory effect of oestrone-3-sulphamate on steroid sulphatase activity in human MCF-7 cells in vitro.
Figure 4:
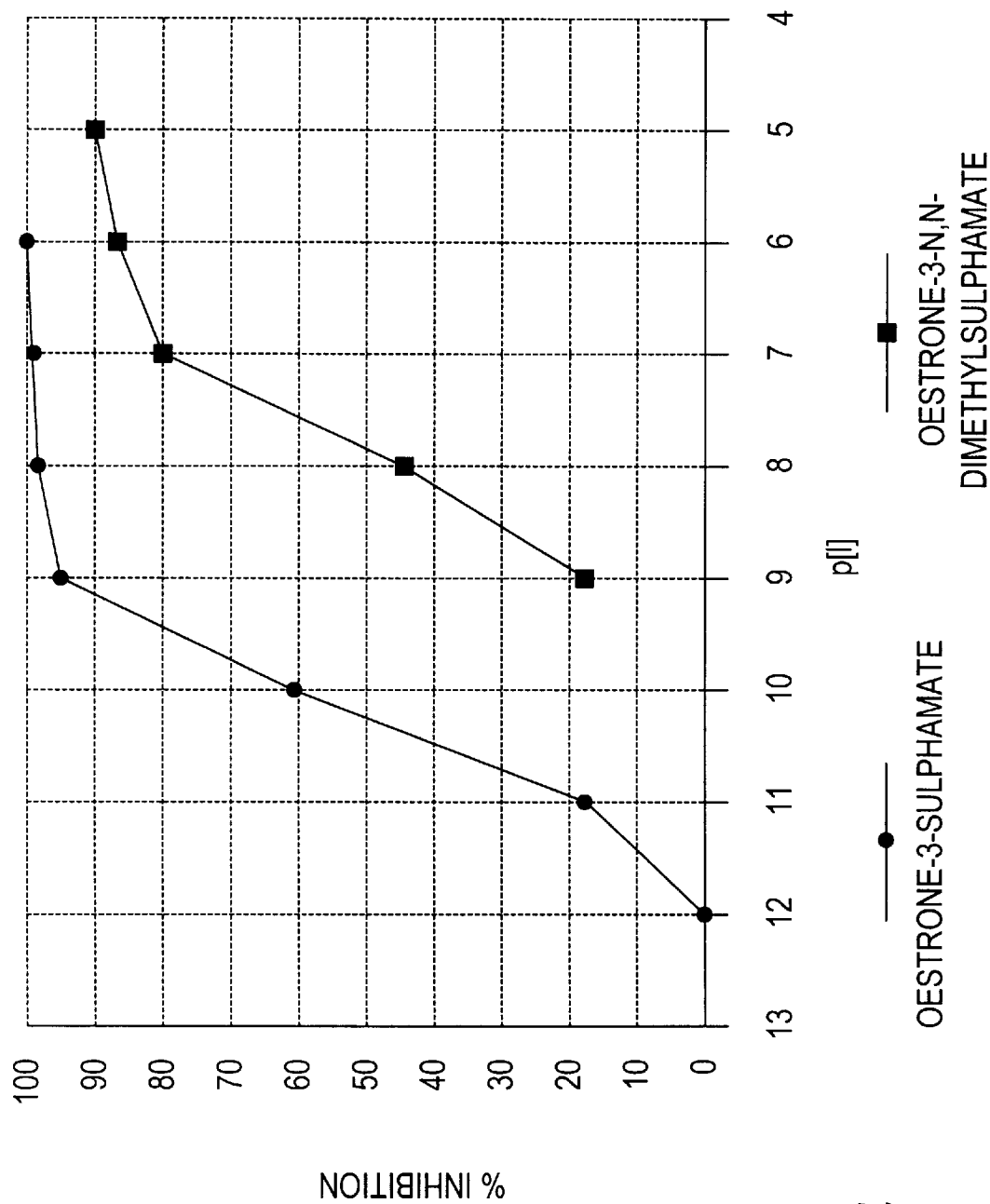
FIG. 4 is a graph comparing the log dose-response curves for oestrone-3-sulphamate and oestrone-3-N,N-dimethylsulphamate on steroid sulphatase activity in human MCF-7 cells in vitro.

Data for oestrone-3-sulphamate are shown in Table I and FIGS. 2 and 4. Results for steroid sulphatase activity are expressed as the mean ±1 S.D. of the total product (oestrone+oestradiol) formed during the incubation period (20 hours) calculated for 10$^6$ cells and, for values showing statistical significance, as a percentage reduction (inhibition) over incubations containing no oestrone-3-sulphamate. Unpaired Student's t-test was used to test the statistical significance of results.

TABLE I

Steroid Sulphatase Activity in MCF-7 cells in the presence of Oestrone-3-sulphamate

| Oestrone-3-sulphamate concentration | Steroid Sulphatase Activity ¶ (fmol/20 hr/10$^6$ cells) | % reduction over control (% inhibition) |
|---|---|---|
| 0 (control) | 319.7 ± 18.5 | — |
| 1 fM | 353.3 ± 39.0 | — |
| 0.01 pM | 362.3 ± 21.2 | — |
| 0.1 pM | 330.7 ± 17.8 | — |
| 1 pM | 321.8 ± 6.2 | — |
| 0.01 nM | 265.1 ± 11.0* | 17.2% |
| 0.1 nM | 124.8 ± 12.4*** | 60.9% |
| 1 nM | 16.49 ± 4.7*** | 95.0% |
| 0.01 μM | 3.92 ± 0.4*** | 98.8% |
| 0.1 μM | 2.53 ± 1.1*** | 99.2% |
| 1 μM | 1.68 ± 0.7*** | 99.5% |

¶ mean ± 1 S.D. n = 3
*p ≦ 0.05
***p ≦ 0.001

Example 5

Inhibition of Steroid Sulphatase Activity in MCF-7 cells by oestrone-3-N,N-dimethylsulphamate An identical experimental protocol to that described in Example 4 was used to generate results for oestrone-3-N, N-dimethylsulphamate except that incubations contained oestrone-3-N,N-dimethylsulphamate (5 concentrations: 0; 0.001 µM; 0.01 µM; 0.1 µM; 1 µM) in place of oestrone-3-sulphamate.

Figure 3:
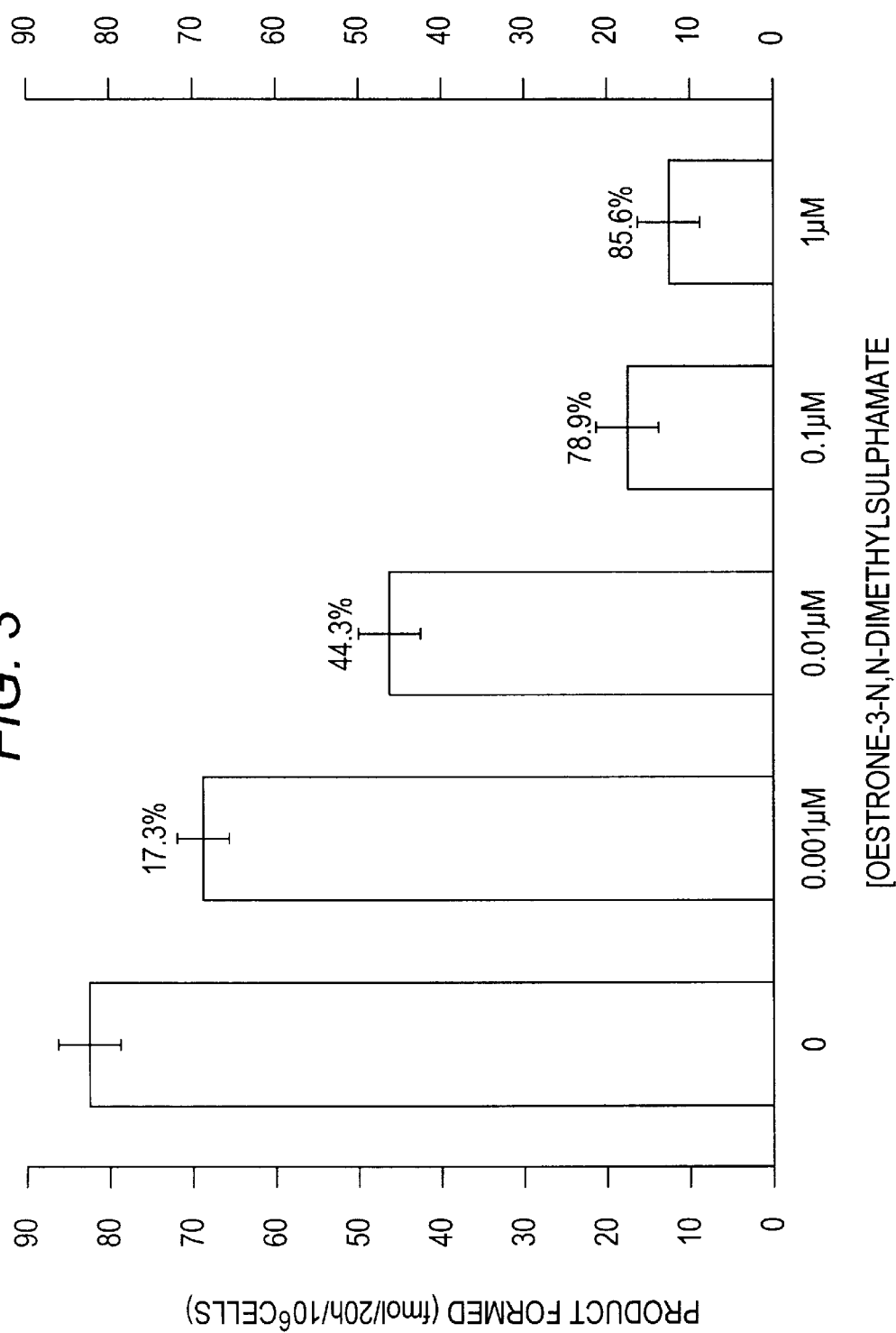
FIG. 3 is a histogram showing the dose-dependent inhibitory effect of oestrone-3-N,N-dimethylsulphamate on steroid sulphatase activity in human MCF-7 cells in vitro.

Results for oestrone-3-N,N-dimethylsulphamate are shown in Table II and FIG. 3 and are expressed in an identical manner to Table I and FIG. 2 respectively. Additionally the log dose-response curve is compared with oestrone-3-sulphamate in FIG. 4.

TABLE II

Steroid Sulphatase Activity in MCF-7 cells in the presence of Oestrone-3-N,N-dimethylsulphamate

| Oestrone-3-N,N-dimethylsulphamate concentration | Steroid Sulphatase Activity ¶ (fmol/20 hr/10⁶ cells) | % reduction over control (% inhibition) |
|---|---|---|
| 0 (control) | 82.63 ± 3.6 | — |
| 0.001 µM | 68.33 ± 3.2** | 17.3% |
| 0.01 µM | 46.0 ± 4.9*** | 44.3% |
| 0.1 µM | 17.43 ± 4.3*** | 78.9% |
| 1 µM | 11.89 ± 3.7*** | 85.6% |

¶ mean ± S.D. n = 3
**p ≤ 0.01
***p ≤ 0.001

Example 6

Inhibition of Steroid Sulphatase Activity in MCF-7 cells by pre-treatment with oestrone-3-N,N-dimethylsulphamate and oestrone-3-N,N-dimethylsulphamate A similar experimental protocol to that described in Example 4 was used to determine the effect of pre-treating MCF-7 cells with oestrone-3-sulphamate and oestrone-3-N, N-dimethylsulphamate respectively.

Intact monolayers were initially incubated for 2 hours at 37° C. with 0.1 µM oestrone-3-sulphamate, oestrone-3-N, N-dimethylsulphamate or medium alone (control). The medium bathing the cells was then removed by aspiration and cells were washed 3 times successively with 5 ml of medium on each occasion. The resultant 'washed' cells were then re-suspended and incubated for 3–4 hours at 37° C. in medium containing 5 pmol (7×10⁵ dpm) [6,7-³H]oestrone-3-sulphate. All other aspects were identical to those described in Examples 3 and 4.

Results for oestrone-3-sulphamate and oestrone-3-N,N-dimethylsulphamate are shown in Table III and are expressed in a similar manner to Table I.

TABLE III

Steroid Sulphatase Activity in MCF-7 cells pre-incubated with Oestrone-3-sulphamates

| Pre-treatment | Steroid Sulphatase Activity ¶ (fmol/20 hr/10⁶ cells) | % reduction over control (% inhibition) |
|---|---|---|
| Control | 65.4 ± 6.4 | — |
| Oestrone-3-sulphamate | 1.7 ± 0.2*** | 97.4% |
| Oestrone-3-N,N-dimethylsulphamate | 53.1 ± 3.4* | 18.8% |

¶ mean ± 1 S.D. n = 3
*p ≤ 0.05
***p ≤ 0.001

Example 7

Inhibition of Steroid Sulphatase Activity in Placental Microsomes by Oestrone-3-sulphamate Sulphatase-positive human placenta from normal term pregnancies (Obstetric Ward, St. Mary's Hospital, London) were thoroughly minced with scissors and washed once with cold phosphate buffer (pH 7.4, 50 mM) then re-suspended in cold phosphate buffer (5 ml/g tissue). Homogenisation was accomplished with an Ultra-Turrax homogeniser, using three 10 second bursts separated by 2 minute cooling periods in ice. Nuclei and cell debris were removed by centrifuging (4° C.) at 2000 g for 30 minutes and portions (2 ml) of the supernatant were stored at −20° C. The protein concentration of the supernatants was determined by the method of Branford (Anal. Biochem., 72, 248–254 (1976)).

Incubations (1 ml) were carried out using a protein concentration of 100 µg/ml, substrate concentration of 20 µM [6,7-³H]oestrone-3-sulphate (specific activity 60 Ci/mmol from New England Nuclear, Boston Mass., U.S.A.) and an incubation time of 20 minutes at 37° C. Eight concentrations of oestrone-3-sulphamate were employed: 0 (i.e. control); 0.05 µM; 0.1 µM; 0.2 µM; 0.4 µM; 0.6 µM; 0.8 µM; 1.0 µM. After incubation each sample was cooled and the medium (1 ml) was pipetted into separate tubes containing [¹⁴C]oestrone (7×10³ dpm) specific activity 97 Ci/mmol from Amersham International Radiochemical Centre, Amersham, U.K.). The mixture was shaken thoroughly for 30 seconds with toluene (5 ml). Experiments showed that >90% [¹⁴C]oestrone and <0.1% [³H]oestrone-3-sulphate was removed from the aqueous phase by this treatment. A portion (2 ml) of the organic phase was removed, evaporated and the ³H and ¹⁴C content of the residue determined by scintillation spectrometry. The mass of oestrone-3-sulphate hydrolysed was calculated from the ³H counts obtained (corrected for the volumes of the medium and organic phase used, and for recovery of [¹⁴C]oestrone added) and the specific activity of the substrate.

Figure 5:
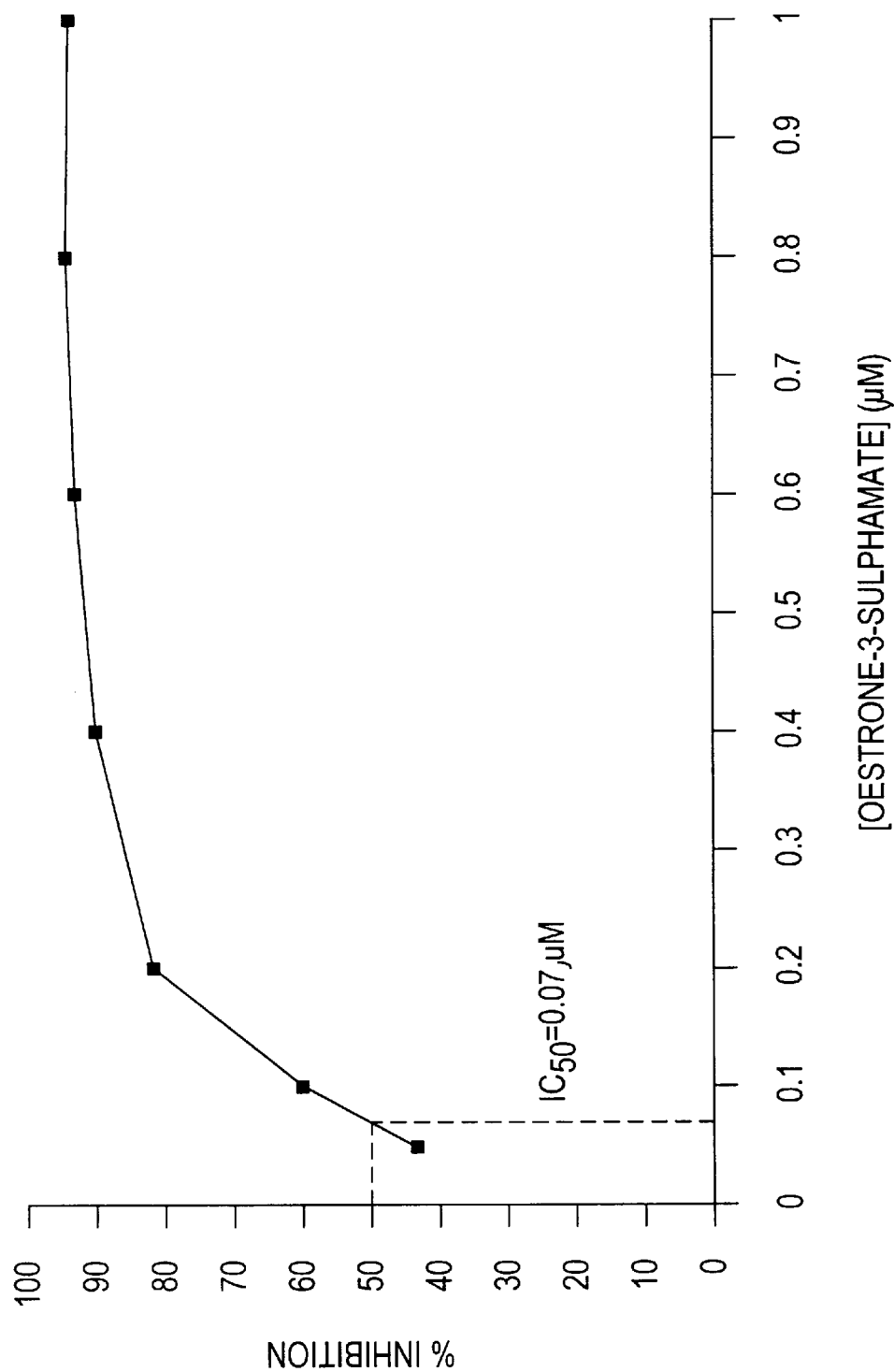
FIG. 5 is a graph showing the dose-dependent inhibitory effect of oestrone-3-sulphamate, together with its $IC_{50}$ value (concentration required to produce 50% inhibition), on steroid sulphatase activity in human placental microsomes in vitro.
Figure 6:
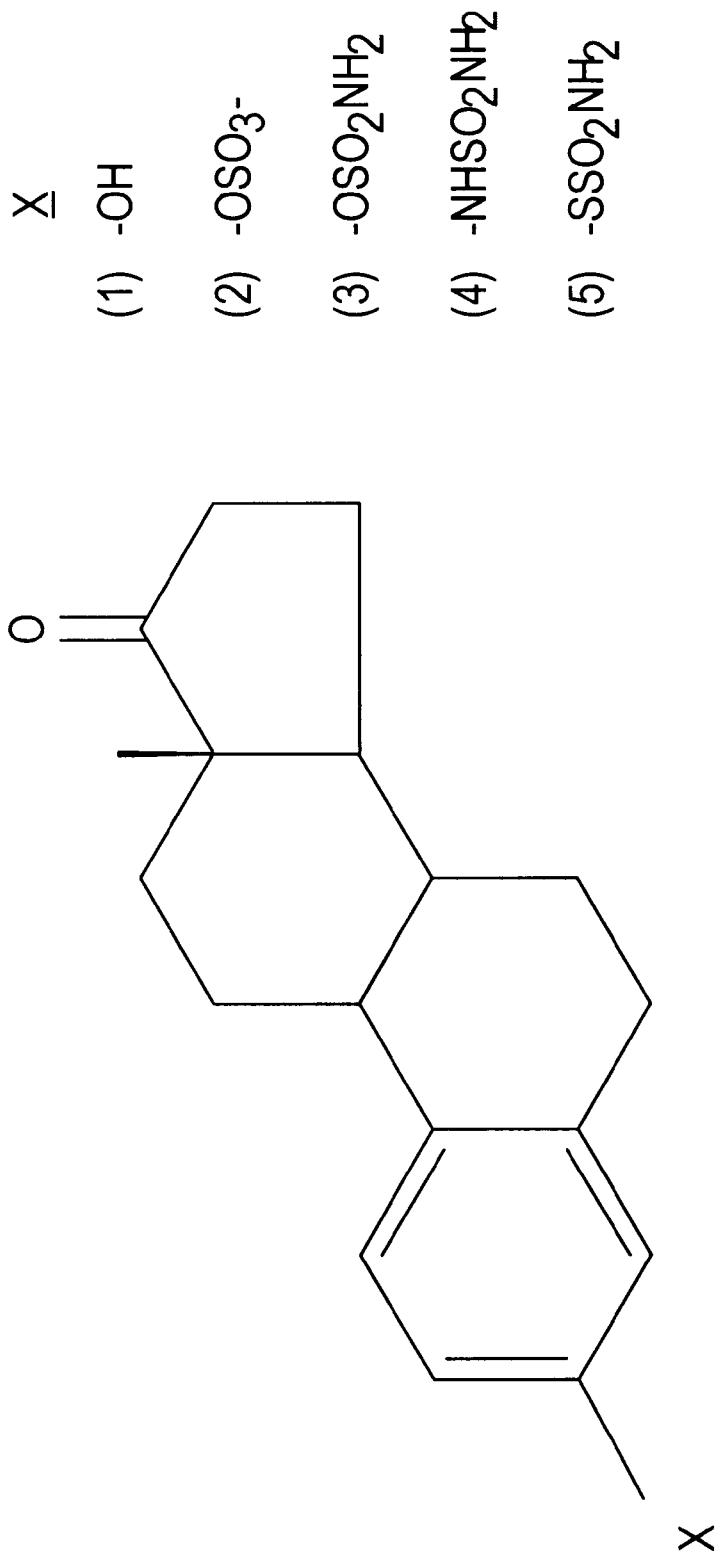
FIG. 6 shows the structures of oestrone (1), oestrone sulphate (2), oestrone-3-sulphamate (otherwise known as "EMATE") (3) and steroid sulphamates (4–5) (See Example 13 and WO 97/30041).

Results for oestrone-3-sulphamate are shown in Table IV and FIG. 5. Results for steroid sulphatase activity are expressed in Table IV as total product (oestrone+oestradiol) formed during the incubation period (time) and as a percentage reduction (inhibition) over incubations containing no oestrone-3-sulphamate which acted as control. Results for steroid sulphatase activity are expressed in FIG. 4 as percentage reduction (inhibition) over control against concentration of oestrone-3-sulphamate and include the calculated IC$_{50}$ value (i.e. the concentration of oestrone-3-sulphamate which produces 50% inhibition in relation to control) of 0.07 µM.

TABLE IV

Steroid Sulphatase Activity in placental microsomes in the presence of Oestrone-3-sulphmate

| Oestrone-3-sulphamate concentration | Steroid Sulphatase Activity ¶ (pmol/hr/0.1 mg protein) | % reduction over control (% inhibition) |
|---|---|---|
| 0 (control) | 768.6 | — |
| 0.05 µM | 430.4 | 44.0% |
| 0.1 µM | 305.9 | 60.2% |
| 0.2 µM | 140.0 | 81.8% |
| 0.4 µM | 83.3 | 89.2% |
| 0.6 µM | 61.8 | 92.0% |
| 0.8 µM | 49.2 | 93.6% |
| 1.0 µM | 51.6 | 93.3% |

¶ mean of 2 estimates

Example 8

Inhibition of Steroid Sulphatase Activity in Liver Microsome Preparations from Rats Treated with Subcutaneous Oestrone-3-sulphamate Four groups of 3 female Wistar rats (weight range 80–110 g) were given 100 ml subcutaneous injections (once daily for 7 days, vehicle: propylene glycol) of either:

Propylene glycol (vehicle control)

Oestrone-3-sulphamate (10 mg/kg/day)

Oestrone-3-sulphate (10 mg/kg/day) substrate control

Oestrone-3-sulphate (10 mg/kg/day)+Oestrone-3-sulphamate (10 mg/kg/day)

On the eighth day all rats were sacrificed and livers were removed by dissection. Liver microsomal preparations were prepared by an identical protocol to that described in Example 6 except that the tissue source was rat liver and that duplicate experiments to determine steroid sulphatase activity were performed using [6,7-$^3$H]oestrone-3-sulphate and [7-$^3$H]dehydroepiandrosterone-3-sulphate as separate substrates.

Results for steroid sulphatase activity are shown in Table V and are expressed as total product formed during the incubation period in the form of mean ±1 S.D. Results for incubations of tissue obtained from groups of rats treated with oestrone-3-sulphamate are also expressed as a percentage reduction (inhibition) in steroid sulphatase activity compared to their respective controls.

TABLE V

Steroid Sulphatase Activity in Liver Microsome Preparations from Rats treated with subcutaneous Oestrone-3-sulphamate

| Treatment Group | Assay Substrate | Steroid Sulphatase Activity ¶ (nmol/30 min/200 mg protein) | % reduction over control |
|---|---|---|---|
| control (vehicle) | $E_1$-S | 20.95 ± 0.2 | — |
| $E_1$-$SO_3NH_2$ | $E_1$-S | 0.34 ± 0.1*** | 98.4% |
| control ($E_1$-S) | $E_1$-S | 20.6 ± 0.4 | — |
| $E_1$-S + $E_1$-$SO_3NH_2$ | $E_1$-S | 0.21 ± 0.03*** | 99.0% |
| control (vehicle) | DHA-S | 1.73 ± 0.4 | — |
| $E_1$-$SO_3NH_2$ | DHA-S | 0.1 ± 0.01*** | 94.2% |
| control ($E_1$-S) | DHA-S | 1.71 ± 0.1 | — |
| $E_1$-S + $E_1$-$SO_3NH_2$ | DHA-S | 0.09 ± 0.01*** | 94.7% |

¶ mean ± S.D. n = 3
*** ≦0.001
$E_1$-S = oestrone-3-sulphamate
DHA-S = dehydroepiandrosterone-3-sulphate
$E_1$-$SO_3NH_2$ = oestrone-3-N,N-dimethylsulphamate Example 9

Starting with the appropriate parent compound, the ring system sulphamates according to the present invention were prepared essentially as follows. In this regard, a solution of the appropriate parent compound in anhydrous DMF was treated with sodium hydride [60% dispersion; 1.2 equiv.]at 0° C. under an atmosphere of $N_2$. After evolution of hydrogen had ceased, sulfamoyl chloride in toluene [excess, ca. 5 equiv.] was added and the reaction mixture was poured into brine after warming to room temperature overnight and diluting with ethyl acetate. The organic fraction was washed exhaustively with brine, dried ($MgSO_4$), filtered and evaporated. The crude product obtained was purified by flash chromatography and recrystallisation to give the corresponding sulfamate. All the compounds were fully characterized by spectroscopic and combustion analysis.

Example compounds are as follows:

Example 9a 4-n-Heptyl phenyl-O-sulphamate (9a)

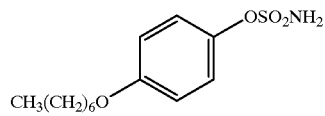

[9a]

4-n-Heptyloxyphenol (1.0 g, 4.80 mmol) gave a crude product (1.41 g) which was fractionated on silica (200 g) with chloroform/acetone (8:1), and upon evaporation the second fraction gave a pale white residue (757 mg) which was recrystallized from acetone/hexane (1:5) to give 9a as white crystals (0.557 g).

Analytical results were as follows:

m.p.>42° C. (dec.)

$R_f$s=0.56, 0.69 and 0.8 for chloroform/acetone 8:1, 4:1 and 2:1 respectively

νmax (KBr) 3440, 3320 (—$NH_2$), 1370 (—$SO_2N$—) cm$^{-1}$ $\delta_H$ (acetone-$d_6$) (270 MHz) 0.89 (3H, t, C—4—$CH_3$), 1.34 (8H, m, —($CH_2$)$_4CH_3$), 1.79 (2H, pentet, =C$\underline{H_2}$($CH_2$)$_4CH_3$), 4.0 ($\overline{2H}$, t, J=6.4 Hz, —O$\underline{CH_2}$—), 6.95 (2H, dd, $J_{C-3-H\ and\ C-5-H}$=2.2 Hz and $J_{C-3-H\ and\ C-2-H}$=6.97 Hz, C—3—$\underline{H}$ and C—5—$\underline{H}$), 7.01 (2H, br s, exchanged with $D_2O$, —$OSO_2NH_2$), 7.23 (2H, dd, $J_{C-2-H\ and\ C-6-H}$=2.4 Hz and $J_{C-2-H\ and\ C-6-H}$=6.97 Hz, C—2—$\underline{H}$ and C—6—$\underline{H}$)

MS: m/z (+ve ion FAB in m-NBA, rel. intensity) 287.1 [100, (M)$^+$], 208.2 [30, (M—$SO_2NH_2$)$^+$] MS: m/z (–ve ion FAB in m-NBA, rel. intensity) 286.0 [100, (M—H)], 96.0 (10) and 77.9 (20). Acc. MS: m/z (FAB)$^+$ 288.1246 $C_{13}H_{22}NO_4S$ requires 288.1269.

Found C, 54.2; H, 7.35; N, 4.7; $C_{13}H_{21}NO_4S$ requires C, 54.33; H, 7.37; N, 4.87%.

Biological Data:

% Inhibition in MCF-7 Cells at 10 μM=99±2

% Inhibition in Placental Microsomes at 10 μM=40±2

% Inhibition in vivo from a single dose of 10 mg/kg=22±3

Example 9(b)

(E) Methyl-γ-methyl-6-nonenamide-N-(3-methoxyphenyl-4-O-sulphamate) (9b)

[9b]

E-Capsaicin ((E)-N-(4-Hydroxy-3-methoxyphenyl)-methyl-γ-methyl-6-nonenamide) (100 mg, 0.3274 mmol) gave a beige crude product (130 mg) which was fractionated on silica (100 g) with chloroform/acetone (2:1), and upon evaporation the second fraction gave a pale white residue (85 mg) which was recrystallized from acetone/hexane (1:2) to give 9b as pale white crystals (63 mg, 50%).

Analytical results were as follows:

m.p.=114–116° C.

$R_f$s=0.4 and 0.15 for chloroform/acetone 2:1 and 4:1 respectively vmax (KBr) 3490, 3300 (—$NH_2$), 1650 (CO), 1380 (—$SO_2N$—) $cm^{-1}$ $\delta_H$ (CDCl$_3$) (270 MHz) 0.94 (6H, d, J=6.6 Hz, 2x- CH$_3$), 1.4 (2H, pentet, —COCH$_2$CH$_2$— or =C H$_2$CH$_2$CH=CH—), 1.62 (2H, pentet, —C H$_2$CH$_2$CH=CH— or —COCH$_2$CH$_2$—), 2.0 (2H, q, —C H$_2$CH=CH—), 2.2 (3H, t, —CH$_2$CONH— and —C H(CH$_3$)$_2$), 3.87 (3H, s, C—3—OCH$_3$), 4.39 (2H, d, J=5.86 Hz, ArCH$_2$NHCO), 5.14 (2H, br s, exchanged with D$_2$O, —OSO$_2$NH$_2$), 5.34 (2H, m, —CH=CH—), 5.87 (1H, t, —NHCO—), 6.84 (1H, dd, J$_{C-6-H\ and\ C-2-H}$ 1.92 Hz and J$_{C-6-H\ and\ C-5-H}$ 8.15 Hz C—6—H), 6.86 (1H, d, J$_{C-1-H\ and\ C-6-H}$ 1.83 Hz, C—1—H) and 7.26 (1H, d, J$_{C-5-H\ and\ C-6-H}$ 8.08 Hz, C—5—H).

MS: m/z (+ve ion FAB in m-NBA, rel. intensity) 385.2 [100, (M+H)$^+$], 304.2 (20), 287.1 (10) MS: m/z (-ve ion FAB in m-NBA, rel. intensity) 383.1 [100, (M-H)], 302.2 (10), 95.9 (10) and 77.9 (35)

Found C, 56.2; H, 7.38; N, 7.29; $C_{18}H_{28}N_2O_5S$ requires C, 56.23; H, 7.34; N, 7.29%.

Biological Data:

% Inhibition in MCF-7 Cells at 10 μM=99±2

% Inhibition in Placental Microsomes at 10 μM=40±2

% Inhibition in vivo from a single dose of 10 mg/kg=22±3

9(c) 2-Nitrophenol-O-sulfamate (9c)

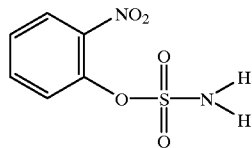

A stirred solution of 2-nitrophenol (1.391 g, 10.0 mmol) in anhydrous DMF (20 mL) was treated with sodium hydride (60% dispersion, 400 mg, 10.0 mmol) at 0° C. under an atmosphere of N$_2$. After evolution of hydrogen had ceased, sulfamoyl chloride (2 eq.) was added. The reaction mixture was stirred at room temperature overnight and then poured into water (150 mL). The resulting mixture was extracted with ethyl acetate (150 mL) and the organic portion separated was washed with brine (5×100 mL), dried (MgSO$_4$), filtered and evaporated in vacuo at 40° C. Purification by flash chromatography (ethyl acetate/hexane, 1:1) gave the crude 2-nitrophenol-O-sulfamate which was further purified by recrystallization from hot chloroform to afford the title compound as white crystals (333 mg, 745.8 μmol). The residue recovered, from the evaporation of the mother liquor, was recrystallized from chloroform/hexane to give further crops of the title compound (a total of 252 mg, 564.4 μmol, 26% overall).

Analytical results were as follows:

mp 102–103° C.

$^1$H NMR (270 MHz, CDCl$_3$) δ 5.29 (2H, br s, exchanged with D$_2$O, OSO$_2$NH$_2$), 7.48 (1H, m, C4—H or C5—H), 7.66 (1H, dd, J=1.5 and 8.3 Hz, C3—H or C6—H), 7.71 (1H, m, C4—H or C5—H) and 8.05 (1H, dd, J=1.5 and 8.3 Hz, C3—H or C6—H)

MS (EI, 70 eV) m/z (rel. intensity) 218 (2, M$^+$), 139 [100, (M—SO$_2$NH)$^+$]; MS (CI, isobutane) m/z (rel. intensity) 219 [27, (M+H)$^+$]202 [10, (M+H—NH$_3$)$^+$], 140 [100, (M+H—SO$_2$NH)$^+$], 122 [15, (M—OSO$_2$NH$_2$)$^+$]. Anal. ($C_6H_6N_2O_5S$) C, H, N.

Biological Data:

% Inhibition in MCF-7 Cells at 10 μM=99±2

% Inhibition in Placental Microsomes at 10 μM=40±2

% Inhibition in vivo from a single dose of 10 mg/kg=22±3

Example 10

Starting with the appropriate phenolic parent compound (if there are two phenol groups, it may be necessary to protect one of them using standard protection techniques for at least a part of the reaction), the ring system sulphamates according to the present invention are prepared essentially as follows. Likewise, a solution of the appropriate parent compound in anhydrous DMF is treated with sodium hydride [60% dispersion; 1.2 equiv.] at 0° C. under an atmosphere of N$_2$. After evolution of hydrogen has ceased, sulfamoyl chloride in toluene [excess, ca. 5 equiv.] is added and the reaction mixture is poured into brine after warming to room temperature overnight and diluting with ethyl acetate. The organic fraction is washed exhaustively with brine, dried (MgSO$_4$), filtered and evaporated. The crude product obtained is purified by flash chromatography and recrystallisation to give the corresponding sulfamate. All the compounds are fully characterized by spectroscopic and combustion analysis.

The following compounds of the present invention are made and are found to be steroid sulphatase inhibitors in accordance with the present invention.

Example 10i

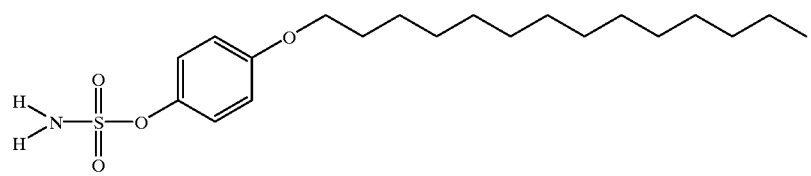

Example 10ii
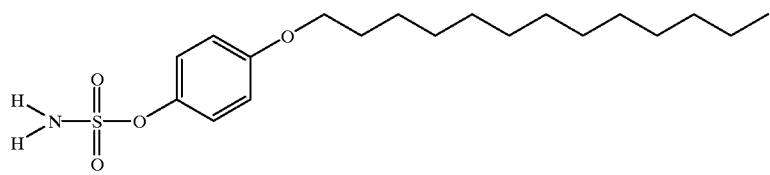
Example 10iii
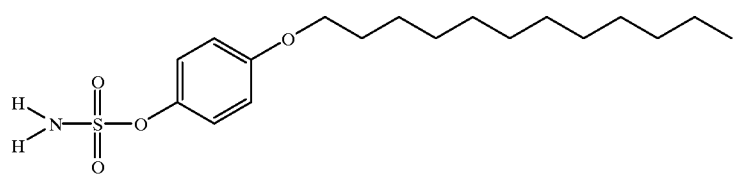
Example 10iv
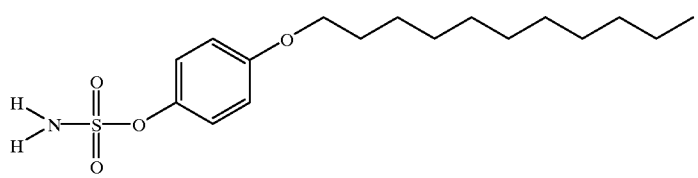
Example 10v
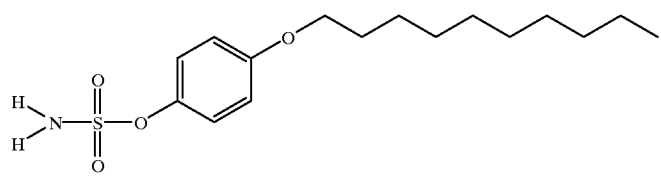
Example 10vi
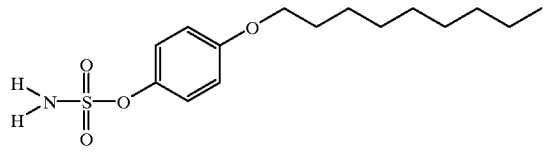
Example 10viii
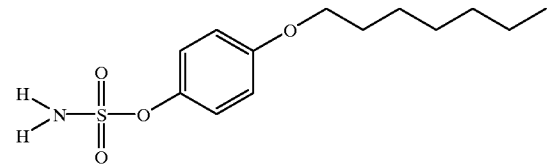
Example 10vii
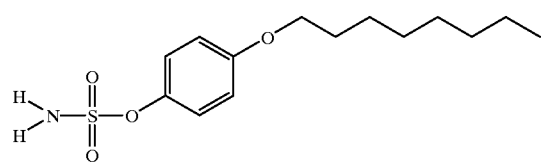
Example 10ix
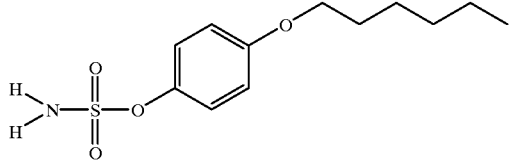

Example 10x
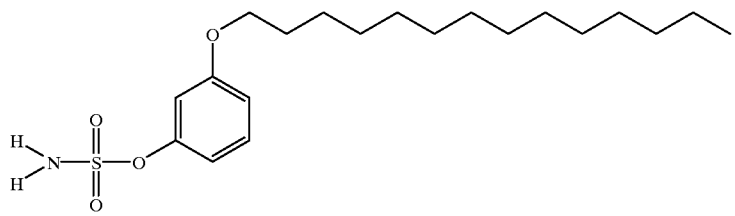
Example 10xi
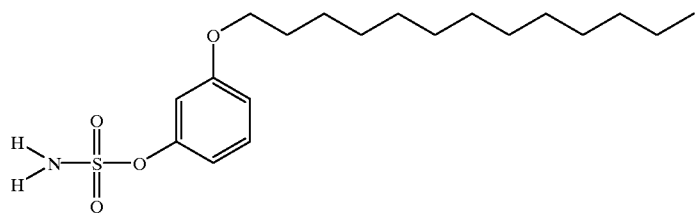
Example 10xii
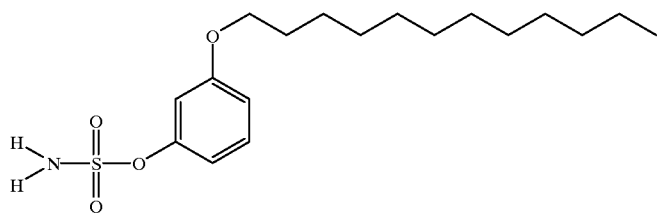
Example 10xiii
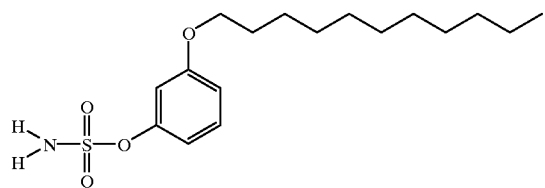
Example 10xiv
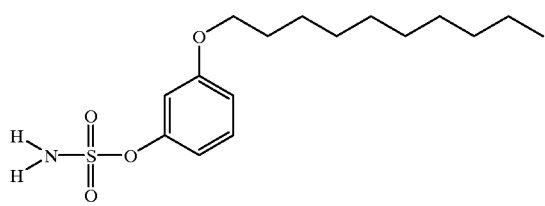
Example 10xv
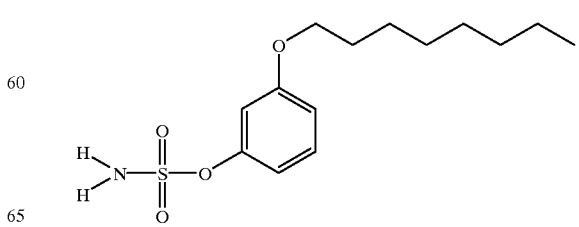
Example 10xvi Example 10xvii
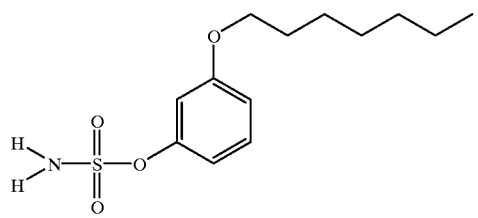
Example 10xviii
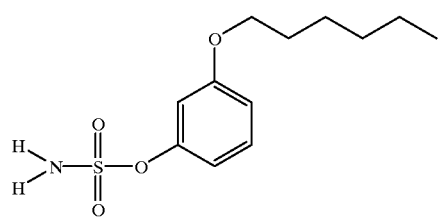
Example 10xix
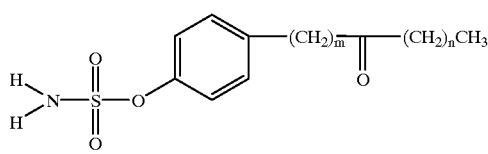
where n is an integer of from 1–3; and n is an integer of from 5–13.
Example 10xx
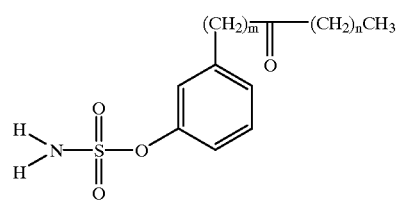
where n is an integer of from 1–3; and n is an integer of from 5–13.
Example 10xxi
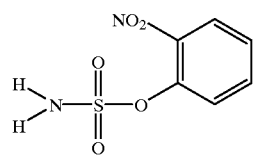
Example 10xxii
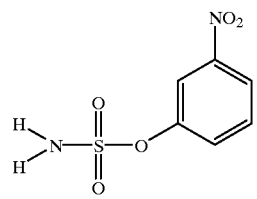
Example 10xxiii
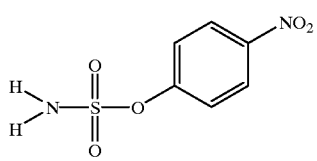
Example 10xxiv
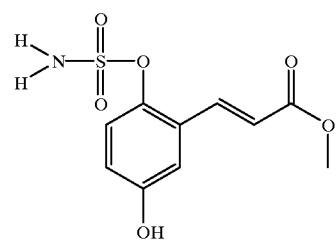
Example 10xxv
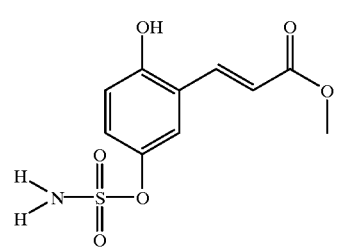
Example 10xxvi
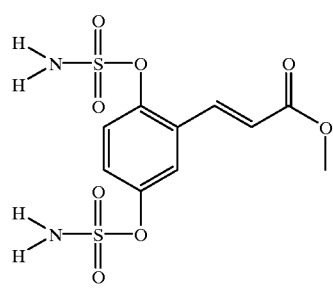

Example 10xxvii

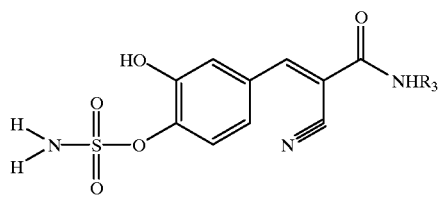

wherein $R_3$ is H or a suitable side chain—such as $C_{1-6}$ alkyl.

Example 10xxviii

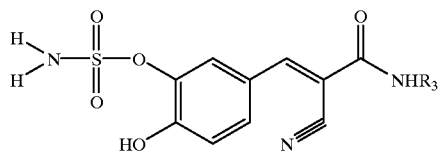

wherein $R_3$ is H or a suitable side chain—such as $C_{1-6}$ alkyl.

Example 10xxix

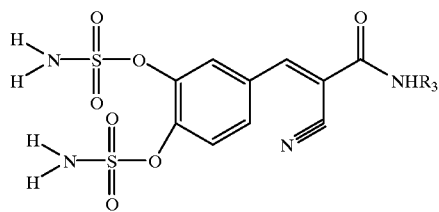

wherein $R_3$ is H or a suitable side chain—such as $C_{1-6}$ alkyl.

Example 11

Starting with the appropriate phenolic parent compound (if there are two phenol groups, it may be necessary to protect one of them using standard protection techniques for at least a part of the reaction), the ring system sulphamates according to the present invention are prepared essentially as follows. Here, a solution of the appropriate parent compound in anhydrous DMF is treated with sodium hydride [60% dispersion; 1.2 equiv.] at 0° C. under an atmosphere of $N_2$. After evolution of hydrogen has ceased, N-methyl sulfamoyl chloride in toluene [excess, ca. 5 equiv.] is added and the reaction mixture is poured into brine after warming to room temperature overnight and diluting with ethyl acetate. The organic fraction is washed exhaustively with brine, dried ($MgSO_4$), filtered and evaporated. The crude product obtained is purified by flash chromatography and recrystallisation to give the corresponding sulfamate. All the compounds are fully characterized by spectroscopic and combustion analysis.

The following compounds of the present invention are made and are found to be steroid sulphatase inhibitors in accordance with the present invention. (In the following formulae, the methyl and H groups on the sulphamate group can be interchanged.)

Example 11i

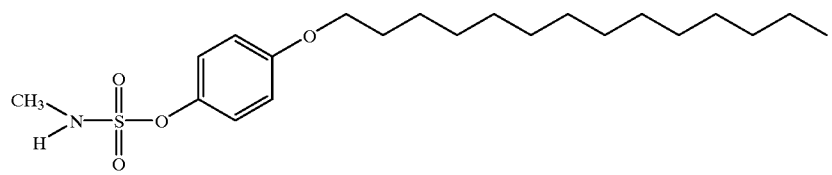

Example 11ii

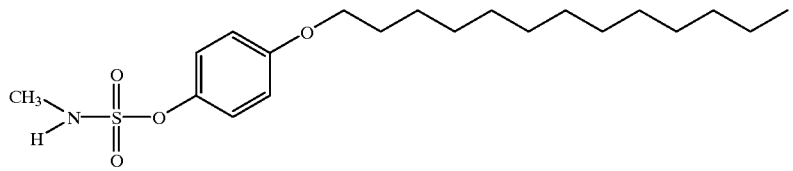

Example 11iii
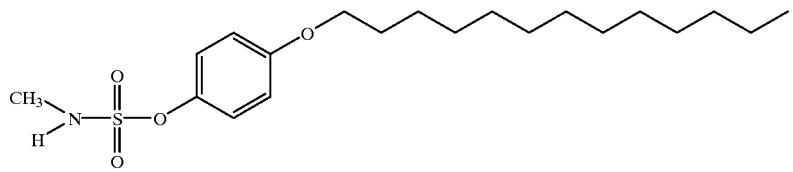
Example 11iv
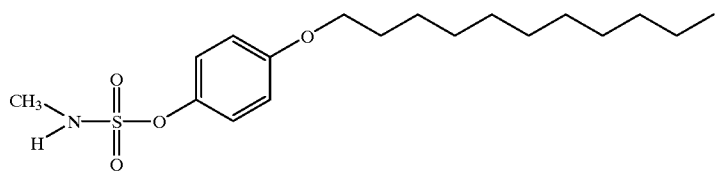
Example 11v
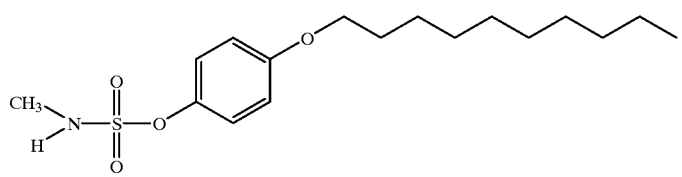
Example 11vi
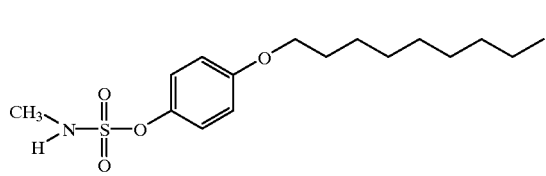
Example 11viii
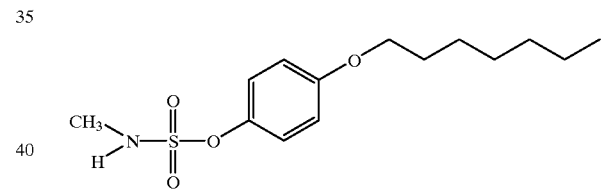
Example 11vii
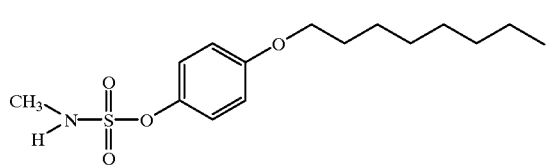
Example 11ix
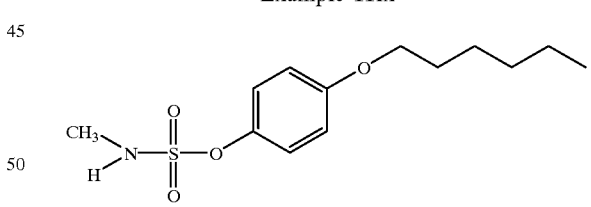
Example 11x
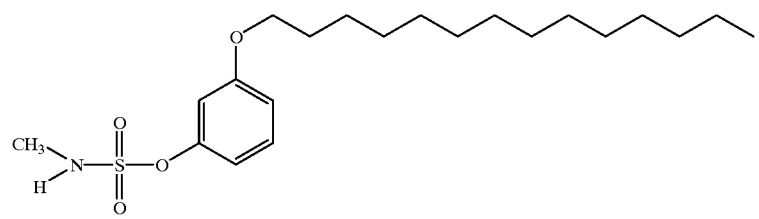

Example 11xi
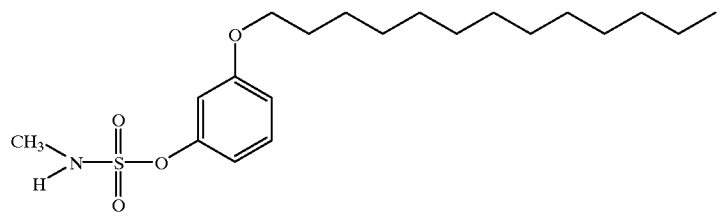
Example 11xii
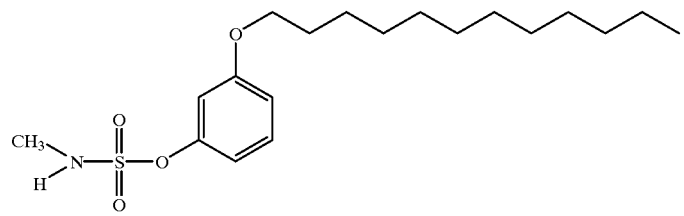
Example 11xiii
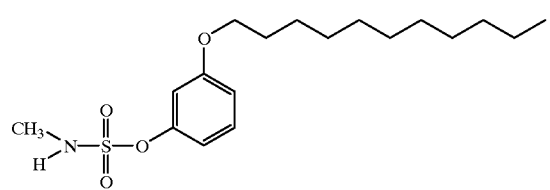
Example 11xvi
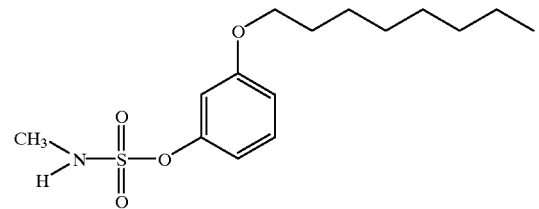
Example 11xiv
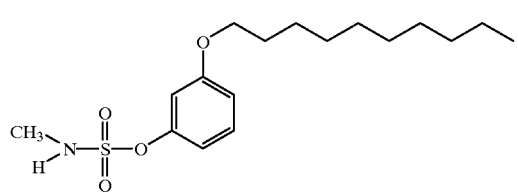
Example 11xvii
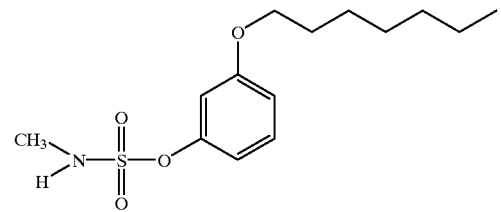
Example 11xv
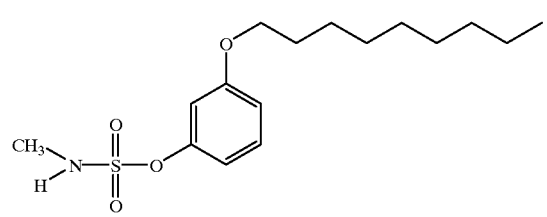
Example 11xviii
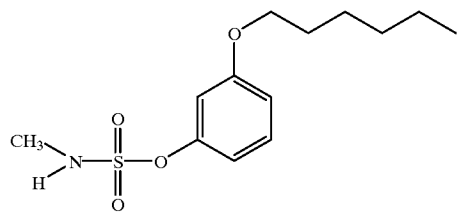

Example 11xix
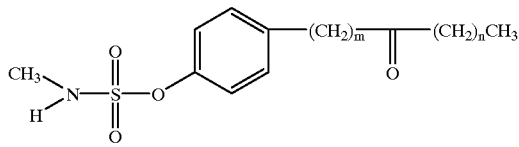
where n is an integer of from 1–3; and n is an integer of from 5–13.
Example 11xx
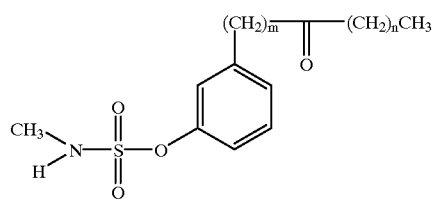
where n is an integer of from 1–3; and n is an integer of from 5–13.
Example 11xxi
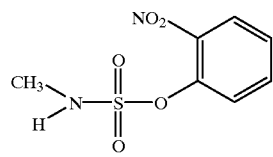
Example 11xxii
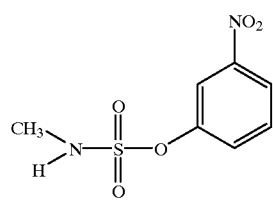
Example 11xxiii
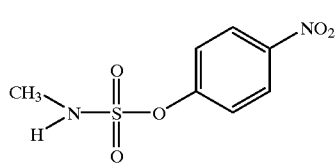
Example 11xxiv
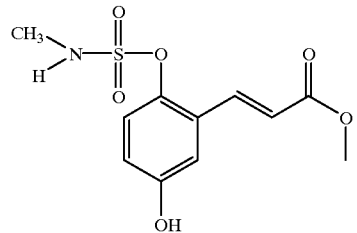
Example 11xxv
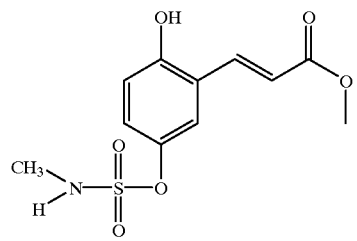
Example 11xxvi
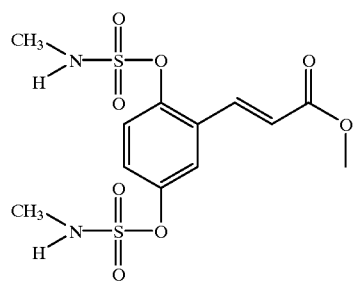
Example 11xxvii
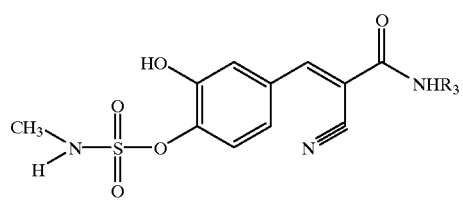
wherein $R_3$ is H or a suitable side chain—such as $C_{1-6}$ alkyl.
Example 11xxviii
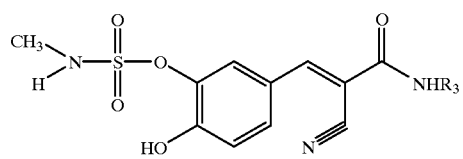
wherein $R_3$ is H or a suitable side chain—such as $C_{1-6}$ alkyl.

Example 11xxix

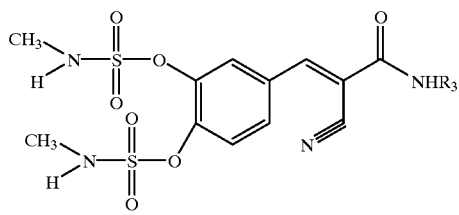

wherein $R_3$ is H or a suitable side chain—such as $C_{1-6}$ alkyl.

Example 12

Starting with the appropriate phenolic parent compound (if there are two phenol groups, it may be necessary to protect one of them using standard protection techniques for at least a part of the reaction), the ring system sulphamates according to the present invention are prepared essentially as follows. Here, a solution of the appropriate parent compound in anhydrous DMF is treated with sodium hydride [60% dispersion; 1.2 equiv.] at 0° C. under an atmosphere of $N_2$. After evolution of hydrogen has ceased, N, N-dimethyl sulfamoyl chloride in toluene [excess, ca. 5 equiv.] is added and the reaction mixture is poured into brine after warming to room temperature overnight and diluting with ethyl acetate. The organic fraction is washed exhaustively with brine, dried (MgSO$_4$), filtered and evaporated. The crude product obtained is purified by flash chromatography and recrystallisation to give the corresponding sulfamate. All the compounds are fully characterized by spectroscopic and combustion analysis.

The following compounds of the present invention are made and are found to be steroid sulphatase inhibitors in accordance with the present invention.

Example 12i

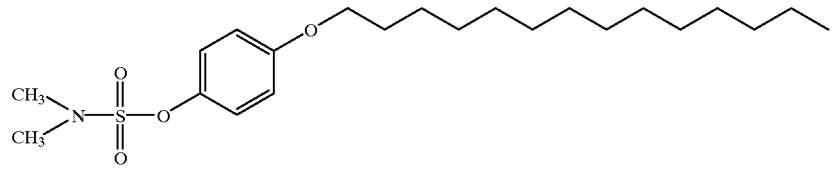

Example 12ii

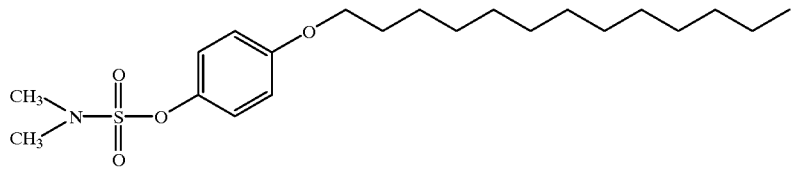

Example 12iii

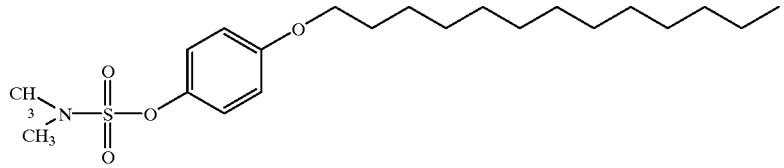

Example 12iv

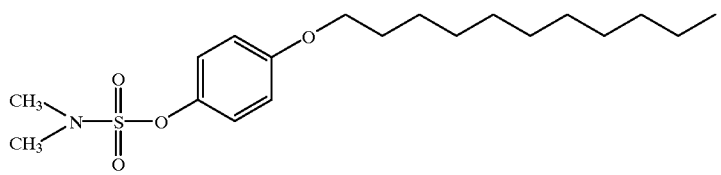

Example 12v
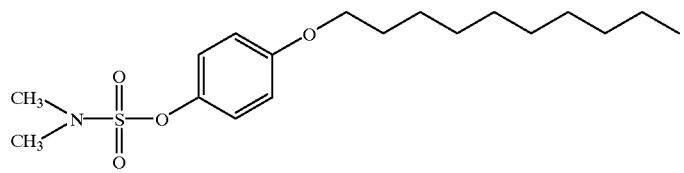
Example 12vi
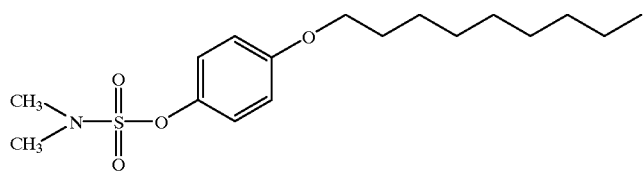
Example 12vii
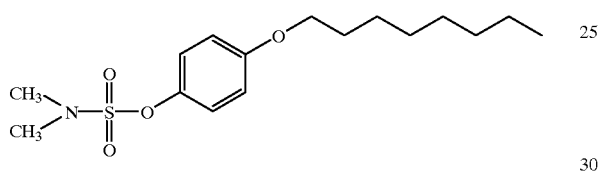
Example 12ix
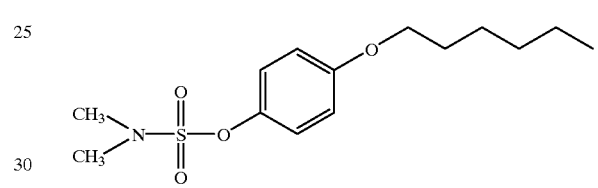
Example 12viii
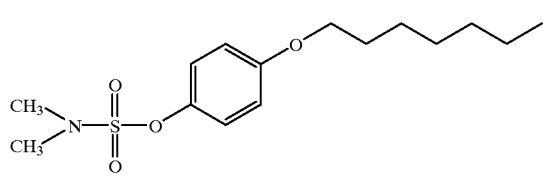
Example 12x
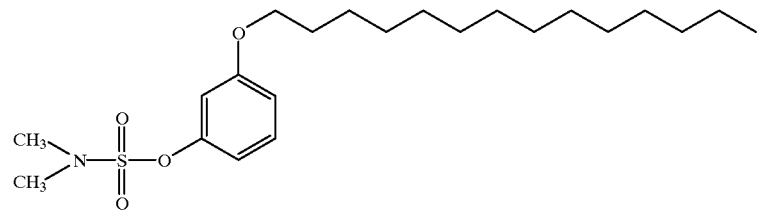

Example 12xi
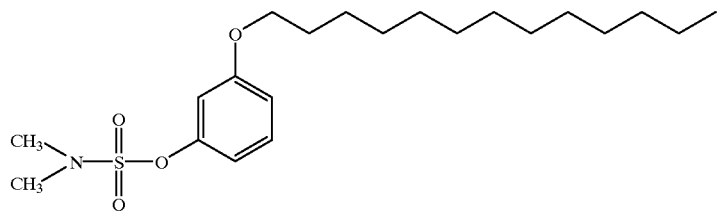
Example 12xii
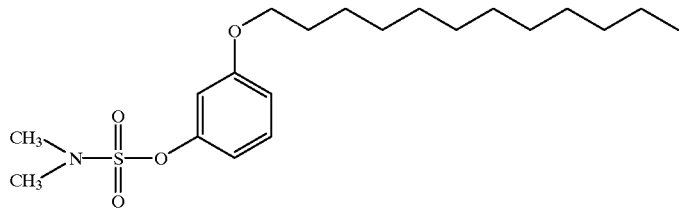
Example 12xiii
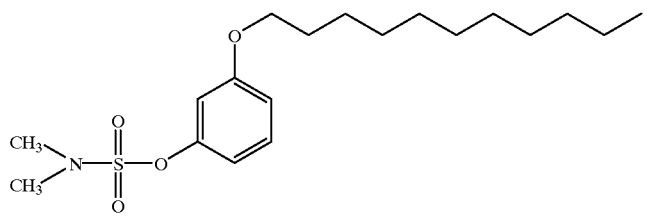
Example 12xiv
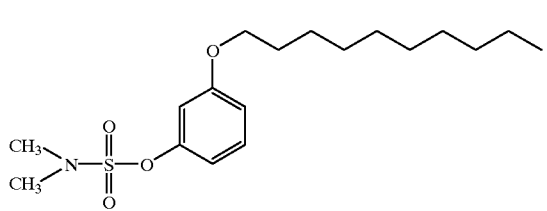
Example 12xvi
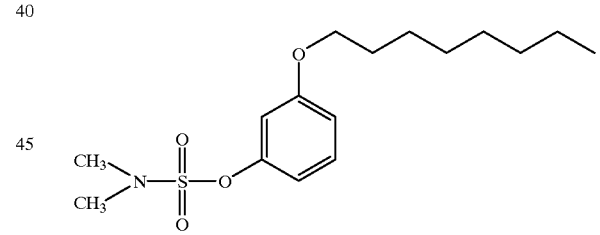
Example 12xv
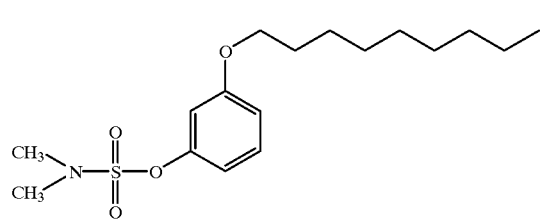
Example 12xvii
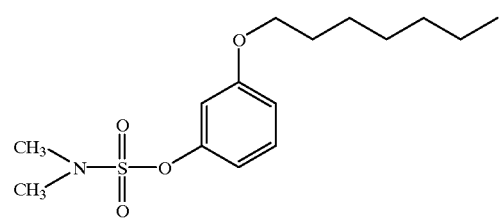

43
Example 12xviii
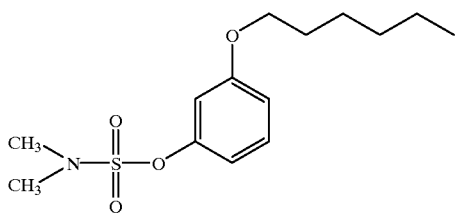
Example 12xix
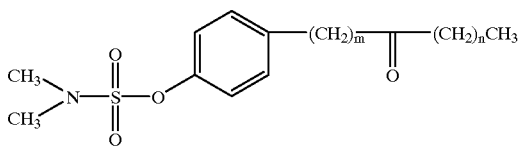
where n is an integer of from 1–3; and n is an integer of from 5–13.
Example 12xx
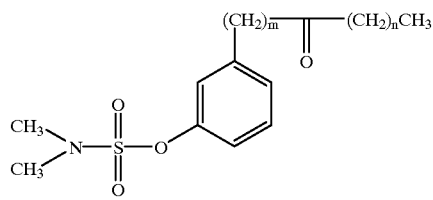
where n is an integer of from 1–3; and n is an integer of from 5–13.
Example 12xxi
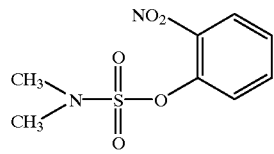
Example 12xxii
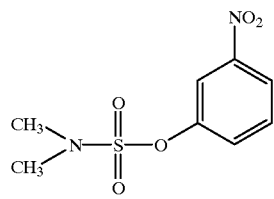
44
Example 12xxiii
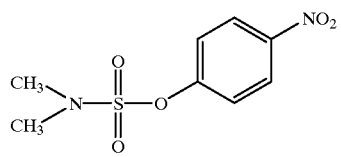
Example 12xxiv
Example 12xxv
Example 12xxvi
Example 12xxvii
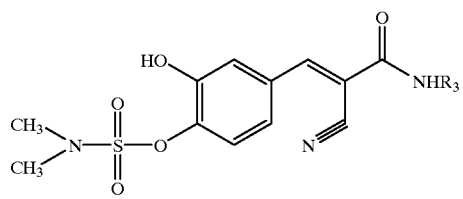
wherein $R_3$ is H or a suitable side chain—such as $C_{1-6}$ alkyl.

Example 12xxviii

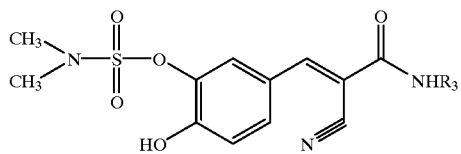

wherein $R_3$ is H or a suitable side chain—such as $C_{1-6}$ alkyl.

Example 12xxix

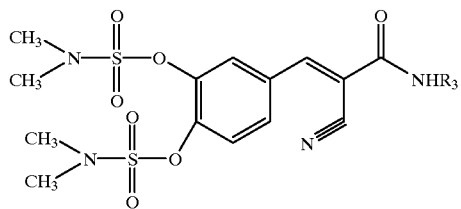

wherein $R_3$ is H or a suitable side chain—such as $C_{1-6}$ alkyl.

Example 13

The compounds of the present invention may be prepared by a process that comprises a Packman synthesis step. Packman synthesis is known in the art.

Sulphamoylation of coumarins

Figure 9:
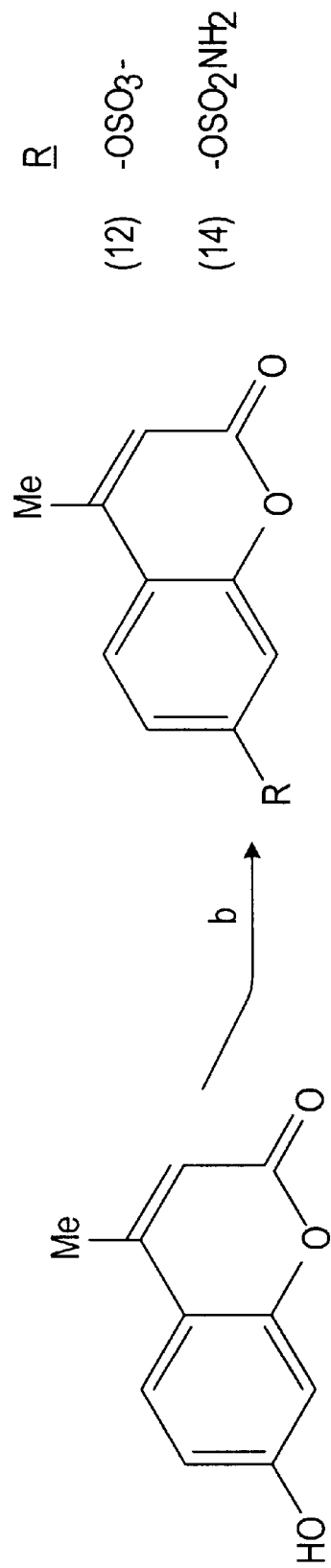
FIG. 9 shows the sulphamoylation of 7-hydroxy-4-methylcoumarin; NaH/DMF, H2NSO2Cl in toluene (Route b) (See Example 13 and WO 97/30041).

The general procedure for the sulphamoylation of coumarins was as follows. A solution of an appropriate coumarin in anhydrous DMF (ca. 40 ml per g of coumarin) was treated with sodium hydride [60% dispersion; 1 equiv] at 0° C. under an atmosphere of $N_2$. After evolution of hydrogen had ceased, sulphamoyl chloride in toluene [ca. 0.68 M, 1.5 equiv] was added and the reaction mixture was poured into water after warming to room temperature overnight and then the crude product was then quenched. The organic fraction in ethyl acetate (150 ml) was washed exhaustively with brine, dried ($MgSO_4$), filtered and evaporated. The crude product obtained was purified by flash chromatography followed by recrystallisation to give the corresponding sulphamate. All new compounds were fully characterised by spectroscopic and combustion analysis. The synthesis of 4 methylcoumarin-7-O-sulphamate (14) is shown in FIG. 9.

Figure 7:
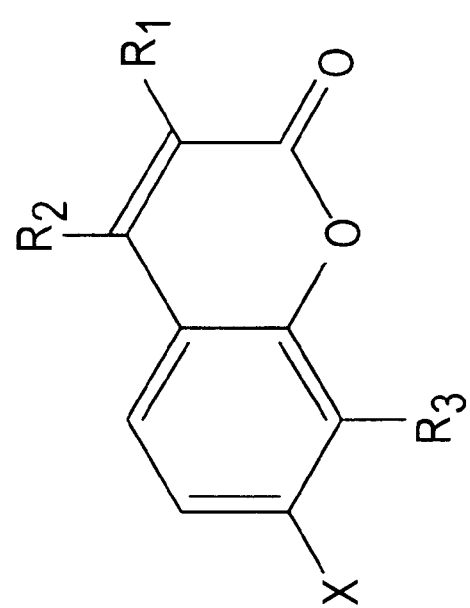
FIG. 7 shows the structures of 7-hydroxycoumarin (11), 7-(sulphoxy)-4-methylcoumarin (12) and coumarin sulphamates (13–16) (See Example 13 and WO 97/30041).

Following this general procedure, compounds 13–16 (as shown in FIG. 7)—i.e. coumarin-7-O-sulphamate (13), 4-methylcoumarin-7-O-sulphamate (14), 3,4,8-trimethylcoumarin-7-O-sulphamate (15) and 4-(trifluoromethylcoumarin)-7-O-sulphamate (16)—were prepared. More details on the synthesis of these compounds now follow.

The synthesis of compound 12 (as shown in FIG. 7) is also discussed below.

Preparation of Coumarin-7-O-sulphamate (13)

Following the above-mentioned general procedure, 7-Hydroxycoumarin (500 mg, 3.082 mmol) gave a crude product (605 mg) which was fractionated on silica (200 g) by gradient elution with chloroform/acetone (8:1, 500 ml; 4:1, 1000 ml and then 2:1, 500 ml). Upon evaporation, the second fraction gave a creamy yellow residue (389 mg, 52.3%) which was recrystallised in ethyl acetate/hexane (1:1) to give (13) as dull white crystals (239 mg).

Analytical data were as follows:

M.p. 170.0–171.5° C.; $R_f$s=0.48 (ether), 0.67 (ethyl acetate), 0.19 (chloroform/acetone, 4:1); vmax (KBr) 3360, 3210, 3060, 1720, 1615, 1370, 1125 cm$^{-1}$; $\delta_H$ (DMSO-$d_6$/ CDCl$_3$, ca. 1:25) 6.415 (1H, d, $J_{C-4-H,C-3-H}$=9.7 Hz, C—3—H), 7.285 (1H, dd, $J_{C-8-H,C-6-H}$=2.3 Hz and $J_{C-5-H,C-6-H}$=8.5 Hz, C—6—H), 7.379 (1H, d, $J_{C-6-H,C-8-H}$=2.2 Hz, C—8—H), 7.508 (2H, br s, $D_2O$ exchanged, —N$H_2$), 7.543 (1H, d, $J_{C-6-H,C-5-H}$=8.4 Hz, C—5—H) and 7.760 (1H, d, $J_{C-5-H,C-4-H}$=9.7 Hz, C—4—H). MS: m/z (E.I., rel. intensity) 241.0 (10), 162.0 (97), 134.0 (100), 105.0 (23). Acc. MS: m/z 241.0068, $C_9H_7NO_5S$ requires 241.0045. Found: C, 44.8; H, 2.89; N, 5.82. $C_9H_7NO_5S$ requires C, 44.81; H, 2.92; N, 5.81%.

Preparation of 4-Methylcoumarin-7-O-sulphamate (14)

Following the above-mentioned general procedure, 7-Hydroxy-4-methylcoumarin (500 mg, 2.753 mmol) gave a crude product (633 mg) which was fractionated on silica (200 g) by gradient elution with chloroform/acetone (8:1, 500 ml; 4:1, 1000 ml, 2:1, 500 ml and then 1:1, 500 ml). Upon evaporation, the second fraction gave a creamy yellow residue (425 mg, 60.5%) which was recrystallised in acetone/chloroform (3:5) to give (14) as colorless rhombic crystals (281 mg).

Analytical data were as follows:

M.p. 165–167° C.; $R_f$s=0.48 (ether), 0.29 (ether/hexane 8:1), 0.26 (chloroform/acetone, 4:1); vmax (KBr) 3320, 3180, 3080, 1700, 1620, 1560, 1380, 1125 cm$^{-1}$; $\delta_H$ (acetone-$d_6$) 2.507 (3H, s, —C$H_3$), 6.339 (1H, s, C—3—H), 7.299 (2H, m, C—6—H and C—8—H), 7.390 (2H, br s, $D_2O$ exchanged, —N$H_2$) and 7.850 (1H, d, $J_{C-6-H,C-5-H}$=9 Hz, C—5—H). MS: m/z (+ve ion FAB in m-NBA, rel. intensity) 542.2 (15), 511.1 [45, (2M+H)$^+$], 461.2 (20), 409.1 [60, (M+H+NBA)$^+$], 393.3 [60, (M+H+NBA-16)$^+$], 329.2 [10, (M+H+NBA-80)$^+$], 256.1 [100, (M+H)$^+$]. MS: m/z (−ve ion FAB in m-NBA, rel. intensity) 421.0 (20), 407.1 [15, (M−H+NBA)$^-$], 335.1 (14), 254 [100, (M−H)$^-$], 175.1 [32, (M−H−79)$^-$], 121.0 (17). Found: C, 47.2; H, 3.56; N, 5.51. $C_{10}H_9NO_5S$ requires C, 47.06; H, 3.55; N, 5.49%.

Preparation of 3,4,8-Trimethylcoumarin-7-O-sulphamate (15)

Following the above-mentioned general procedure, 7-Hydroxy-3,4,8-trimethylcoumarin (1.0 g, 4.896 mmol) gave a crude product (1.33 g) which upon recrystallisation in hot ethyl acetate yielded 238 mg of starting coumarin. The mother liquor was evaporated and the white residue obtained (1.13 g) was fractionated on silica (200 g) with ether. The second fraction was collected, evaporated and the residue obtained (519 mg, 37.4%) was recrystallised in acetone/ hexane (1:2) to give (15) as pale yellow crystals (312 mg).

Analytical data were as follows:

M.p. 197–202° C.; $R_f$s=0.50 (ether), 0.69 (ethyl acetate); vmax (KBr) 3310, 3040, 1680, 1600 cm$^{-1}$; $\delta_H$ (acetone-$d_6$) 2.176, 2.383 and 2.458 (9H, three s, 3×C$H_3$), 7.374 (1H, d, $J_{C-5-H,C-6-H}$=8.8 Hz, C—6—H), 7.390 (2H, br s, $D_2O$ exchanged, —N$H_2$) and 7.682 (1H, d, $J_{C-6-H,C-5-H}$=8.8 Hz, C—5—H). MS: m/z (E.I., rel. intensity) 283.1 (10), 204.1 (45), 176.1 (40), 161.1 (22), 69.1 (56), 57.1 (40), 43.1 (100). Acc. MS: m/z 283.0497, $C_{12}H_{13}NO_5S$ requires 283.0514. Found: C, 50.86; H, 4.63; N, 4.97. $C_{12}H_{13}NO_5S$ requires C, 50.88; H, 4.63; N, 4.94%.

Preparation of 4-(Trifluoromethyl)coumarin-7-O-sulphamate (16)

Following the above-mentioned general procedure, 7-Hydroxy-4-(trifluoromethyl)coumarin (0.90 g, 3.911 mmol) gave a crude product (1.20 g) which was fractionated on silica (200 g) with ether/chloroform (1:4). The residue (393 mg) from the third fraction was further purified by fractionating on silica (100 g) with ether. The first fraction then collected gave a residue (295 mg, 24.4%) which upon recrystallised in ethyl acetate/hexane (1:3) gave (16) as white needle-shaped crystals (160 mg).

Analytical data were as follows:

M.p. 165–168° C.; $R_f$s=0.67 (ether), 0.24 (ether/chloroform, 1:4), vmax (KBr) 3360, 3240, 3100, 1720, 1620, 1380, 1160 cm$^{-1}$; $\delta_H$ (acetone-d$_6$) 6.995 (1H, s, C—3—$\underline{H}$), 7.461 (1H, dd, $J_{C\text{-}8\text{-}H,C\text{-}6\text{-}H}$=2.8 Hz and $J_{C\text{-}5\text{-}H,C\text{-}6\text{-}H}$=8.1 Hz, C—6—$\underline{H}$), 7.478 (1H, s, C—8—$\underline{H}$), 7.53 (2H, br s, D$_2$O exchanged, —N$\underline{H}_2$) and 7.89 (1H, m, C—5—$\underline{H}$). $^1$H-NMR spectrum of (16) in DMSO-d$_6$/CDCl$_3$ (ca. 1:15) showed partial decomposition to the starting coumarin. MS: m/z (E.I., rel. intensity) 309.0 (2.6), 230.0 (77), 202.0 (100), 183.5 (5), 173.0 (10), 69.0 (33). Acc. MS: m/z 308.9874, C$_{10}$H$_6$F$_3$NO$_5$S requires 308.9919. Found: C, 38.8; H, 1.85; N, 4.53. C$_{10}$H$_6$F$_3$NO$_5$S requires C, 38.84; H, 1.96; N, 4.53%.

Preparation of 7-(Sulphoxy)-4-Methylcoumarin, sodium salt (12)

Figure 8:
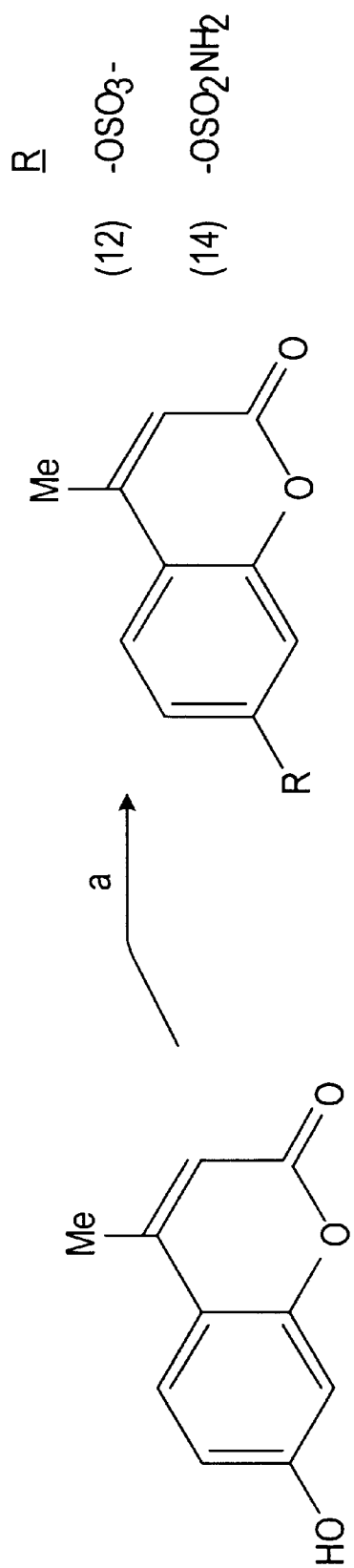
FIG. 8 shows the sulphation of 7-hydroxy-4-methylcoumarin; pyridine/SO3-pyridine complex, NaOH in MeOH (Route a) (See Example 13 and WO 97/30041).

To a solution of 7-hydroxy-4-methylcoumarin (1.0 g, 5.676 mmol) in dried pyridine (20 ml) under an atmosphere of N$_2$ [FIG. 8] was added sulphur trioxide-pyridine complex (1.8 g, 11.35 mmol, 2 equiv.) and the reaction mixture was stirred overnight. After removal of pyridine, methanol (20 ml) was added to the creamy syrup obtained and the resulting light yellow solution was basified (pH~8) by dropwise addition of sodium hydroxide in methanol (1 M, ca. 18 ml). The bright yellow suspension formed was filtered and the precipitated washed with more methanol. The filtrate was then concentrated to 30–40 ml and ether (total 120 ml) was added in portions until precipitation completed. The light beige precipitate was collected (711 mg) and 582 mg of which was recrystallised in methanol/ether (1:1) to give (12) as light creamy yellow crystals (335 mg).

Analytical data were as follows:

M.p. 172–175° C. (dec.); $R_f$s=0.51 (methanol/ethyl acetate, 1:3), 0.67 (methanol/ether, 1:3); vmax (KBr) 3500 (br), 3080, 1680, 1610, 1560, 1300, 1260, 1050 cm$^{-1}$; $\delta_H$ (DMSO-d$_6$) 2.407 (3H, s, —C$\underline{H}_3$), 6.269 (1H, s, C—3—$\underline{H}$), 7.20 (2H, m, C—6—$\underline{H}$ and C—8—$\underline{H}$), and 7.695 (1H, d, $J_{C\text{-}6\text{-}H,C\text{-}5\text{-}H}$=8.8 Hz, C—5—$\underline{H}$). MS: m/z (+ve ion FAB in m-NBA, rel. intensity) 176 (100, NBA+NA$^+$). MS: m/z (-ve ion FAB in m-NBA, rel. intensity) 175.1 (14, M—Na$^+$–SO$_3$), 255.0 (100, M–Na$^+$), 408.0 (8, M–Na$^+$+NBA), 431.0 (15, M+153), 444.0 (20), 533.0 (15), 230.0 (77), 202.0 (100), 183.5(5), 173.0 (10), 69.0 (33). Acc. MS: m/z (-ve ion FAB in glycerol, rel. intensity) 254.9982 (25), C$_{10}$H$_7$O$_6$S requires 254.9963. Found: C, 40.3; H, 2.92. C$_{10}$H$_7$O$_6$NaS.H$_2$O requires C, 40.55; H, 3.06%. HPLC [Spherisorb ODS5, 25×4.6 mm; Mobile phase: MeOH/H$_2$O (70:30), Flow rate: 1 ml/min; $\lambda_{max}$: 316 nm]: $t_R$=1.5 min, c.f. 7-hydroxy-4-methylcoumarin, 3.6 min.

Other data were as follows:

Compound 12 is stable in bases such as sodium hydroxide in methanol but not in acidic conditions. In addition, incomplete basification of the reaction mixture with sodium hydroxide in methanol (<3 equivalents) leads to decomposition of (12). Two equivalents of sodium hydroxide are required for consuming excess sulphur trioxide-pyridine complex to yield the neutral sodium sulphate. Insufficient amount of sodium hydroxide will therefore lead to the formation of sodium hydrogen sulphate which is acidic. Compound 12 appears labile to high temperature as one experiment has shown complete decomposition to 7-hydroxy-4-methylcoumarin after heating (12) as solid at 90° C. for 4 h.

In vitro tests

The above-mentioned coumarin sulphamates were tested for their ability to inhibit E1-STS activity using intact MCF-7 breast cancer cells or placental microsomes (100, 000 g fraction) essentially as previously described.

To examine whether compound (12) could act as a substrate for E1-STS, 100 μg of the compound was incubated for 1 hour with placental microsomes in the absence or presence of EMATE (10 μM). The unconjugated coumarin formed at the end of the incubation was extracted with diethyl ether. After evaporation of solvent, the residue was examined by TLC using ethyl acetate/methanol (80:20) as eluent, in which the coumarin sulphate (12) and 7-hydroxy-4-methylcoumarin had $R_f$ values of 0.79 and 0.95 respectively. Only unconjugated 7-hydroxy-4-methylcoumarin was detected after incubation of compound (12) with placental microsomes. The inclusion of EMATE in the reaction mixture reduced the hydrolysis of compound (12) by E1-STS, indicating that the coumarin sulphate is indeed a substrate for the sulphatase.

Figure 10:
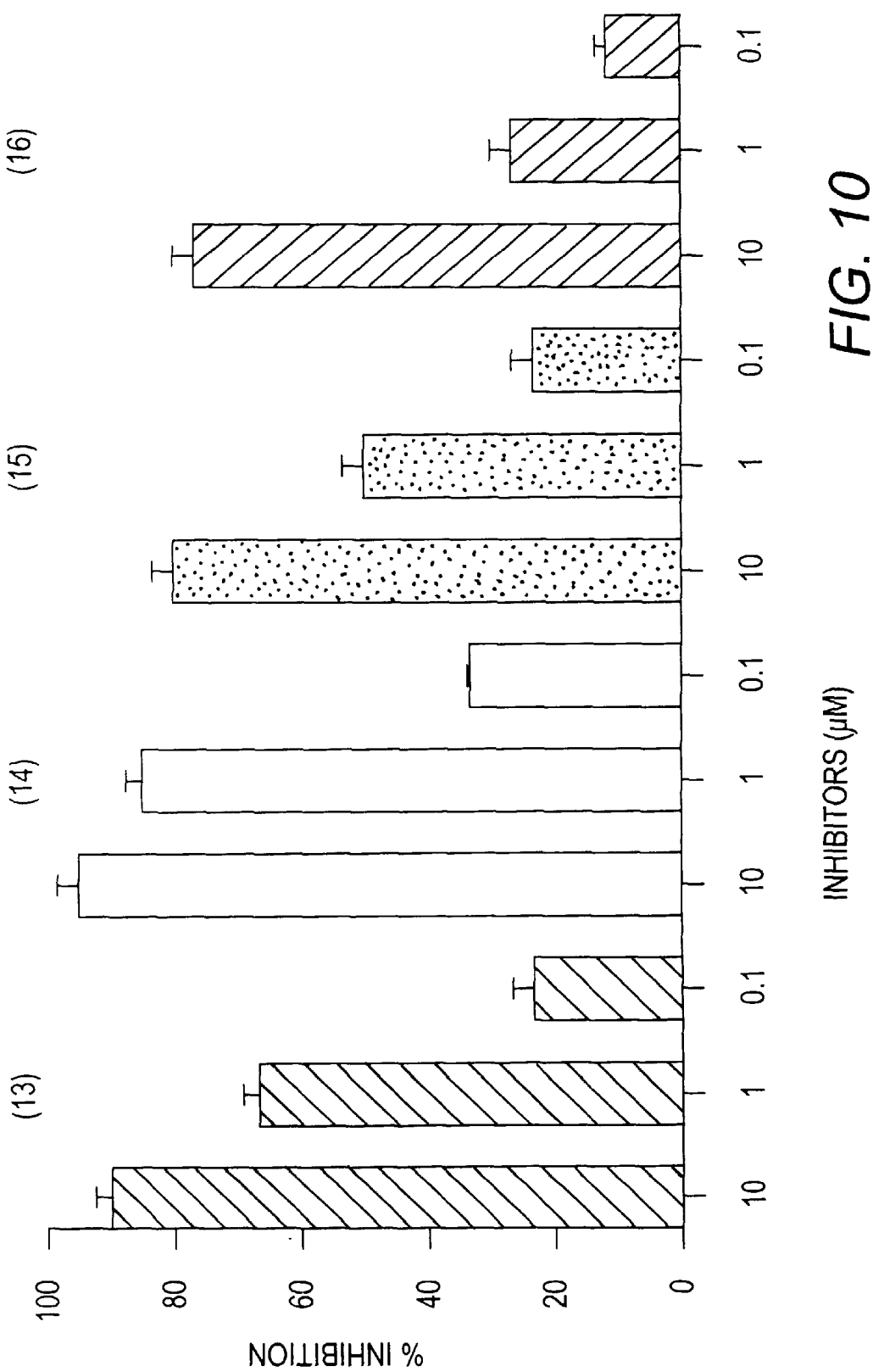
FIG. 10 shows the dose-dependent inhibition of oestrone sulphatase in intact MCF-7 breast cancer cells by coumarin-7-O-sulphamate (13), 4-methylcoumarin-7-O-sulphamate (14), 3,4,8-trimethyl-coumarin-7-O-sulphamate (15) and 4-(trifluoromethyl)coumarin-7-O-sulphamate (16) (See Example 13 and WO 97/30041).

The dose-dependent inhibition of oestrone sulphatase in intact MCF-7 breast cancer cells by coumarin-7-O-sulphamate (13), 4-methylcoumarin-7-O-sulphamate (14), 3,4,8-trimethyl-coumarin-7-O-sulphamate (15) and 4-(trifluoromethyl)coumarin-7-O-sulphamate (16) can be seen from FIG. 10. Assays were performed essentially as previously described. Monolayers of intact MCF-7 cells in 25 cm$^3$ flasks were incubated for 20 h at 37° C. with [$^3$H]oestrone sulphate (2 nM) and coumarin sulphamates at 0.1–10 μM. Oestrone sulphatase activity was determined by measuring the total amount of $^3$H-labeled oestrone and oestradiol formed. Sulphatase activity in untreated cells was 100–200 fmol/20 h/10$^6$ cells. Each point represents the mean±s.d. of triplicate measurements. (J. Med. Chem. 1994, 37, 219–21; Biochemistry 1995, 34, 11508–14.)

The free parent coumarins of all coumarin sulphamates prepared showed little or no E1-STS inhibitory activity when tested up to 10 μM. However, in contrast, all four coumarin sulphamates (compounds 13–16) inhibited oestrone sulphatase inhibitory activity in a dose-dependent manner (FIG. 10) and the inhibition at 10 μM ranged from 71.5% for compound 16 to 93.3% for compound 14. The IC$_{50}$ for inhibition of E1-STS by compound 14, the most effective inhibitor, measured using intact MCF-7 cells was 380 nM.

Figure 11:
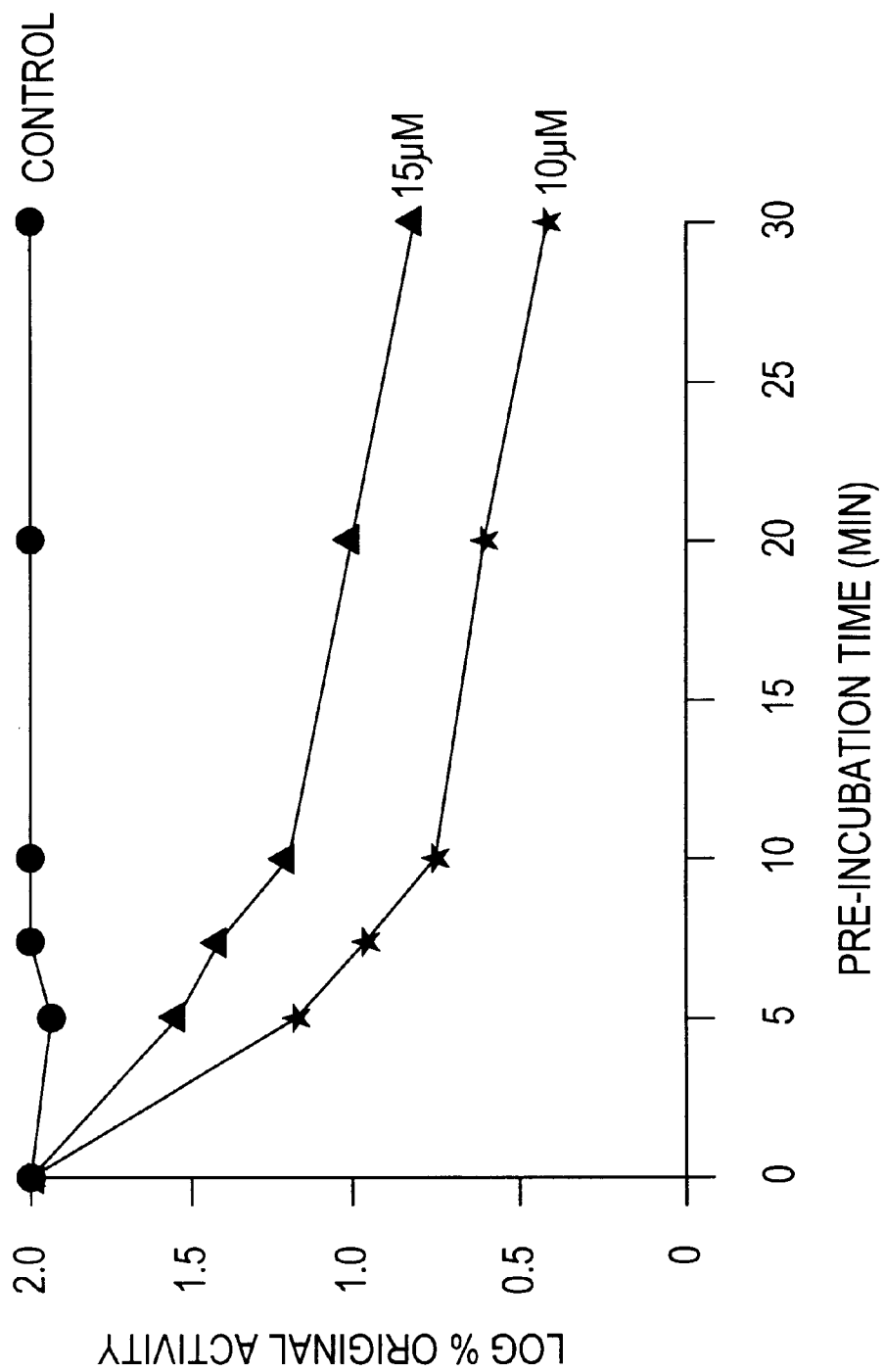
FIG. 11 shows the time-dependent and the concentration-dependent inactivation of oestrone sulphatase by 4-methyl-coumarin-7-O-sulphamate (14) (See Example 13 and WO 97/30041).

The time- and concentration-dependent inactivation of oestrone sulphatase by 4-methyl-coumarin-7-O-sulphamate (14) can be seen from FIG. 11. Placental microsomes (200 μg) were preincubated with (14) control, ●; 0.5 μM, Δ and 10 μM, *) for 0–30 min at 37° C. followed by incubation with dextran-charcoal for 10 min at 4° C. Dextran-charcoal was sedimented by centrifugation and portions of the supernatants were then incubated with [$^3$H]oestrone sulphate (20 μM) for 1 h at 37° C. to assess remaining sulphatase activity. Duplicate experiments were run at each concentration, but assays for residual activity were taken at different times in each experiment.

As with EMATE, compound 14 inhibited E1-STS activity in a time- and concentration-dependent manner in a biphasic fashion (FIG. 11), indicating a similar mechanism of action (potential chemical modification of two active site residues). At 10 μM, compound 14 reduced the original E1-STS activity by 95% after preincubating the enzyme with the inhibitor for 20 min.

Additional experiments revealed that compound 14 inhibited placental microsomal DHA-STS activity by 93.6% at the same concentration.

In Vivo Tests

In order to examine if compound 14 possessed oestrogenic activity and also to test its ability to inhibit E1-STS in vivo, it was administered to rats (1 mg/kg subcutaneously, in propylene glycol for 5 days) 14 days after ovariectomy had been performed.

Administration of compound 14 did not result in any significant increase in the uterine weight in these rats (data not shown), showing that compound 14 showed reduced oestrogenic agonist properties. The E1-STS activity in the uteri obtained from these animals was inhibited by 89.4% compared with the activity in untreated animals.

Preliminary data also demonstrate potent oral activity in rats for compound 14, similar to that observed for EMATE.

In addition to these in vivo results, another series of rats (each weighing approximately 200 g) received 4-methyl coumarin-7-O-sulphamate (compound 14) orally in propylene glycol either as a single dose (SD) or daily for seven days (Multiple Dose, MD).

Inhibition of sulphatase activity was assessed in white blood cells (wbcs) that were collected after a SD or MD. Sulphatase activity was assayed using labelled oestrone sulphate as the substrate and measuring the release of oestrone.

Figure 12:
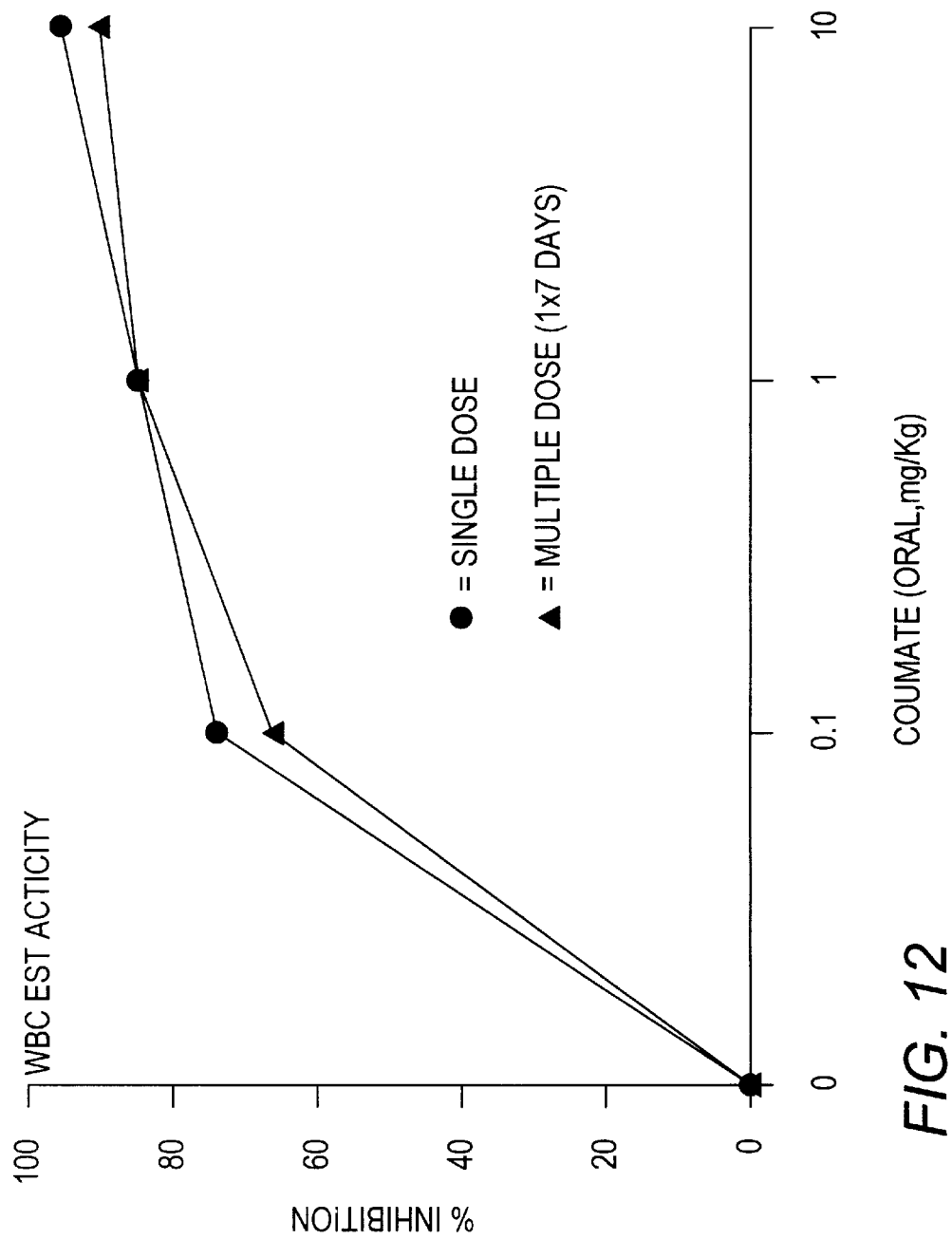
FIG. 12 is a graph (% inhibition vs. coumate) (See Example 13 and WO 97/30041).
Figure 14:
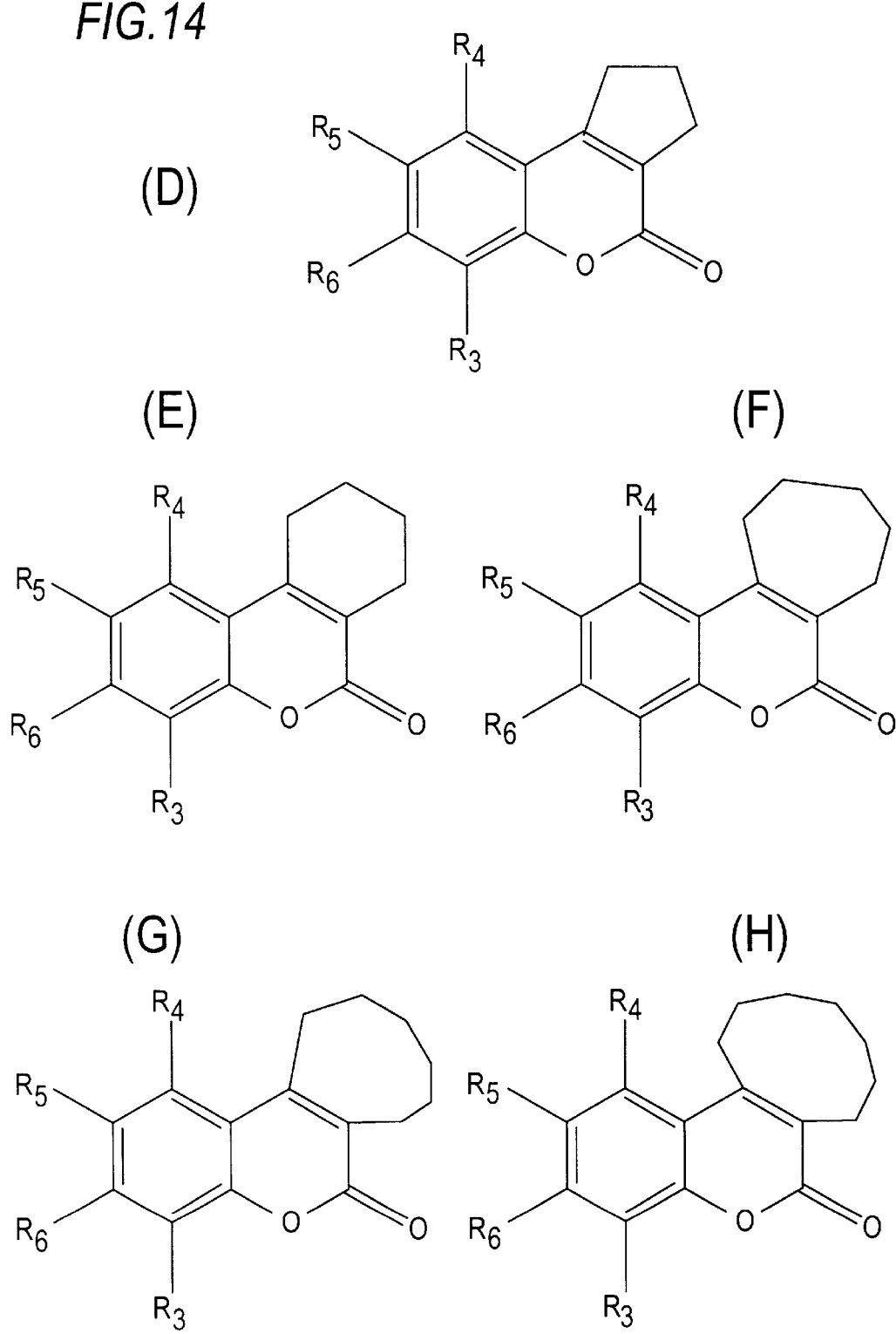
Figure 15:
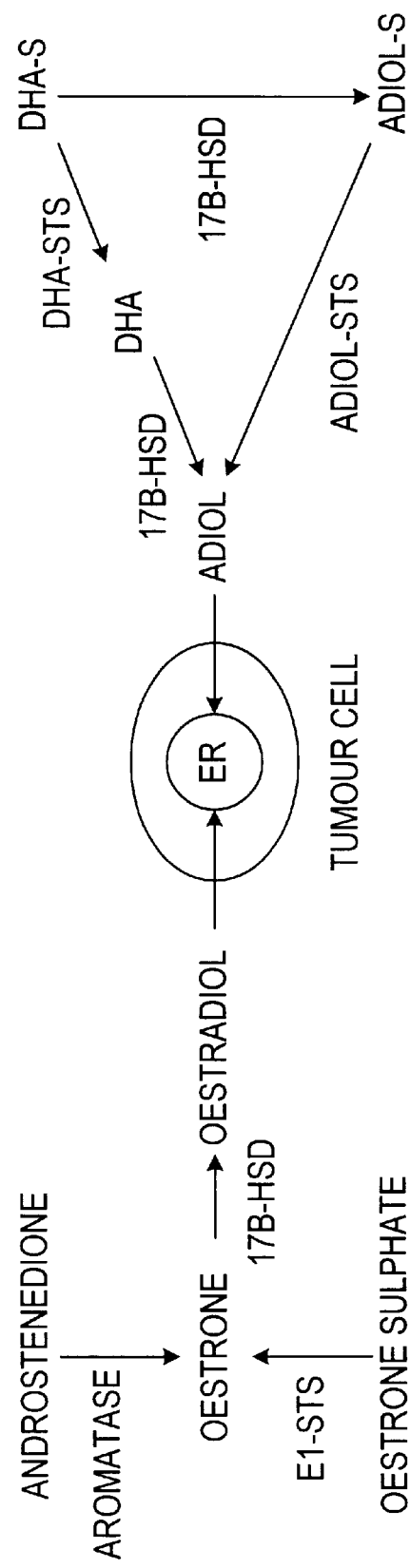
FIG. 15 shows a schematic diagram of some enzymes involved in the in situ synthesis of oestrone from oestrone sulfate, oestradiol and androstenedione (See Example 14 and WO 97/32872; see also FIG. 1.
Figure 16A:
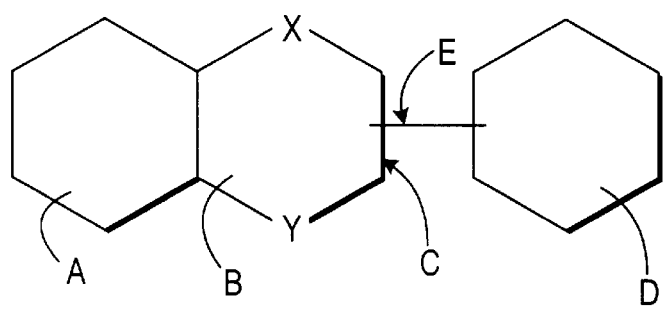
Figure 16B:
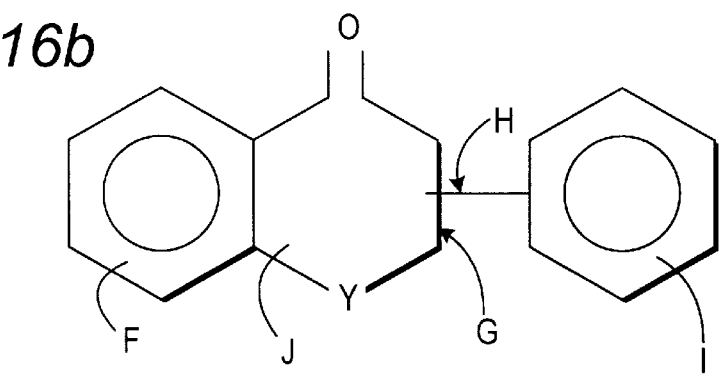
Figure 16C:
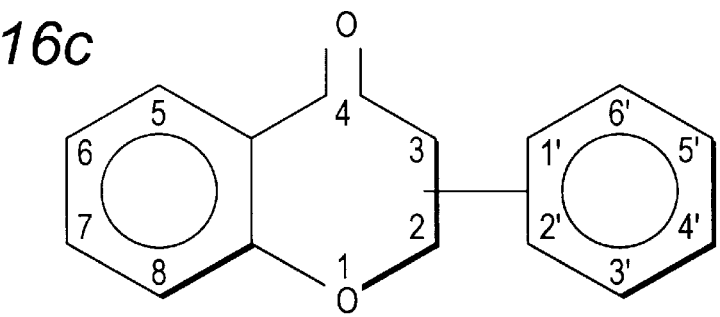
Figure 20:
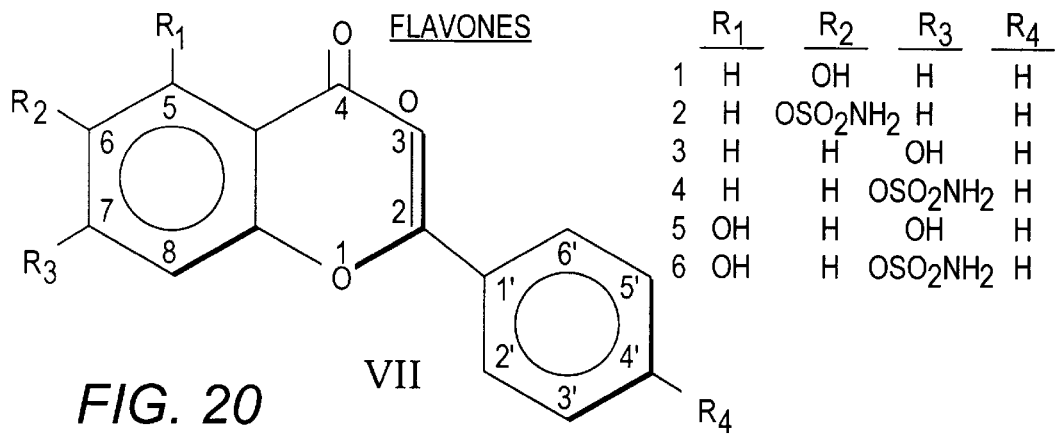
Figure 21:
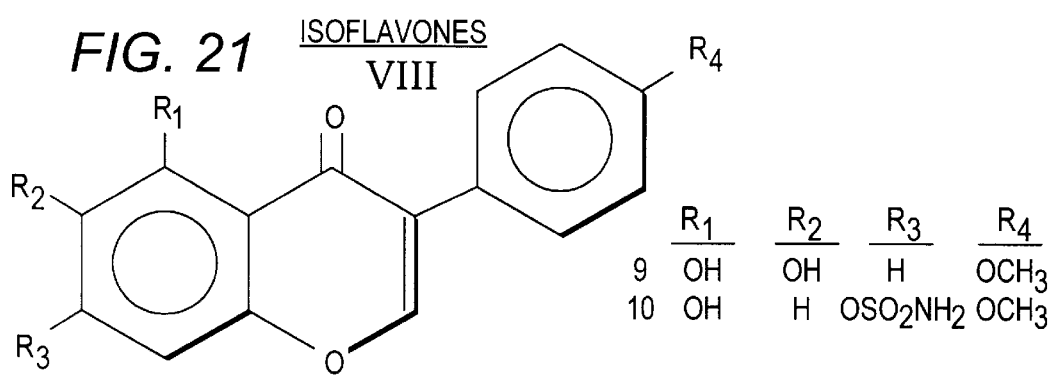
Figure 22:
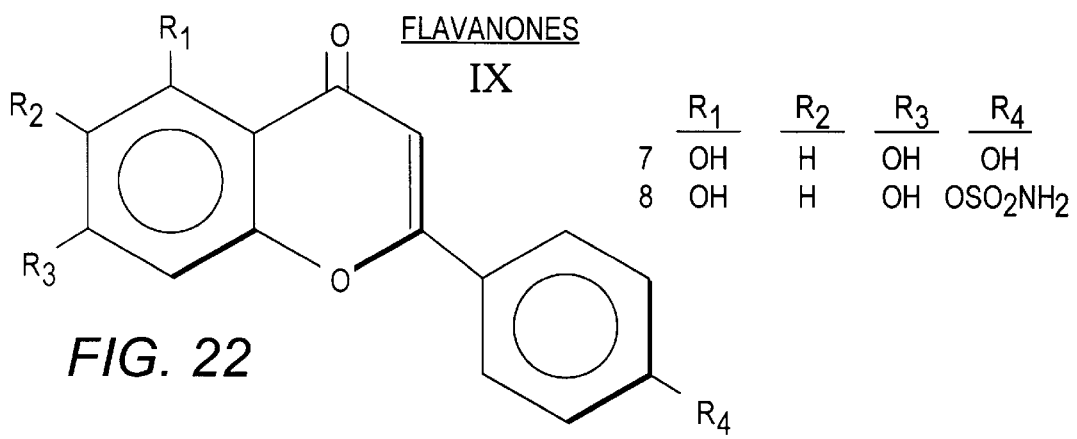
Figure 23:
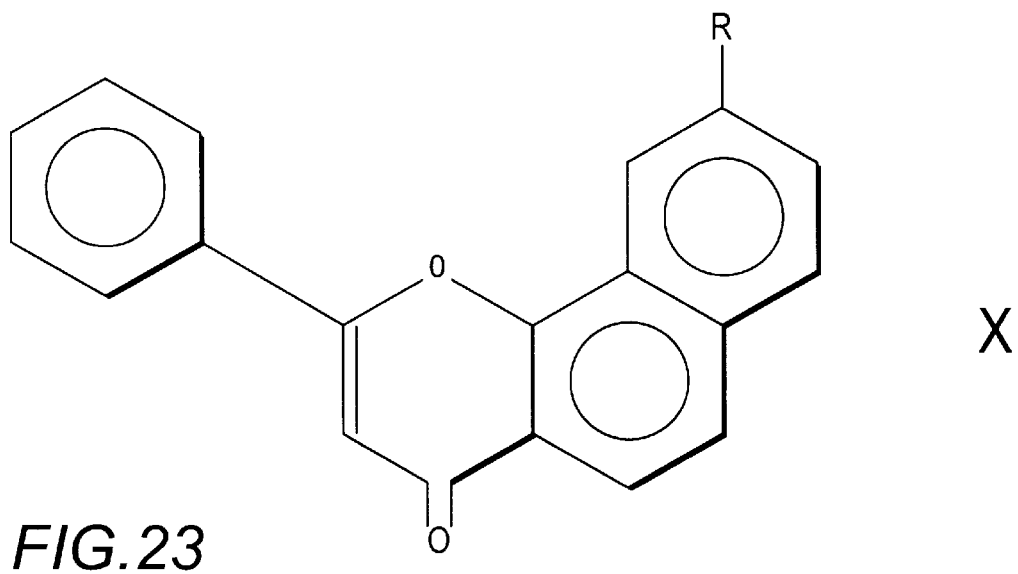

The results are shown in FIG. 12 and in the Table below:

| Dose mg/kg | % Inhibition | |
|---|---|---|
| | SD | MD |
| 0.1 | 72 | 65 |
| 1.0 | 85 | 85 |
| 10.0 | 96 | 89 |

Similar results were found with liver cells.

Compound 14 (coumate) therefore demonstrates potent oral activity.

Other modifications of the present invention will be apparent to those skilled in the art.

Example 14

Compounds Synthesised

The following sulphamate derivatives were synthesised from the following parent compounds:

| PARENT COMPOUND | SULPHAMATE COMPOUND |
|---|---|
| 1 | 2 |
| 3 | 4 |
| 5 | 6 |
| 7 | 8 |
| 9 | 10 | wherein
1=6-hydroxy flavone
2=flavone-6-sulphamate
3=7-hydroxy flavone
4=flavone-7-sulphamate
5=5,7-dihydroxy flavone
6=5-hydroxy-flavone-7-sulphamate
7=5,7-dihydroxy-4'-hydroxy-flavone
8=5,7-dihydroxy flavanone-4'-flavanone sulphamate
9=5,7-dihydroxy-4'-methoxy-isoflavone
10=5-hydroxy-4'-methoxy-isoflavone-isoflavone-7-sulphamate The formulae are presented in FIGS. 16a, 16b, 16c, 17–22

SYNTHESIS

The sulphamate derivatives were prepared essentially as described previously (J. Med. Chem. 37:219–21). In this regard, a solution of the appropriate flavone, isoflavone or flavanone in anhydrous DMF was treated with sodium hydride (60% dispersion; 1 equiv for 2 and 4; 2 equiv for 6, 8 and 10) at 0° C. under an atmosphere of $N_2$. After evolution of hydrogen had ceased, sulfamoyl chloride (2 equiv except for 8.5 equiv) was added and the reaction mixture was poured into brine after warming to room temperature overnight and diluting with ethyl acetate. The organic fraction was washed exhaustively with brine, dried ($MgSO_4$), filtered and evaporated. The crude product obtained was purified by flash chromatography and recrystallisation to give the corresponding sulfamate.

Flavone 6-O-sulphamate (2)

6-Hydroxyflavone (1.0 g, 4.113 mmol) gave crude product (1.21 g) which was fractionated on silica (200 g) with ethyl acetate. Upon evaporation, the first fraction gave a creamy residue (760 mg, 58.2%) which was recrystallised in warm acetone/hexane (3:2) to give 2 as creamy rod-shaped crystals (557 mg), m.p. 190–191° C.; $R_f$s=0.71 (ethyl acetate), 0.51 (ethyl acetate/hexane, 2:1), vmax (KBr) 3260, 3040, 1620, 1580, 1370, 1180 cm$^{-1}$; $\delta_H$ (acetone-$d_6$) 6.917 (1H, s, C-3-$\underline{H}$), 7.355 (2H, br s, exchanged with $D_2O$, —$OSO_2NH_2$), 7.64 (3H, m, C-3'-$\underline{H}$, C-4'-$\underline{H}$ and C-5=-$\underline{H}$), 7.75 (1H, dd, $J_{C-8-H, C-7-H}$=9 Hz and $J_{C-5-H, C-7-H}$=3 Hz, C-7-$\underline{H}$), 7.87 (1H, d, $J_{C-7-H, C-8-H}$=9 Hz, C-8-$\underline{H}$), 8.02 (1H, d, $J_{C-7-H, C-5-H}$=3 Hz, C-5-$\underline{H}$) and 8.13 (2H, m, C-2'-$\underline{H}$ and C-6'-$\underline{H}$). MS: m/z (E.I., rel. intensity) 317.0 (11), 304.2 (6), 238.0 (96), 210.0 (16), 187.1 (14), 152.0 (8). 136.0 (100). Acc. MS (E.I.): m/z 317.0296, $C_{15}H_{11}NO_5S$ requires 317.0358. Found C, 56.7; H, 3.44; N, 4.31. $C_{15}H_{11}NO_5S$ requires C, 56.78; H, 3.49; N, 4.41%.

Flavone 7-O-sulphamate (4)

7-Hydroxyflavone (700 mg, 2.938 mmol) gave crude product (770 mg) which was fractionated on silica (200 g) with ethyl acetate. Upon evaporation, the first fraction gave a light brown residue (132 mg) which was recrystallised in hot isopropyl alcohol to give 4 as white needle-shaped crystals (60 mg), m.p. 172–174° C. (dec.); $R_f$s=0.78 (ethyl acetate), 0.56 (ethyl acetate/hexane, 4.1); vmax (KBr) 3260, 3100, 1630, 1600, 1400, 1580, 1200, 1150 cm$^{-1}$; $\delta_H$ (DMSO-$d_6$/CDCl$_3$, ca. 1:20) 6.824 (1H, s, C-3-$\underline{H}$), 7.396 (1H, dd, $J_{C-5-H, C-6-H}$=8.8 Hz and $J_{C-8-H, C-6-H}$=2.2 Hz, C-6-$\underline{H}$), 7.47 (2H, br s, exchanged with $D_2O$, —$OSO_2NH_2$), 7.55 (3H, m, C-3'-$\underline{H}$, C-4'-$\underline{H}$ and C-5'—$\underline{H}$), 7.639 (1H, d, $J_{C-6-H, C-8-H}$=2.2 Hz, C-8-$\underline{H}$), 7.92 (2H, m, C-2'-$\underline{H}$ and C-6'-$\underline{H}$) and 8.220 (1H, d, $J_{C-6-H, C-5-H}$=8.8 Hz, C-5-$\underline{H}$). Found: C, 56.5; H, 3.36; N, 4.19. $C_{15}H_{11}NO_5S$ requires C, 56.78; H, 3.49; N, 4.41%.

5-Hydroxyflavone 7-O-Sulphamate (6)

5,7-Dihydroxyflavone (1.0 g, 3.933 mmol) gave crude product (1.13 g) which was fractionated on silica (200 g) with chloroform/acetone (8:1). Upon evaporation, the second fraction gave a yellow residue (324 mg, 24.7%) which was recrystallised in ethyl acetate/hexane (1:1) to give 6 as yellow crystals (213 mg), m.p. 195–200° C. (dec.); $R_f$s= 0.21, 0.25 and 0.44 for chloroform/acetone 12:1, 8:1 and 4:1 respectively; vmax (KBr) 3360, 3250, 2925–2850, 1650, 1610, 1380 cm$^{-1}$, $\delta_H$ (acetone-$d_6$) 6.75, 6.98, 7.17 (3H, three s, C-3-H, C-6-H, C-8-H), 7.63 (2H, br s, exchanged with D$_2$O, —OSO$_2$NH$_2$), 7.65 (3H, m, C-3'-H, C-4'-H and C-5'-H), 8.15 (2H, d, J=7.7 Hz, C-2'-H and C-6'-H) and 13.0 (1H, br s, exchanged with D$_2$O, C-5-OH). MS: m/z (+ve ion FAB in m-NBA, rel. intensity) 440.1 (10), 289.2 (10), 334.1[100, (M+H)$^+$], 288.1 (17), 255.0[25, (M+H−79)$^+$], 169.1 (30). MS: m/z (−ve ion FAB in m-NBA, rel. intensity) 499.0 (30), 484.1[14, (M−2H+153)$^-$], 475.1 (20), 443.1 (24), 332.1 [100, (M−H)$^-$], 308.1 (28), 274.1 (20), 253.1[50, (M−H−79)$^-$], 195.1 (24). Acc. MS (+ve ion FAB in m-NBA): m/z 334.0392. C$_{15}$H$_{12}$NO$_6$S requires 334.0385. Found: C, 54.0; H, 3.39; N, 4.21. C$_{15}$H$_{11}$NO$_6$S requires C, 54.03; H, 3.33; N, 4.20%.

5,7-Dihydroxyflavanone 4'-O-sulphamate (8)

4',5,7-Trihydroxyflavanone (1.0 g, 3.675 mmol) gave crude product (965 mg) which was fractionated on silica (200 g) with ethyl acetate/hexane (4:1) to give a mixture of the starting flavanone and product. This mixture was further fractionated on silica (200 g) with chloroform/acetone (4:1) and upon evaporation, the second fraction gave a pale yellow oil (345 mg, 34%) which solidified on standing. Subsequent recrystallisation of this solid in ethyl acetate/hexane (1:1) gave 8 as white crystals (259 mg), m.p. 211–213° C.: R$_f$=0.21 (chloroform/acetone, 4:1); νmax (KBr) 3420, 3340, 3260, 3140, 1640, 1510, 1380, 1160 cm$^{-1}$; δ$_H$ (acetone-d$_6$) 2.84 (1H, dd, J$_{AB}$=17.4 Hz and J$_{ax,eq}$=3.1 Hz, C-3-H$_B$), 3.19 (1H, dd, J$_{BA}$=16.9 Hz and J$_{2A, 2A}$=12.8 Hz, C-3-H$_A$), 5.62 (1H, dd, J$_{2A, 2A}$=3.1 Hz and J$_{2A, 2A}$=12.8 Hz, C-2'-H), 5.98 (1H, d, J=2.0 Hz, C-6-H or C-8-H), 6.01 (1H, d, J=2.0 Hz, C-6-H or C-8-H), 7.20 (2H, br s, exchanged with D$_2$O, —OSO$_2$NH$_2$), 7.40 (2H, d, J=8.7 Hz, C-2'-H and C-6'-H), 7.66 (2H, d, J=8.7 Hz, C-3'-H and C-5'-H), 9.65 (1H, br s, C-7-OH) and 12.15 (1H, s, C-5-OH). MS: m/z (+ve ion FAB in m-NBA, rel. intensity) 352.0 [100, (M+H)$^+$], 288.1 (10), 272.1[14, (M−79)$^-$], 255.2 (9), 169.0 (13). MS: m/z (−ve ion FAB in m-NBA, rel. intensity) 701.2 (12), 606.2 (10), 517.1 (42), 5.04.1[20, (M+153)$^-$], 473.2 (10), 350.1[100, (M−H)$^-$], 271.1[45, (M−H−79)$^-$]172.0 (8). Acc. MS (+ve ion FAB in m-NBA): m/z 352.0496, C$_{15}$H$_{14}$NO$_7$S requires 352.0491. Found: C, 51.1; H, 3.68; N, 3.98. C$_{15}$H$_{13}$NO$_7$S requires C, 51.28; H, 3.73; N, 3.99%.

5-Hydroxy-4'-methoxyisoflavone 7'-O-sulphamate (10)

5,7-Dihydroxy-4'-methoxyisoflavone (800 mg, 2.817 mmol) gave crude product (650 mg) which was fractionated on silica (200 g) with chloroform/acetone (8:1). Upon evaporation, the second fraction gave a yellow residue (266 mg, 26%) which was recrystallised in ethyl acetate/hexane (1:1) to give 10 as yellow crystals (211 mg), m.p. 184–188° C.; r$_f$s=0.22 and 0.59 for chloroform/acetone 8:1 and 4:1 respectively; νmax (KBr) 3300–3020, 1660, 1610, 1400 cm$^{-1}$; δ$_H$ (acetone-d$_6$) 3.86 (3H, s, —OCH$_3$), 6.75 (1H, d, J=2.2 Hz, C-6-H or C-8-H), 7.04 (3H, m, C-6-H or C-8-H and C-3'-H and C-5'-H), 7.49 (2H, br s, exchanged with D$_2$O, —OSO$_2$NH$_2$), 7.58 (2H, d, J=7 Hz, C-2'-H and C-6'-H), 8.41 (1H, s, C-2-H), 13.05 (1H, br s, exchanged with D$_2$O, C-5-OH). MS: m/z (+ve ion FAB in m-NBA, rel. intensity) 393.3 (12), 364.0[100, (M+H)$^+$], 284.1[12, (M−79)$^+$], 169.1 (24), 134.0 (22). MS: m/z (−ve ion FAB in m-NBA, rel. intensity) 529.1 (25), 515.1[12, (M−H+153)$^-$], 442.1 (20), 362.1[100, (M−H)$^-$], 308.1 (34), 283.1[70, (M−H−79)$^-$], 170.1 (26). Acc. MS (+ve ion FAB in m-NBA): m/z 364.0494, C$_{16}$H$_{14}$NO$_7$S requires 364.0491. Found: C, 52.8; H, 3.65; N, 3.81. C$_{16}$H$_{13}$NO$_7$S requires C, 52.89; H, 3.61; N, 3.85%.

5-Hydroxy Isoflavone-4',7-O,O-Disulphamate (11) and 5,7-Dihydroxy Isoflavone-4'-O-Sulphamate (12)

4',5,7-Trihydroxy isoflavone (0.5 g, 1.85 mmol) upon sulphamoylation gave a crude product (0.65 g) which was fractionated on silica (200 g) with chloroform/acetone (4:1), and upon evaporation the third fraction gave a light yellow residue (0.329 g, 51%) which was recrystallized in ethylacetate/hexane (1:2) to give compound (11) as beige crystals (0.197 g); m.p.=>198° C. (dec); R$_f$s=0.14 and 0.24 for chloroform/acetone 4:1 and 2:1 respectively; ν$^{max}$ (KBr) 3460 (—NH$_2$), 1650 (C=O), 1400 (—SO$_2$N—) cm$^{-1}$; δ$_H$ (acetone-d$_6$) 6.78 (1H, d, J=2.2 Hz, C-6-H or C-8-H, 7.03 (1H, d, J=2.2 Hz, C-8-H or C-6-H), 7.4 (4H, br s, exchanged with D$_2$O, C-4'-OSO$_2$NH, and C-7-OSO$_2$NH$_2$), 7.43 (2H, d, J=8.4 Hz, C-3'-H and C-5'-H or C-2'-H and C-6'-H and C-6'-H), 7.72 (2H, d, J=8.4 Hz, C-2'-H and C-6'-H or C-3'-H and C-5'-H), 8.51 (1H, s, C-2-H) and 12.93 (1H, s, C-5-OH). MS: m/z (+ve ion FAB in m-NBA, rel. intensity) 428.9 [100, (M+H)$^+$], 350.0 [20, (M+H—SO$_2$NH$_2$)$^+$], 272.1 [30, (M−H—SO$_2$NH$_2$)$^+$]. MS: m/z (−ve ion FAB in m-NBA, rel. intensity) 426.9 [100, (M−H)$^-$], 347.9 [95, (M−H—SO$_2$NH$_2$)$^-$], 269.0 [30, (M−H—SO$_2$NH$_2$)$^-$]. Acc. MS: m/z (FAB)$^+$ 429.0083 C$_{15}$H$_{13}$N$_2$O$_9$S$_2$ requires 429.0063. Found C, 42.0; H, 2.91; N, 6.45; C$_{15}$H$_{12}$N$_2$O$_9$S$_2$ requires C, 42.06; H, 2.82; N, 6.54%.

The second fraction was collected and upon evaporation gave light yellow residue (0.112 g, 17%) which was recrystallized in ethylacetate/hexane (1:3) to give compound (12) as pale white crystals (0.068 g); m.p.=189–192° C. R$_f$s=0.23 and 0.33 for chloroform/acetone 4:1 and 2:1 respectively; ν$^{max}$ (KBr) 3500–3300 (—NH$_2$), 3200 (H-bonded-OH), 1680 (C=O), 1610, 1400 (—SO$_2$N—)cm$^{-1}$; δ$_H$ (acetone-d$_6$) 6.32 (1H, d, J=2.2 Hz, C-6-H or C-8-H), 6.46 (1H, d, J=2.2 Hz, C-8-H or C-6-H), 7.32 (2H, br s, exchanged with D$_2$O, —SO$_2$NH$_2$), 7.42 (2H, t, J=8.4 Hz, C-3'-H and C-5'-H or C-2'-H and C-6'-H, 7.69 (2H, d, J=8.4 Hz, C-2'-H and C-6'-H or C-3'-H and C-5'-H), 8.31 (1H, s, C-2-H), 9.53 (1H, s, C-7-OH) and 12.9 (1H, s, C-5-OH). MS: m/z (+ve ion FAB in m-NBA, rel. intensity) 350.0 [100, (M+H)$^+$], 271.1 [15, (M+H—SO$_2$NH$_2$)$^+$]. MS: m/z (−ve ion FAB in m-NBA, rel. intensity) 347.9 [100, (M−H)$^-$], 269.0 [20, (M—H—SO$_2$NH$_2$)$^-$]. Acc. MS: m/z (FAB)$^+$ 350.0347 C$_{15}$H$_{12}$NO$_7$S requires 350.0335. Found C, 51.0; H, 3.16; N, 3.90; C$_{15}$H$_{11}$NO$_7$S requires C, 51.58; H, 3.17; N, 4.01%.

Isoflavone-4',7-O,O-Disulphamate (13)

4',7-Dihydroxy isoflavone (0.45 g, 1.77 mmol) upon sulphamoylation gave a crude product, (0.769 g) which was fractionated on silica (200 g) with chloroform/acetone (4:1), and upon evaporation the second fraction gave a pale white residue (0.553 g, 72%) which was recrystallized in acetone/hexane (1:2) to give the compound (13) as white crystals (0.327 g); m.p.>195° C. (dec.); R$_f$s=0.21 and 0.40 for chloroform/acetone 4:1 and 2:1 respectively; ν$^{max}$ (KBr) 3400 (—NH$_2$), 1640 (C=O), 1360 (—SO$_2$N—) cm$^{-1}$, δ$_H$ (DMSO-d$_6$), 7.37 (2H, d, J=8.8 Hz, C-3'-H and C-5'-H or C-2'-H and C-6'-H, 7.42 (1H, dd, J$_{C-6-H, C-8-H}$=2.2 Hz, J$_{C-6-H, C-5-H}$=8.8 Hz, C-6-H), 7.7 (2H, d, J=8.8 Hz, C-2'-H and C-6'-H or C-3'-H and C-5'-H), 8.09 (2H, br s, exchanged with D$_2$, —OSO$_2$NH$_2$), 8.24 (1H, d, J=8.8 Hz, C-5-H, 8.36 (2H, br s, exchanged with D$_2$, —OSO$_2$NH$_2$), 8.63 (1H, s, C-2-H). MS: m/z (+ve ion FAB in m-NBA, rel. intensity) 412.9 [100, (M+H)$^+$], 334.0 [25, (M+H—SO$_2$NH$_2$)$^+$], 255.1 [20, (M+H—SO$_2$NH$_2$)$^+$]. MS: m/z (−ve ion FAB in m-NBA, rel. intensity) 410.9 [100, (M−H)$^-$], 332.0 (70, (M−H—SO$_2$NH$_2$)$^-$], 253.0 [30, (M−H—SO$_2$NH$_2$)$^-$]. Acc. MS: m/z (FAB)$^+$ 413.0119 C$_{15}$H$_{13}$N$_2$O$_8$S$_2$ requires 413.0113. Found C, 44.0; H, 2.94; N, 6.62; C$_{15}$H$_{12}$N$_2$O$_8$S$_2$ requires C, 43.69; H, 2.93; N, 6.79%.

ASSAY OF INHIBITION OF SULPHATASE AND AROMATASE ACTIVITIES

Sulphatase inhibition was assessed using placental microsome (100,000 g) preparations or intact MCF-7 breast cancer cells as described previously. Placental microsomes were incubated with $^3$H E1S, adjusted to 20 µM with unlabelled substrate, in the absence or presence of inhibitor. (J. Med. Chem. 37:219–21; Biochemistry 34:11508–14.)

Placental microsomes were also used to assess the aromatase inhibitory properties of the flavanoid sulphamates using a tritiated water release assay (J. Steroid Biochem 214:1033–39). Further placental microsomes (200 µl) were incubated with [1β-$^3$H] androstenedione, 60 nM and 1 mM NADPH in the absence or presence of inhibitor.

INHIBITION OF SULPHATASE AND AROMATASE ACTIVITIES

Inhibition of oestrone sulphatase and aromatase activities in placental microsomes by the flavanoid sulphamate derivatives is shown in the Table below.

| COMPOUND | CONCENTRATION µM | % INHIBITION Sulphatase | % INHIBITION Aromatase |
|---|---|---|---|
| Flavone-6-sulphamate | 1 | 26.8 | 1 |
|  | 10 | 89.5 | 6.5 |
| Flavone-7-sulphamate | 1 | — | 55 |
|  | 10 | — | 86 |
|  | 50 | 56.3 |  |
|  | 100 | 75.3 |  |
| 5-hydroxy flavone-7-sulphamate | 1 | 8 | 5 |
|  | 10 | 21 | 76 |
| 5,7-dihydroxy flavanone 4'-sulphamate | 0.1 | 30.4 | Not tested |
|  | 1 | 79.1 | Not tested |
|  | 10 | 98.1 | Not tested |
| 5-hydroxy-4'-methoxy-isoflavone-7-sulphamate | 1 | 1 | 2 |
|  | 10 | 50.6 | 5 |

From the results, it can be seen that potent inhibition of sulphatase and aromatase activities was detected. For sulphatase inhibition this ranged from 21% at 10 µM by 5-hydroxy flavone-7-sulphamate, to 98% by 5,7-dihydroxy flavanone-4'-sulphamate at 10 µM. Potent aromatase inhibition was also achieved ranging from 6.5% by flavone-6-sulphamate at 10 µM to 86% by flavone-7-sulphamate at 10 µm.

FURTHER IN VITRO TESTING

The following Table presents in vitro data for three isoflavones that were tested.

IN VITRO ACTIVITY

| Compound | Concentration (µM) | % Inhibition MCF-7 Cells | % Inhibition Placental Microsomes |
|---|---|---|---|
| Isoflavone 5-hydroxy-4',7-bissulphamate | 0.1 | 28 | nd |
|  | 1.0 | 90 | nd |
|  | 10.0 | 99 | 93 |
| Isoflavone 5,7-dihydroxy-4'-sulphamate | 0.1 | 23 | nd |
|  | 1.0 | 83 | nd |
|  | 10.0 | 99 | 75 |
| Isoflavone-4',7-bissulphamate | 0.1 | 89 | nd |
|  | 1.0 | 99 | nd |
|  | 10.0 | 99 | 99 | nd = not done

IN VIVO TESTING

Figure 24:
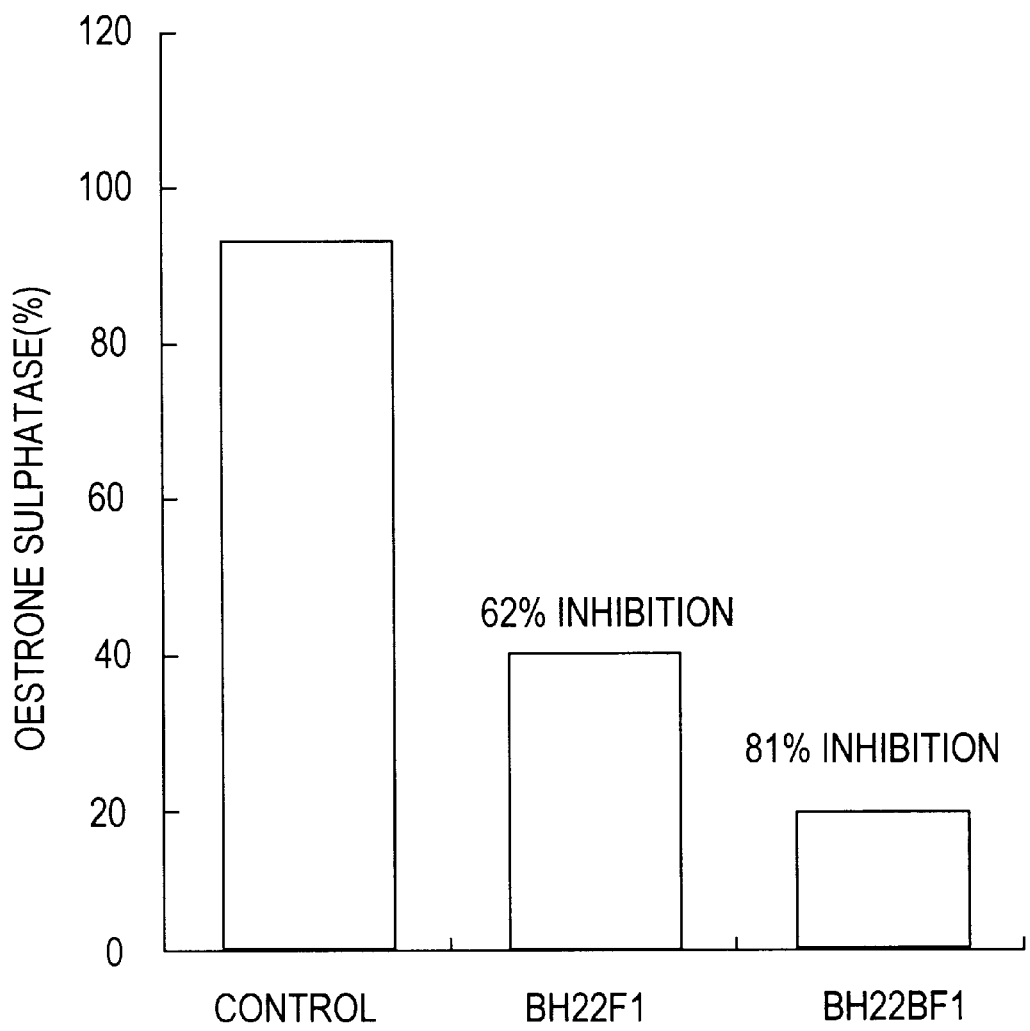
FIG. 24 presents a bar graph of inhibition of oestrone sulphatase (See Example 14 and WO 97/32872).
Figure 29:
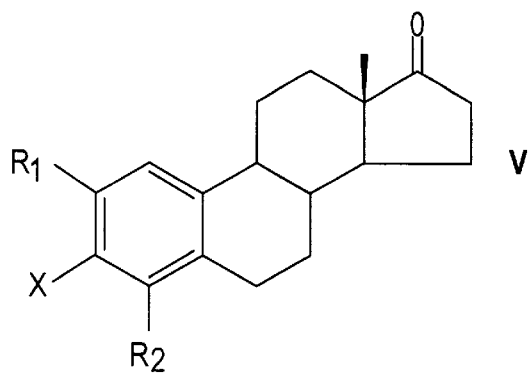
Figure 30:
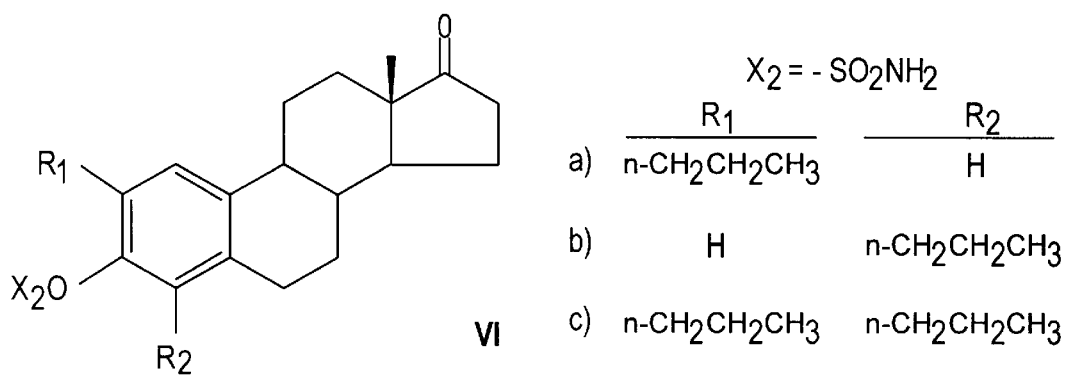
Figure 31:
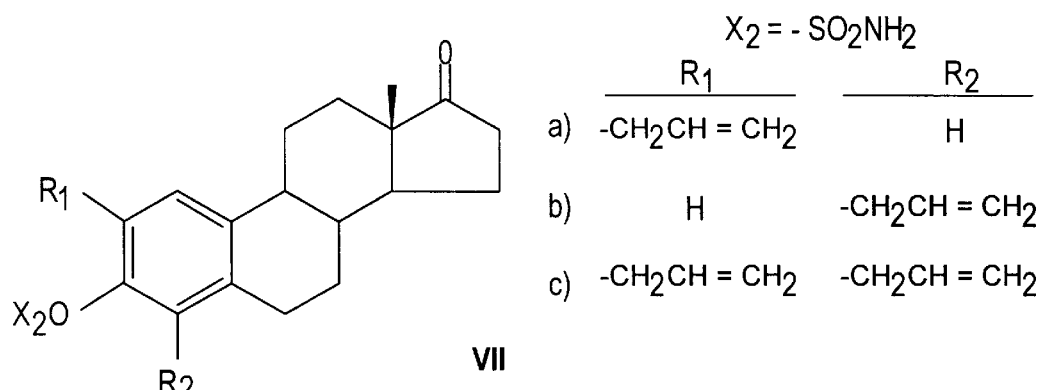
Figure 32:
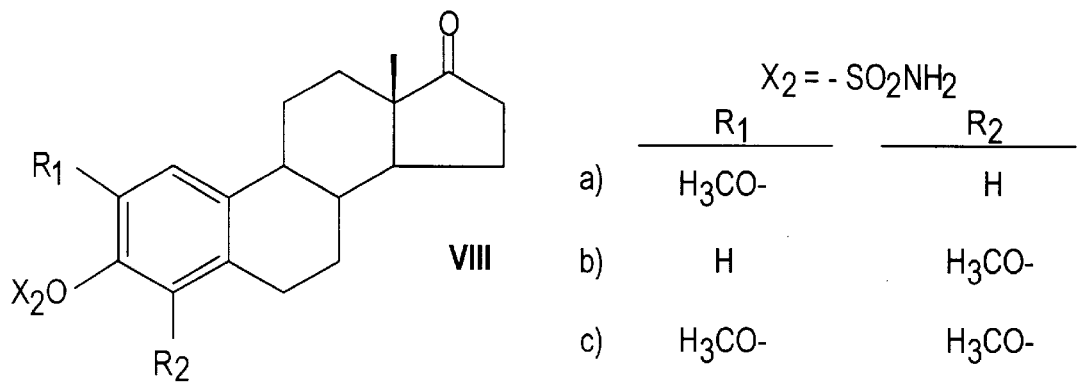
Figure 33:
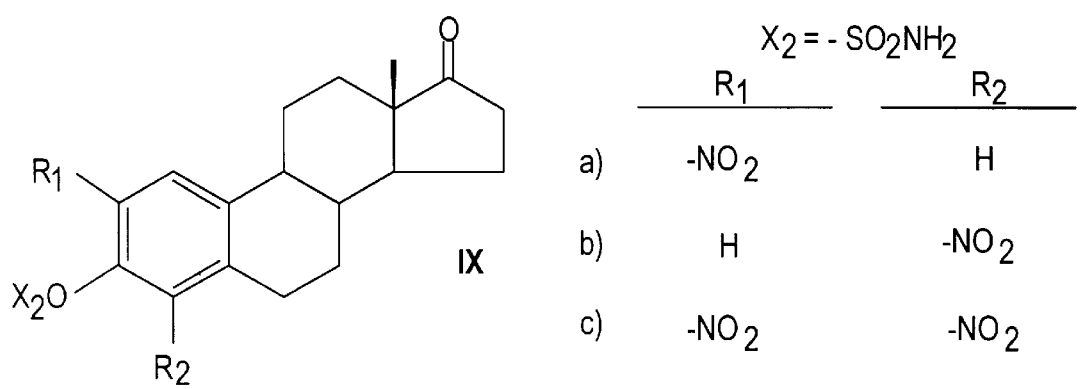
Figure 34:
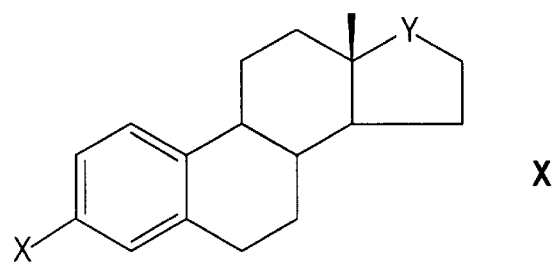
Figure 35:
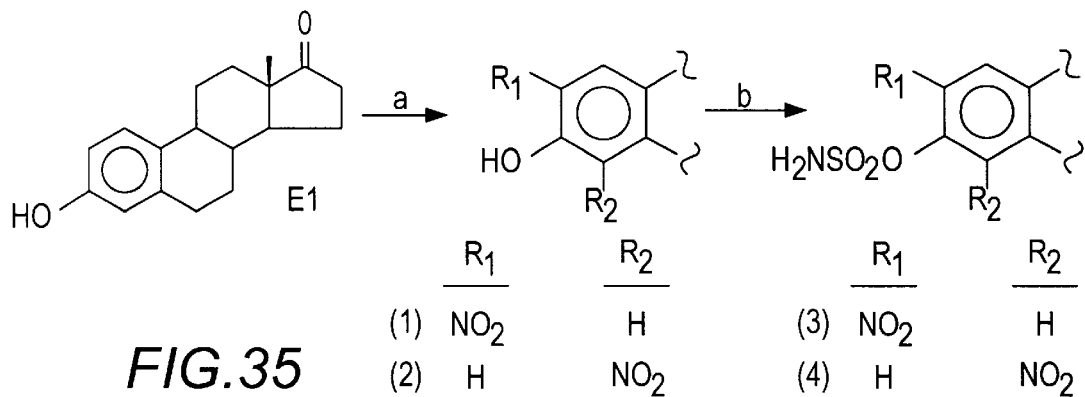
FIGS. 35 to 38 show methods of preparing compounds of the present invention (See Example 15 and WO 98/24802. The sulphamate compounds of the present invention may be prepared by reacting an appropriate alcohol with a sulfamoyl chloride, $R_3R_4NSO_2Cl$. Preferred conditions for carrying out the reaction are as follows: Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous MgSO$_4$. Filtration followed by solvent evaporation in vacuo and co-evaporated with toluene affords a crude residue which is further purified by flash chromatography. Preferably, the alcohol is derivatised, as appropriate, prior to reaction with the sulfamoyl chloride. Where necessary, functional groups in the alcohol may be protected in known manner and the protecting group or groups removed at the end of the reaction).
Figure 36:
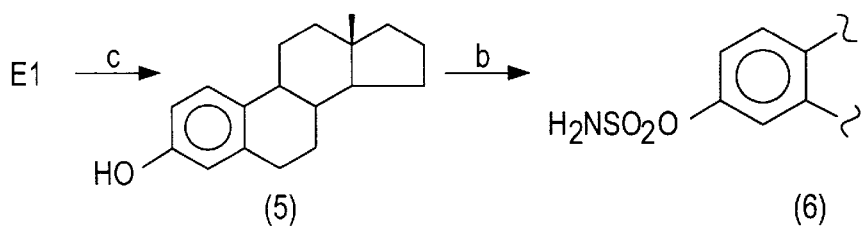
Figure 37:
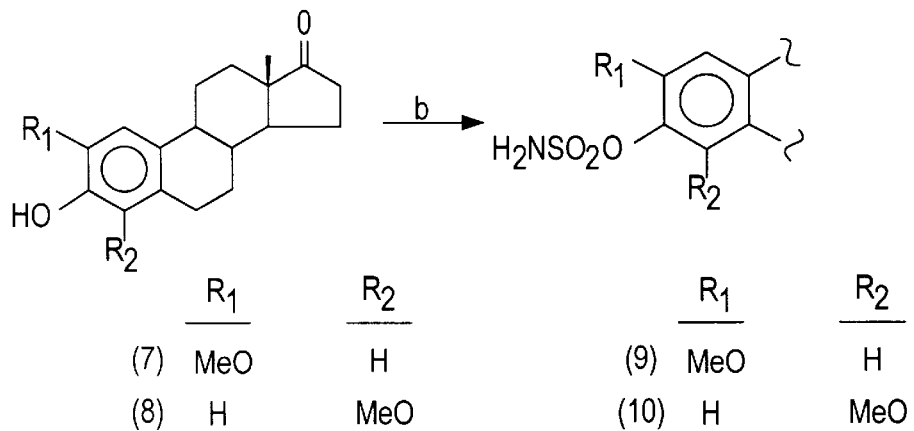
Figure 38:
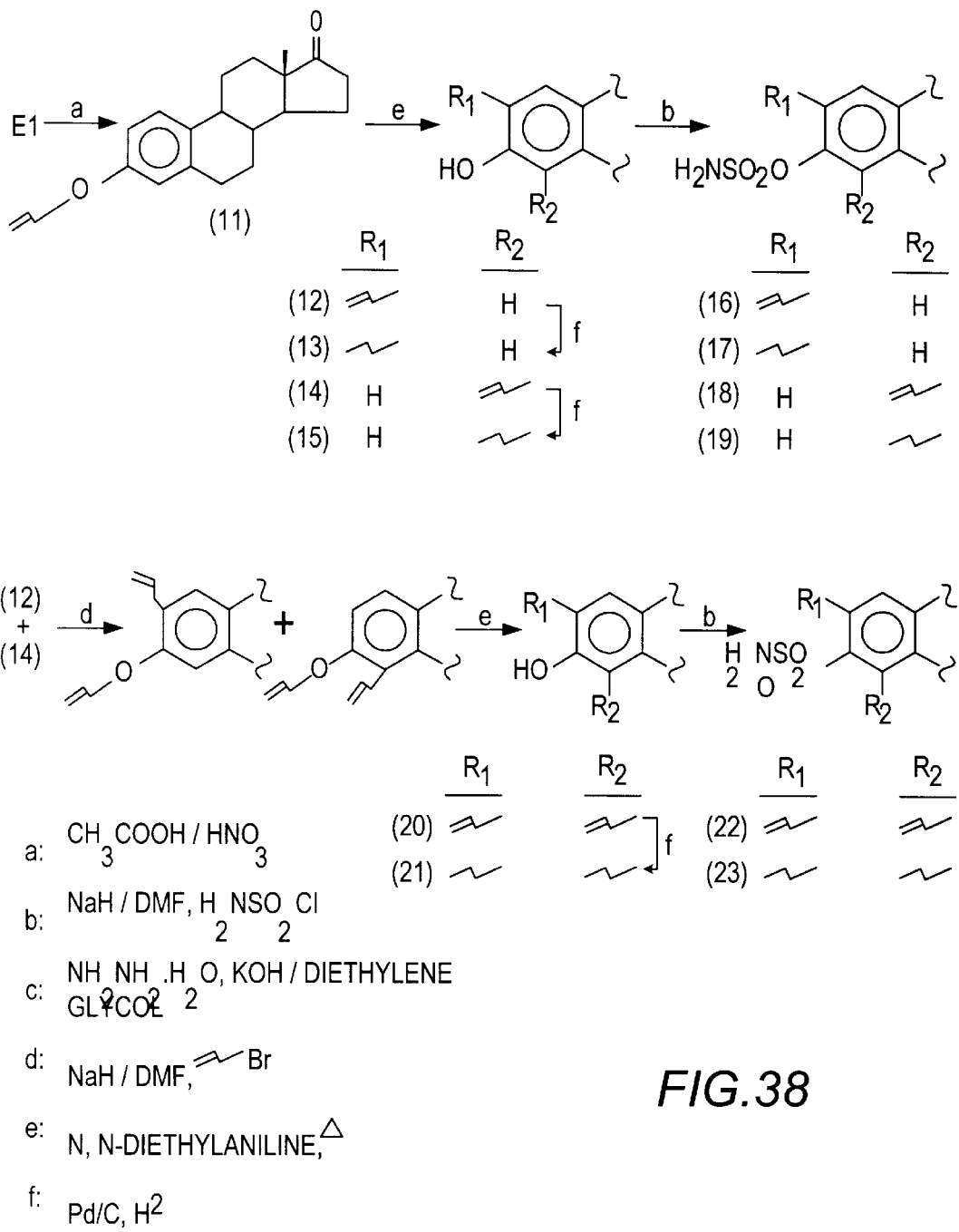

FIG. 24 presents in vivo inhibition of oestrone sulphatase activity in rat liver for two isoflavones according to the present invention. In this regard, BH22F1=5-hydroxy isoflavone-4',7-bissulphamate; BH22BF1=5,7-dihydroxy isoflavone-4'-sulphamate. Compounds were administered as a single 10 mg/Kg dose. Oestrone sulphatase activity was assayed in tissue samples obtained 24 h after drug administration.

Other modifications of the present invention will be apparent to those skilled in the art.

Example 15

Preparative Methods

The preparation of various compounds in accordance with the present invention is illustrated in FIGS. 35 to 38. In these Figures, the curved lines attached to the phenyl rings represent the remainder of the ringed structure.

In Vitro Inhibition

The ability of compounds to inhibit oestrone sulphatase activity was assessed using either intact MCF-7 breast cancer cells or placental microsomes as previously described. (Int. J. Cancer 1995, 62, 106–11.)

In this regard, the teachings of that earlier reference are as follows:

Inhibition of Steroid Sulphatase Activity in MCF-7 cells by oestrone-3-sulphamate Steroid sulphatase is defined as: Steryl Sulphatase EC 3.1.6.2.

Steroid sulphatase activity was measured in vitro using intact MCF-7 human breast cancer cells. This hormone dependent cell line is widely used to study the control of human breast cancer cell growth. IT possesses significant steroid sulphatase activity (MacIndoe et al. *Endocrinology*, 123, 1281–1287 (1988); Purohit & Reed, *Int. J. Cancer*, 50, 901–905 (1992)) and is available in the U.S.A. from the American Type Culture Collection (ATCC) and in the U.K. (e.g. from The Imperial Cancer Research Fund). Cells were maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm$^2$ tissue culture flasks were seeded with approximately 1×10$^5$ cells/flask using the above medium. Cells were grown to 80% confluency and medium was changed every third day.

Intact monolayers of MCF-7 cells in triplicate 25 cm$^2$ tissue culture flasks were washed with Earle's Balanced Salt Solution (EBSS from ICN Flow, High Wycombe, U.K.) and incubated for 3–4 hours at 37° C. with 5 pmol (7×10$^5$ dpm) [6,7-$^3$H]oestrone-3-sulphate (specific activity 60 Ci/mmol from New England Nuclear, Boston, Mass., U.S.A.) in serum-free MEM (2.5 ml) together with oestrone-3- sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flash was cooled and the medium (1 ml) was pipetted into separate tubes containing [$^{14}$C] oestrone (7×10$^3$ dpm) (specific activity 97 Ci/mmol from Amersham International Radiochemical Centre, Amersham, U.K.). The mixture was shaken thoroughly for 30 seconds with toluene (5 ml). Experiments shows that >90% [$^{14}$C] oestrone and <0.1% [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C]oestrone added) and the specific activity of the substrate. Each bath of experiments included incubations of microsomes prepared from a sulphatase-positive human placenta (positive control) and flasks without cells (to assess apparent non-enzymatic hydrolysis of the substrate). The number of cell nuclei per flask was determined using a Coulter Counter after treating the cell monolayers with Zaponin. One flask in each bath was used to assess cell membrane status and viability using the Trypan Blue exclusion method (Phillips, H. J. (1973) In: *Tissue culture and applications*, [eds: Kruse, D. F. & Patterson, M. K.]; pp. 406–408; Academic Press, New York).

Results for steroid sulphatase activity are expressed as the mean ±1 S.D. of the total product (oestrone+oestradiol) formed during the incubation period (20 hours) calculated for 10$^6$ cells and, for values showing statistical significance, as a percentage reduction (inhibition) over incubations containing no oestrone-3-sulphamate. Unpaired Student's t-test was used to test the statistical significance of results.

Inhibition of Steroid Sulphatase Activity in Placental Microsomes by Oestrone-3-sulphamate Sulphatase-positive human placenta from normal term pregnancies (Obsteric Ward, St. Mary's Hospital, London) were thoroughly minced with scissors and washed once with cold phosphate buffer (pH 7.4, 50 mM) then re-suspended in cold phosphate buffer (5 ml/g tissue). Homogenisation was accomplished with an Ultra-Turrax homogeniser, using three 10 second bursts separated by 2 minute cooling periods in ice. Nuclei and cell debris were removed by centrifuging (4° C.) at 2000 g for 30 minutes and portions (2 ml) of the supernatant were stored at −20° C. The protein concentration of the supernatants was determined by the method of Bradford (*Anal. Biochem.*, 72, 248–254 (1976)).

Incubations (1 ml) were carried out using a protein concentration of 100 mg/ml, substrate concentration of 20 mM, [6,7-$^3$H]oestrone-3-sulphate (specific activity 60 Ci/mmol from New England Nuclear, Boston, Mass., U.S.A.) and incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample was cooled and the medium (1 ml) was pipetted into separate tubes containing [$^{14}$C]oestrone (7×10$^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$C]oestrone and <0.1% [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C] oestrone added) and the specific activity of the substrate.

For the present invention, the percentage inhibition for the series of EMATE analogues tested in either MCF-7 cells or placental microsomes is shown in Table 1, below.

In Vivo Studies

Using 17-deoxy oestrone-3-O-sulphamate (NOMATE, FIG. 28, Formula IV where X=—OSO$_2$NH$_2$, Y=—CH$_2$— and R$_1$ and R$_2$=H, and FIG. 36) as a representative example, the ability of this compound to inhibit oestrone sulphatase activity in vivo was examined in rats. The oestrogenicity of this compound was examined in ovariectomised rats. In this model compounds which are oestrogenic stimulate uterine growth.

(i) Inhibition of oestrone sulphatase activity in vivo

NOMATE (0.1 mg/Kg/day for five days) was administered orally to rats with another group of animals receiving vehicle only (propylene glycol). At the end of the study samples of liver tissue were obtained and oestrone sulphatase activity assayed using $^3$H oestrone sulphate as the substrate as previously described (Int. J. Cancer, 1995, 62, 106–11).

Figure 39:
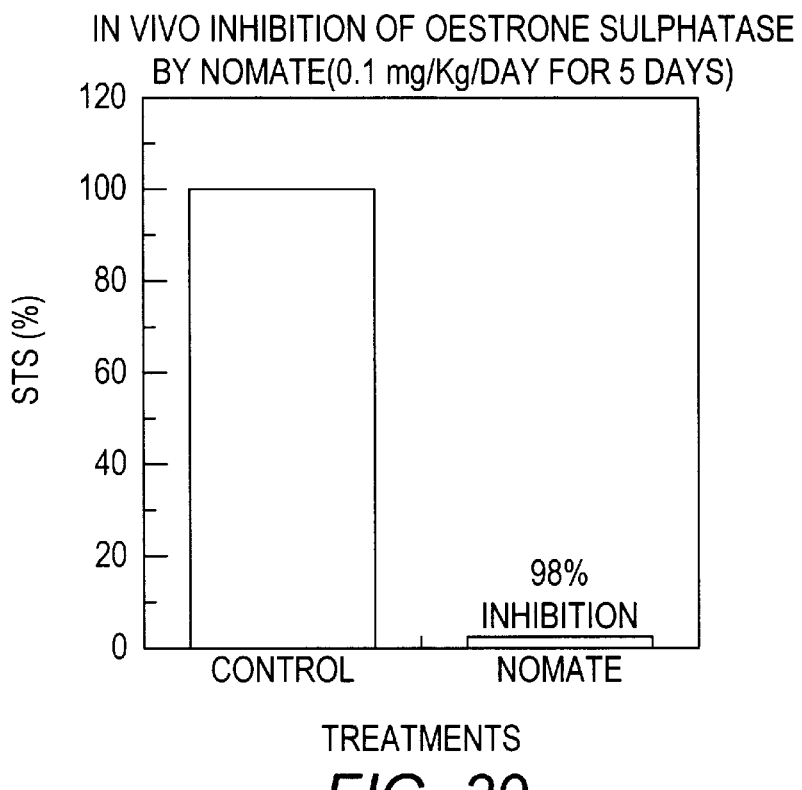
FIG. 39 shows a graph illustrating the in vivo inhibition of oestrone sulphatase by NOMATE (0.1 mg/Kg/day for five days) (See Example 15 and WO 98/24802).

As shown in FIG. 39, administration of this dose of NOMATE effectively inhibited oestrone sulphatase activity by 98% compared with untreated controls.

(ii) Lack of in vivo oestrogenicity

NOMATE (0.1 mg/Kg/day for five days) was administered orally to rats with another group of animals receiving vehicle only (propylene glycol). At the end of the study uteri were obtained and weighed with the results being expressed as uterine weight/whole body weight×100.

Figure 40:
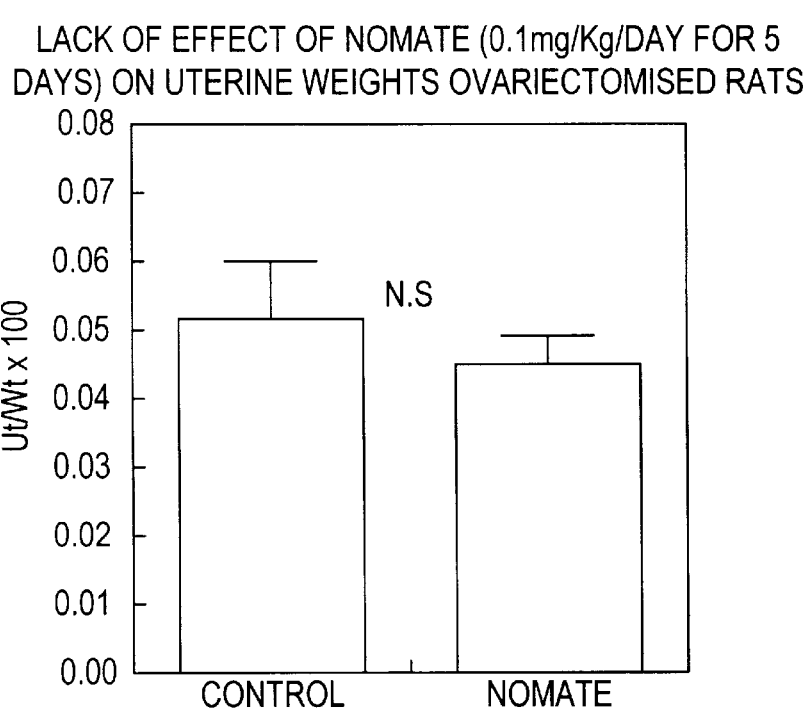
FIG. 40 shows a graph illustrating the lack of effect of NOMATE (0.1 mg/Kg/day for five days) on uterine weights in ovariectomised rats (See Example 15 and WO 98/24802).

As shown in FIG. 40, administration of NOMATE at the dose tested, but had no significant effect on uterine growth, showing that at this dose the compound is not oestrogenic.

TABLE 1

Inhibition of Oestrone Sulphatase Activity in MCF-7 Cells or Placental Microsomes by EMATE Analogues

| Inhibitor | Concentration Tested (mM) | % Inhibition (Mean) MCF-7 Cells | % Inhibition (Mean) Placental Microsomes |
|---|---|---|---|
| 2-n-propyl EMATE | 0.1 | 41.1 | — |
|  | 1 | 83.1 | 21.9 |
|  | 10 | 92.2 | 43.2 |
|  | 25 | — | 47.5 |
|  | 50 | — | 61.1 |
|  | 100 | — | 69.2 |
| 4-n-propyl EMATE | 1 | — | 13.7 |
|  | 10 | — | 10.2 |
|  | 25 | — | 15.7 |
|  | 50 | — | 16.3 |
|  | 100 | — | 23.7 |
| 2,4-n-dipropyl EMATE | 0.1 | 6.6 | — |
|  | 1 | 10.6 | — |
| 2-allyl EMATE | 0.01 | 23.2 | — |
|  | 0.1 | 76.1 | — |
|  | 1 | 94.2 | 45.6 |
|  | 10 | 93.7 | 65.4 |
|  | 25 | — | 75.3 |
|  | 50 | — | 86.6 |
|  | 100 | — | 89.6 |
| 4-allyl EMATE (approx 75%) | 1 | — | 29.1 |
|  | 10 | — | 54.2 |
|  | 25 | — | 59.0 |
|  | 50 | — | 65.1 |
|  | 100 | — | 71.9 |

TABLE 1-continued

Inhibition of Oestrone Sulphatase Activity in MCF-7 Cells or Placental Microsomes by EMATE Analogues

| Inhibitor | Concentration Tested (mM) | % Inhibition (Mean) MCF-7 Cells | % Inhibition (Mean) Placental Microsomes |
|---|---|---|---|
| 2,4-di-allyl EMATE | — | — | — |
| 2-methoxy EMATE | 0.1 | 96.0 | — |
|  | 1 | 93.6 | — |
|  | 10 | 96.2 | 99.0 |
|  | 50 | — | 99.7 |
|  | 100 | — | 99.7 |
| 2-nitro EMATE | 0.05 | — | 44.5 |
|  | 0.5 | — | 93.9 |
|  | 5 | — | 99.0 |
|  | 50 | — | 99.4 |
| 4-nitro EMATE | 20 | — | 99.0 |
| NOMATE | 0.1 | 96.4 | 97.2 |
| (17-deoxy EMATE) | 1 | 99.1 | 99.5 |
|  | 10 | 99.7 | 99.5 |
|  | 25 | 99.7 | 99.7 |

— = not tested
Irreversible time- and concentration-dependent inhibition is assumed for these compounds in keeping with established precendent (Biochemistry, 1995, 34, 11508–11)

Other modifications of the present invention will be apparent to those skilled in the art.

What is claimed is:

1. A method of inhibiting steroid sulphatase activity in a patient in need thereof comprising administering a ring system compound having a sulphamic acid ester group; wherein said compound is an inhibitor of an enzyme having steroid sulphatase activity (EC 3.1.6.2); and wherein when the sulphamic acid ester group of said compound is replaced with a sulphate group to form a sulphate compound and incubated with a steroid sulphatase enzyme (EC 3.1.6.2) at a pH 7.4 and 37° C. it provides a $K_m$ value of less than 50 $\mu$M.

2. The method of claim 1 wherein the ring system compound has the formula:

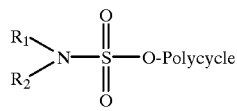

wherein each of $R_1$ and $R_2$ is independently selected from H, alkyl, alkenyl, cycloalkyl and aryl, and at least one of $R_1$ and $R_2$ is H; or, together represent alkylene optionally having one or more hetero atoms or groups in the alkylene chain;

wherein the group Polycycle is a polycyclic ring structure;

wherein said compound is an inhibitor of an enzyme having steroid sulphatase activity (EC 3.1.6.2); and wherein when the sulphamate group of said compound is replaced with a sulphate group to form a sulphate compound and incubated with a steroid sulphatase enzyme (EC 3.1.6.2) at a pH of 7.4 and 37° C. it provides a $K_m$ value of less than 50 $\mu$M.

3. The method of claim 1 wherein the ring system compound has a non-steroidal ring system to which is attached a sulphamate group of the formula:

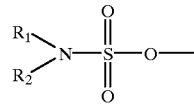

wherein each of $R_1$ and $R_2$ is independently selected from H, alkyl, alkenyl, cycloalkyl and aryl, or, together represent alkylene optionally having one or more hetero atoms or groups in the alkylene chain; and, wherein said compound is an inhibitor of an enzyme having steroid sulphatase activity (EC 3.1.6.2); and wherein when the sulphamate group of said compound is replaced with a sulphate group to form a sulphate compound and incubated with a steroid sulphatase enzyme (EC 3.1.6.2) at a pH of 7.4 and 37° C. it provides a $K_m$ value of less than 50 $\mu$M.

4. The method according to any one of claims 1, 2 or 3, wherein the ring system compound has a six-membered ring to which is attached the sulphamate group.

5. The method of claim 4 wherein the six-membered ring is a six-membered carbon ring to which is attached the sulphamate group.

6. The method according to claim 3, wherein at least one of $R_1$ and $R_2$ is hydrogen.

7. The method according to any one of claims 2 or 3, wherein $R_1$ and $R_2$ is selected from H, alkyl, alkenyl, cycloalkyl and aryl.

8. The method according to claim 3, wherein at least one of $R_1$ and $R_2$ is hydrogen, and the other of $R_1$ and $R_2$ is selected from H, alkyl, alkenyl, cycloalkyl and aryl.

9. The method according to any one of claims 2 or 7, wherein $R_1$ and $R_2$ together represent alkylene optionally having one or more hetero atoms or groups in the alkylene chain.

* * * * *

UNITED STATES PATENT AND TRADEMARK OFFICE
CERTIFICATE OF CORRECTION

PATENT NO. : 6,159,960
DATED : December 12, 2000
INVENTOR(S) : Reed et al.

Page 1 of 1

It is certified that error appears in the above-identified patent and that said Letters Patent is hereby corrected as shown below:

Under [56], References Cited, OTHER PUBLICATIONS:
Line 2, change "Stoler" to -- Stolzner -- and
Line 7, change "Clausen" to -- Claussen --.

Signed and Sealed this

Twenty-fourth Day of July, 2001

Attest:

NICHOLAS P. GODICI
Attesting Officer
Acting Director of the United States Patent and Trademark Office